(12) United States Patent
Gilbride et al.

(10) Patent No.: US 11,684,483 B2
(45) Date of Patent: Jun. 27, 2023

(54) INTERBODY SPACER AND BONE PLATE ASSEMBLY

(71) Applicant: Elevation Spine, Inc., Salinas, CA (US)

(72) Inventors: Charles Gilbride, Salinas, CA (US); Trevor Lewis, Lehi, UT (US); Andrew Fauth, North Logan, UT (US)

(73) Assignee: Elevation Spine, Inc., Salinas, CA (US)

( * ) Notice: Subject to any disclaimer, the term of this patent is extended or adjusted under 35 U.S.C. 154(b) by 89 days.

(21) Appl. No.: 16/986,364

(22) Filed: Aug. 6, 2020

(65) Prior Publication Data

US 2020/0368035 A1  Nov. 26, 2020

Related U.S. Application Data

(63) Continuation of application No. 16/025,935, filed on Jul. 2, 2018, now Pat. No. 10,758,370.

(Continued)

(51) Int. Cl.
*A61F 2/44* (2006.01)
*A61F 2/46* (2006.01)
(Continued)

(52) U.S. Cl.
CPC .......... *A61F 2/447* (2013.01); *A61B 17/844* (2013.01); *A61B 17/846* (2013.01); *A61B 17/866* (2013.01); *A61B 17/8685* (2013.01); *A61F 2/30749* (2013.01); *A61F 2/442* (2013.01); *A61F 2/4611* (2013.01); *A61B 17/1757* (2013.01); *A61B 17/8875* (2013.01); *A61F 2/4603* (2013.01); *A61F 2002/30169* (2013.01); *A61F 2002/30433* (2013.01); *A61F 2002/30448* (2013.01); *A61F 2002/30451* (2013.01); *A61F 2002/30481* (2013.01); *A61F 2002/30579* (2013.01); *A61F 2002/30593* (2013.01); *A61F 2002/30604* (2013.01); *A61F 2002/30622* (2013.01); *A61F 2002/30787* (2013.01); *A61F 2002/30841* (2013.01); *A61F 2002/30881* (2013.01); *A61F 2002/30889* (2013.01);

(Continued)

(58) Field of Classification Search
CPC ... A61B 17/844; A61B 17/846; A61B 17/866; A61B 17/8685; A61F 2/447
See application file for complete search history.

(56) References Cited

U.S. PATENT DOCUMENTS

2011/0230971 A1* 9/2011 Donner ............... A61F 2/442
606/246
2013/0245767 A1* 9/2013 Lee ................... A61F 2/442
623/17.16

(Continued)

*Primary Examiner* — Tessa M Matthews
(74) *Attorney, Agent, or Firm* — David Meibos; Maywood IP Law

(57) ABSTRACT

Implant assemblies, systems, and methods for stabilizing a joint between a superior vertebra and an inferior vertebra may include a plate member coupled to an interbody spacer with at least one fastener that extends superiorly or inferiorly from the implant assembly to anchor within a vertebral body and stabilize the joint. Inserters and methods of insertion may also be included to facilitate fixation of various implant assemblies within the intervertebral space of the joint between the superior vertebra and the inferior vertebra.

21 Claims, 41 Drawing Sheets

Related U.S. Application Data

(60) Provisional application No. 62/527,035, filed on Jun. 30, 2017.

(51) Int. Cl.
*A61B 17/86* (2006.01)
*A61B 17/84* (2006.01)
*A61B 17/17* (2006.01)
*A61B 17/88* (2006.01)
*A61F 2/30* (2006.01)

(52) U.S. Cl.
CPC ............ *A61F 2002/30894* (2013.01); *A61F 2002/30904* (2013.01); *A61F 2002/4615* (2013.01); *A61F 2002/4627* (2013.01)

(56) References Cited

U.S. PATENT DOCUMENTS

| | | | | |
|---|---|---|---|---|
| 2015/0328009 | A1* | 11/2015 | Zappacosta | A61F 2/442 623/17.16 |
| 2016/0151171 | A1* | 6/2016 | Mozeleski | A61B 17/7059 623/17.16 |
| 2016/0220388 | A1* | 8/2016 | Flores | A61F 2/4611 |
| 2016/0242923 | A1* | 8/2016 | Davenport | A61F 2/4455 |
| 2018/0303623 | A1* | 10/2018 | Shoshtaev | A61F 2/447 |

* cited by examiner

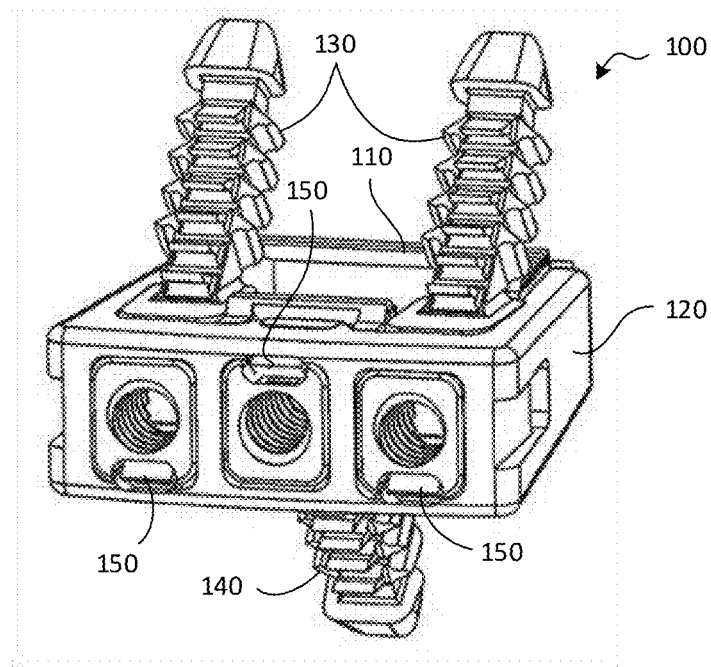
Fig. 1A
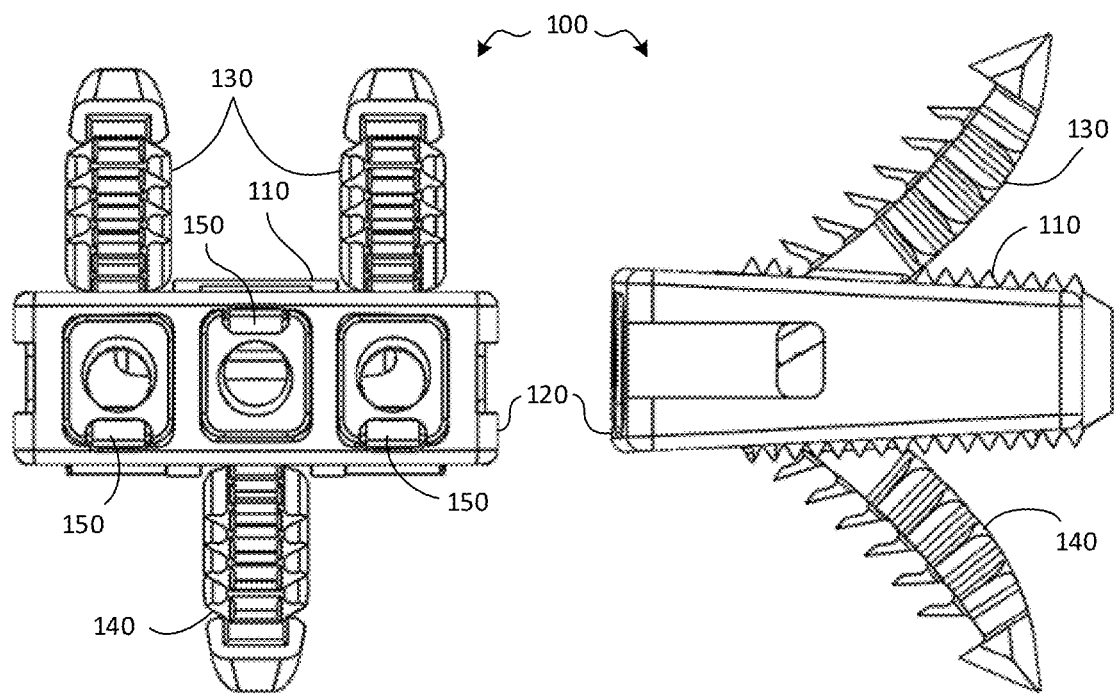
Fig. 1B  Fig. 1C

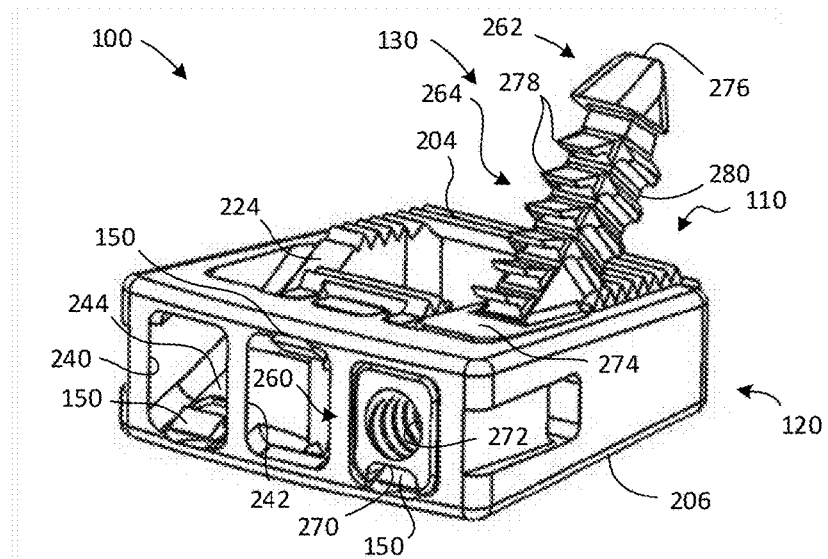
Fig. 4A
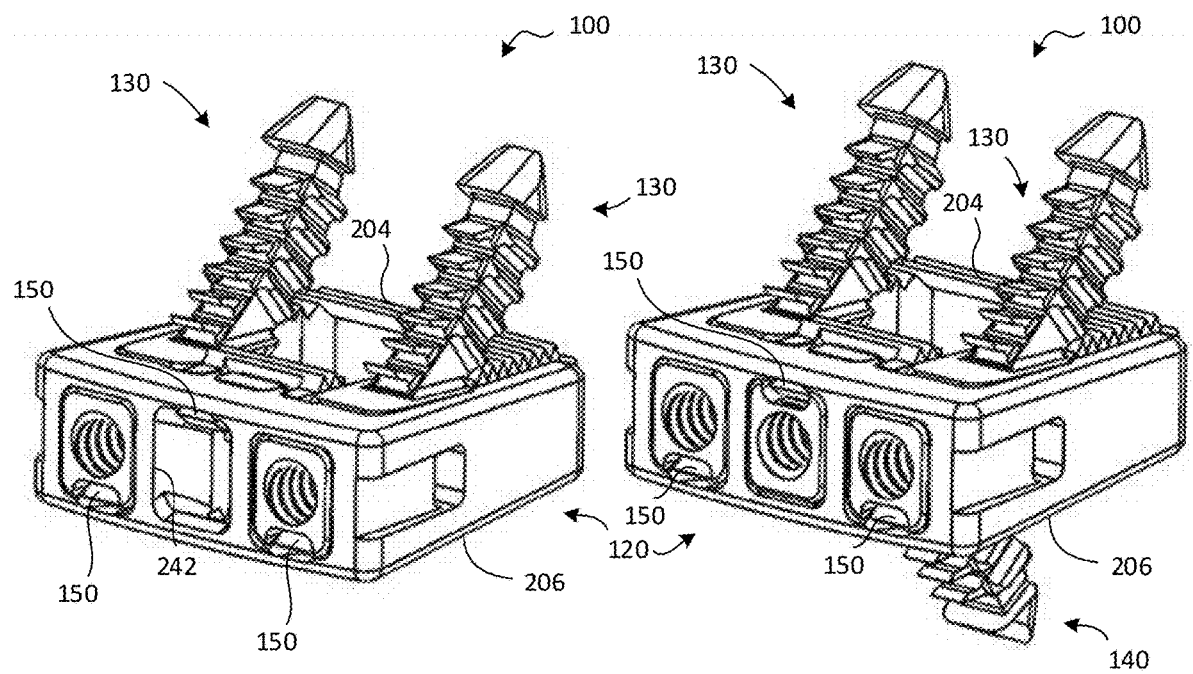
Fig. 4B  Fig. 4C

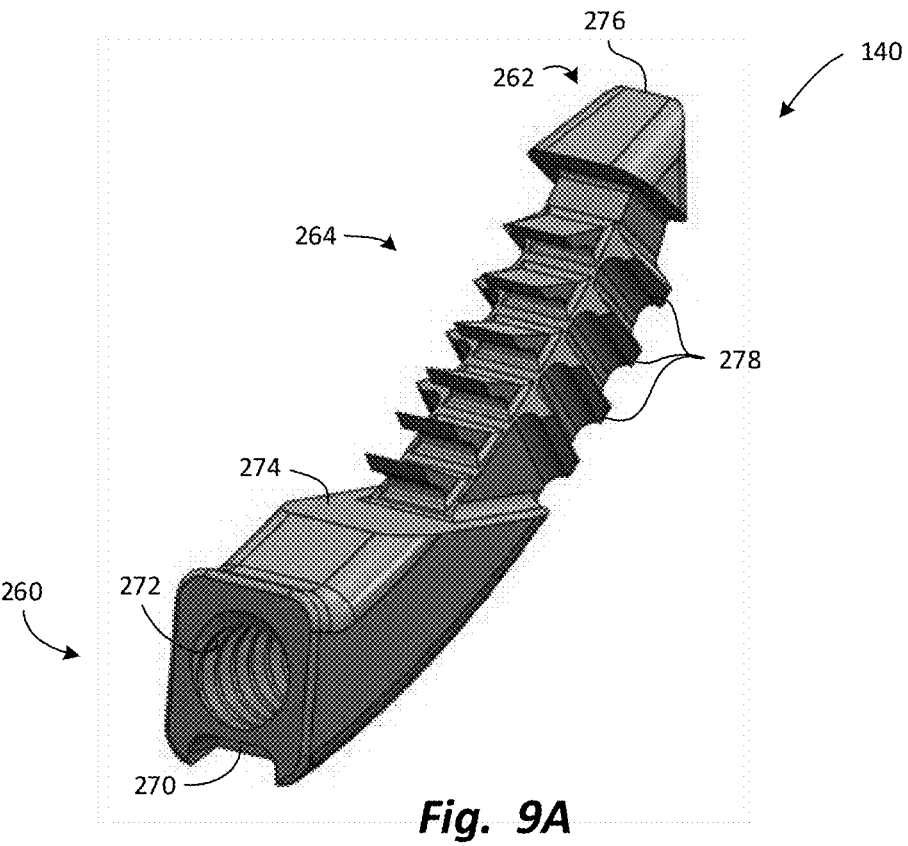
*Fig. 9A*
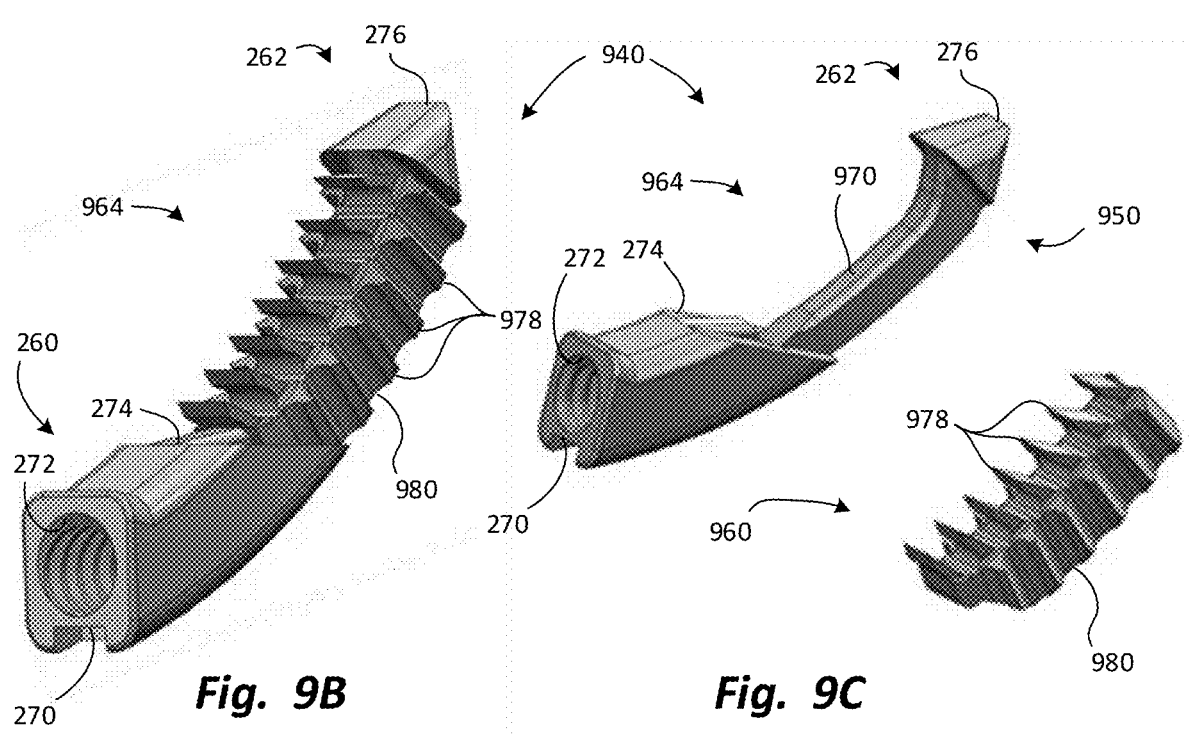
*Fig. 9B*  *Fig. 9C*

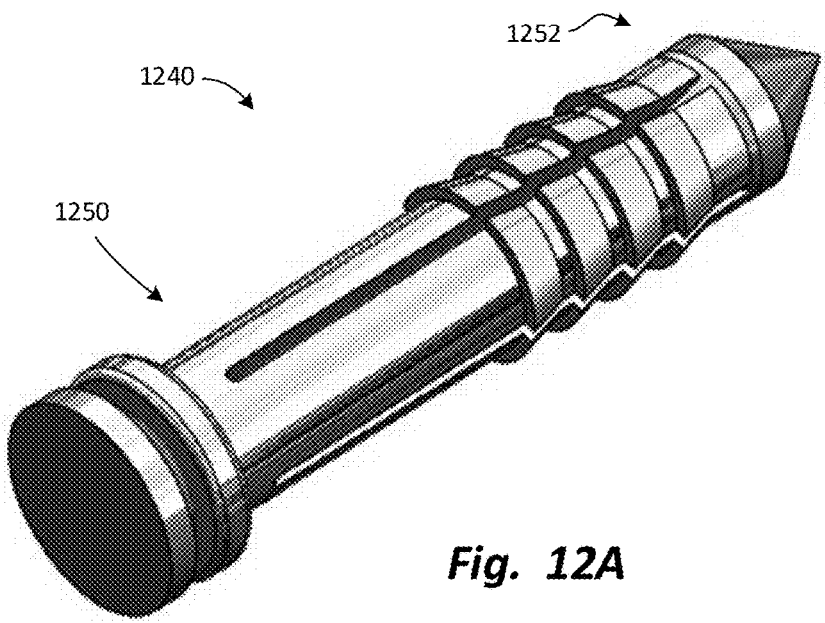
Fig. 12A
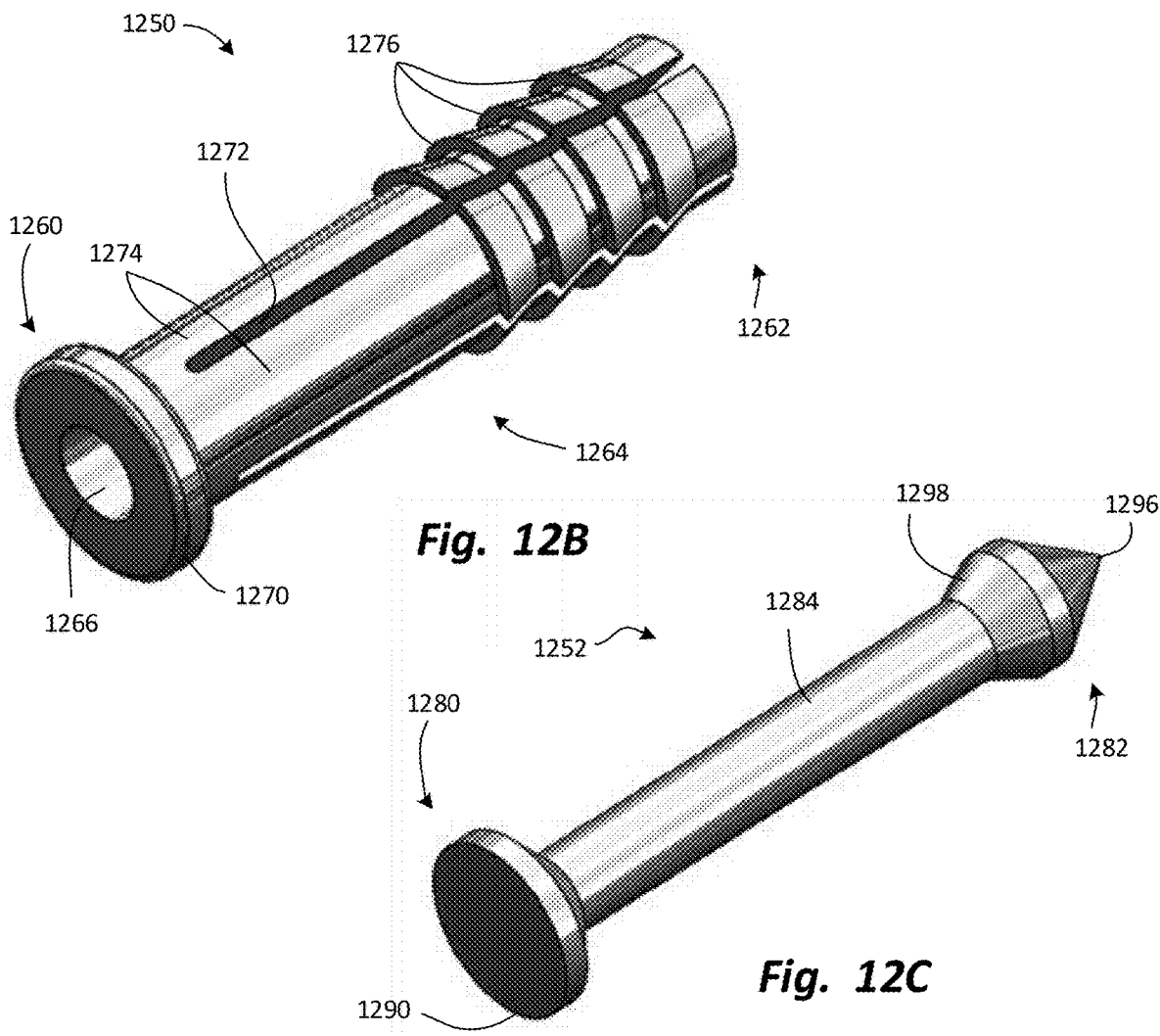
Fig. 12B
Fig. 12C

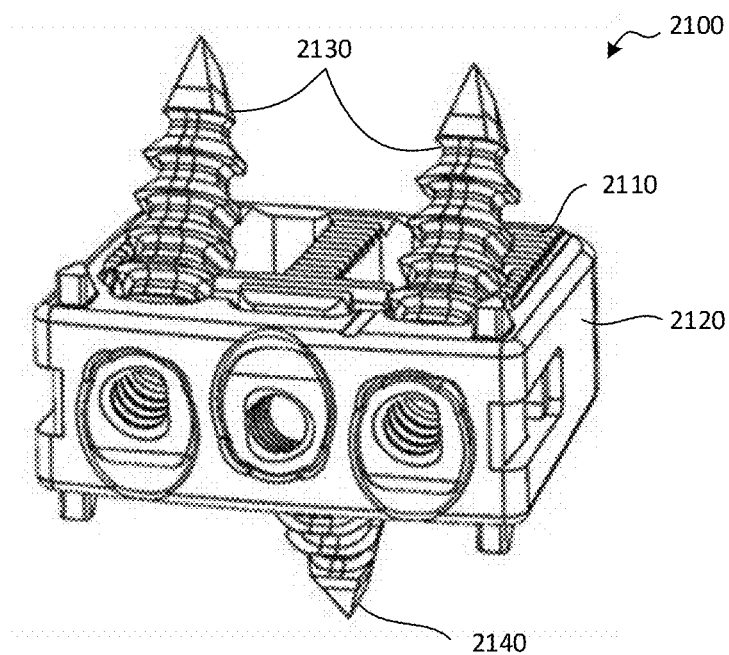
*Fig. 14A*
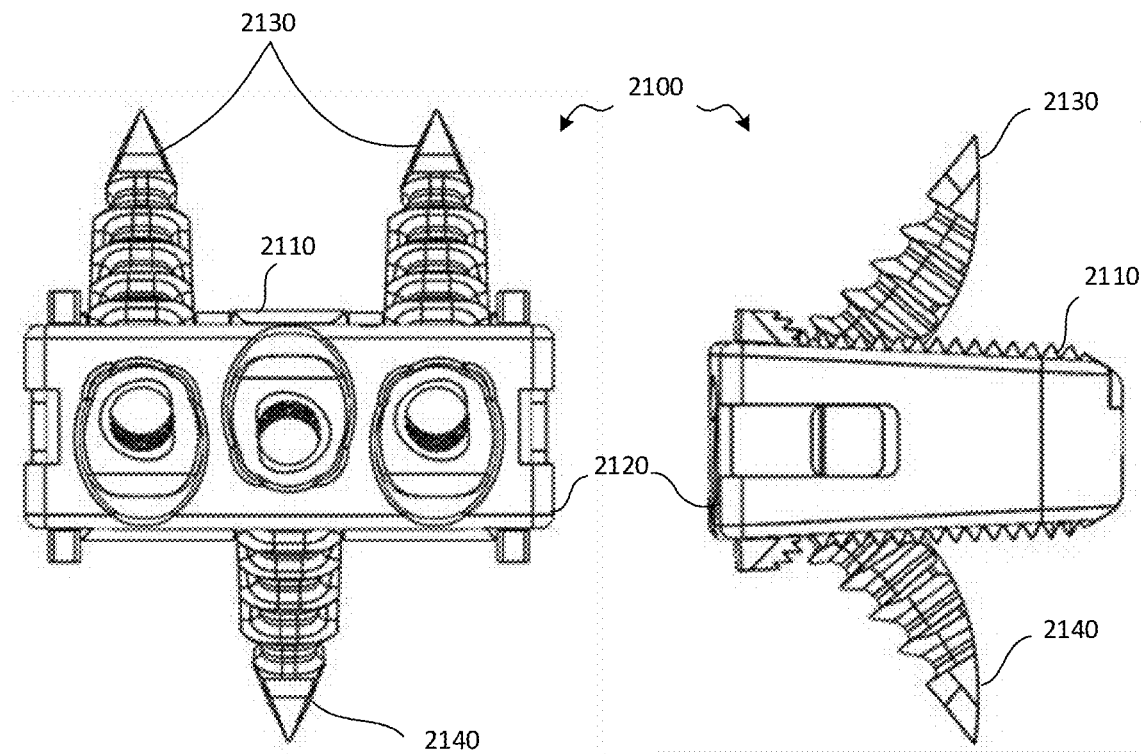
*Fig. 14B*  *Fig. 14C*

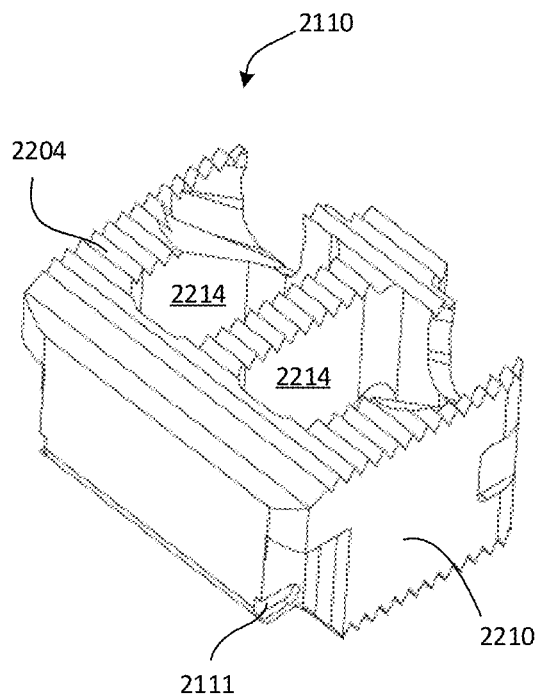
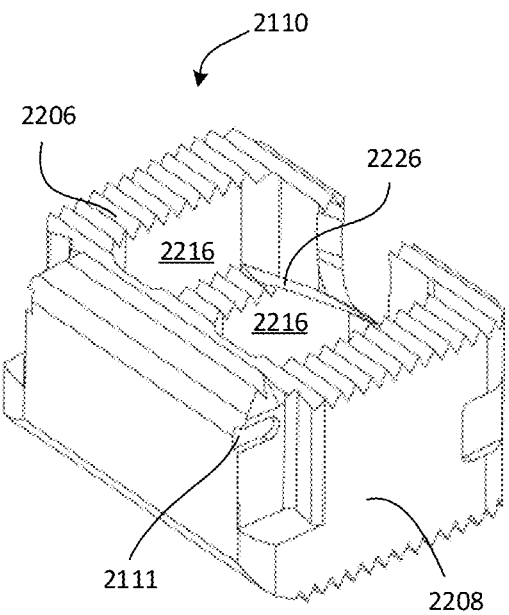
Fig. 16A                Fig. 16B
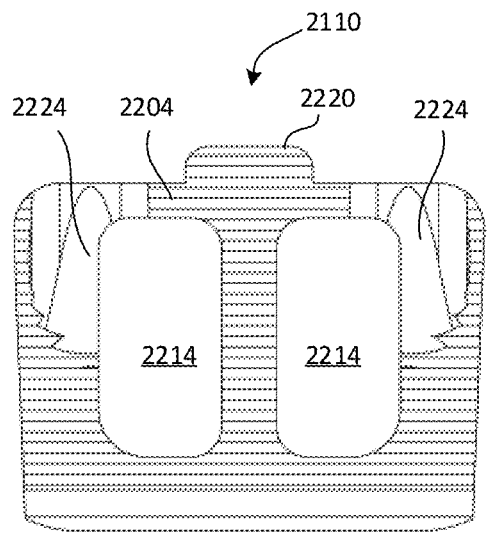
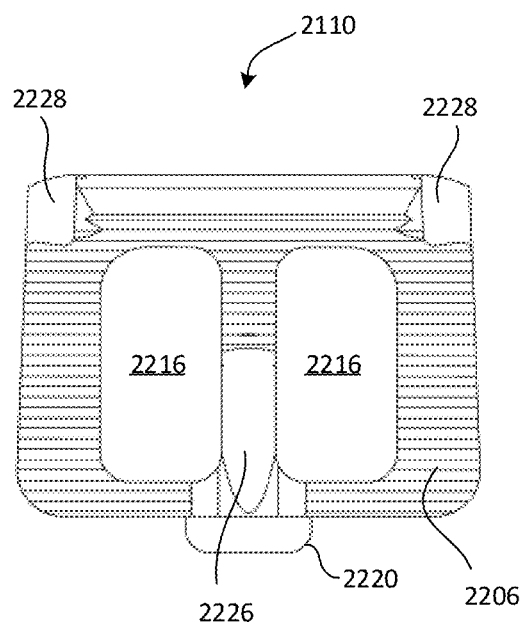
Fig. 16C                Fig. 16D

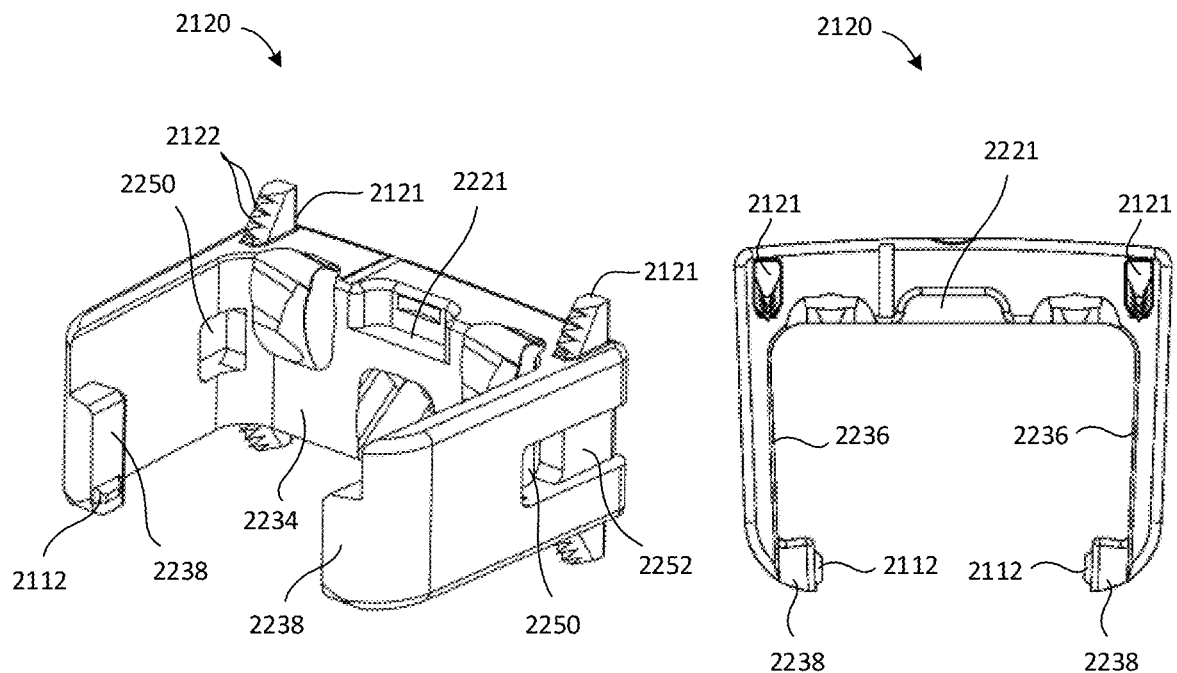
*Fig. 17A*    *Fig. 17B*
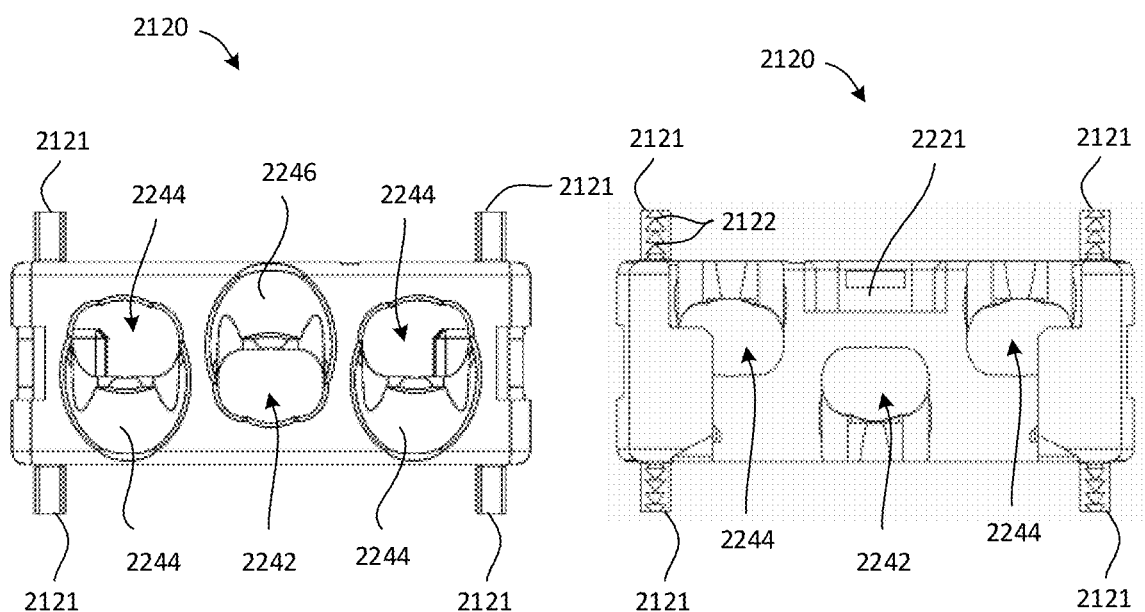
*Fig. 17C*    *Fig. 17D*

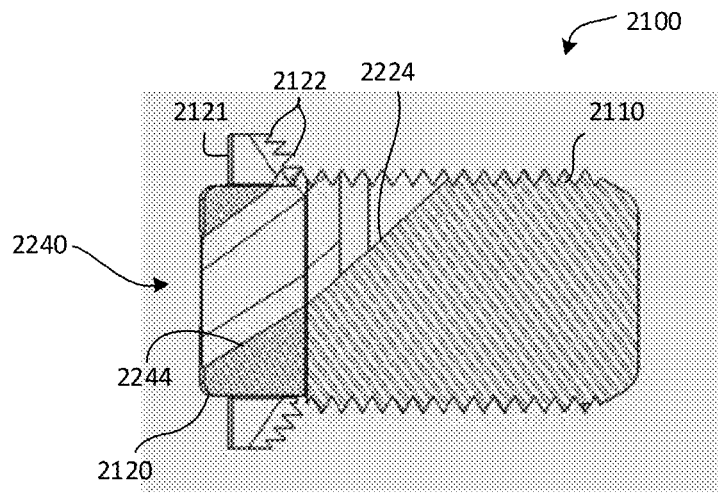
Fig. 22A
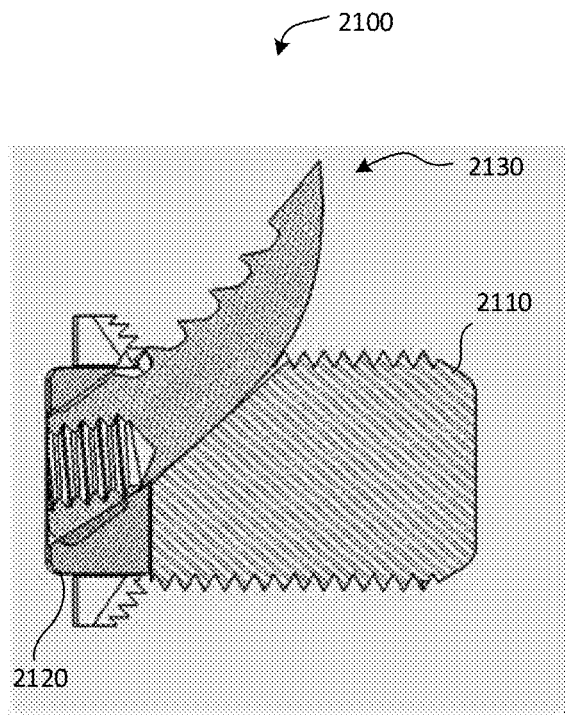 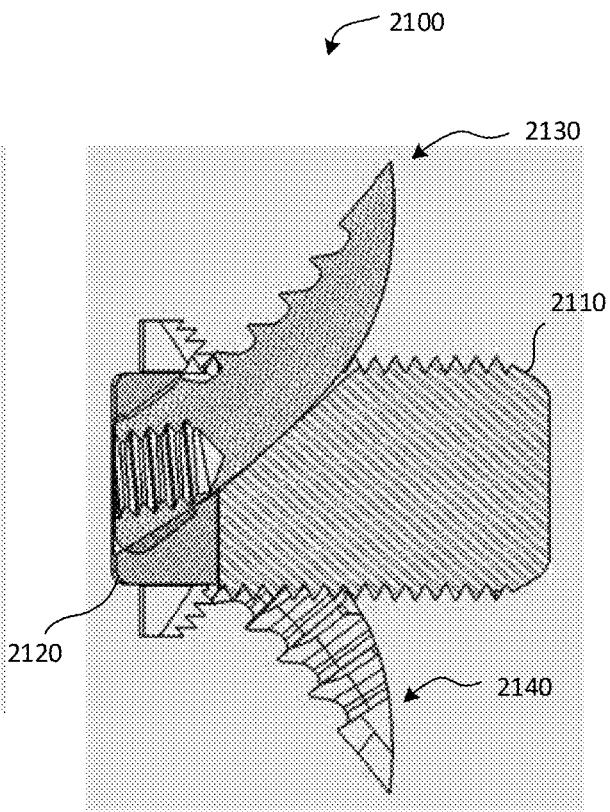
Fig. 22B          Fig. 22C

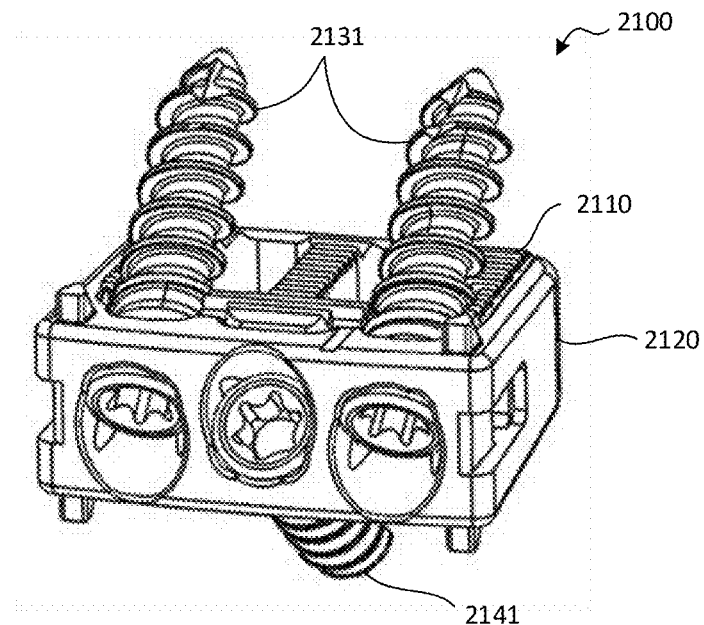
*Fig. 34A*
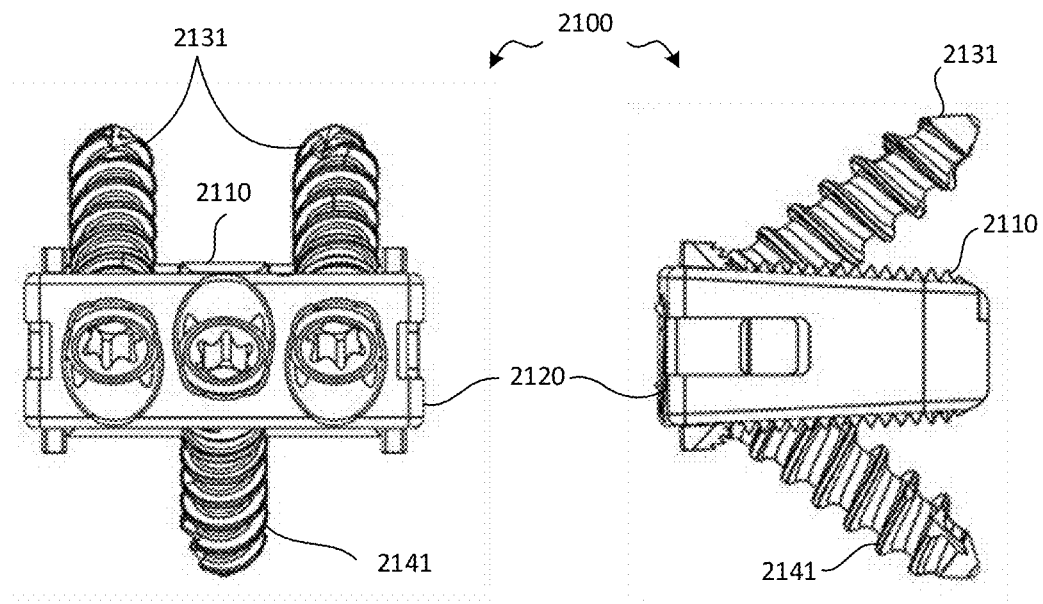
*Fig. 34B*  *Fig. 34C*

INTERBODY SPACER AND BONE PLATE ASSEMBLY

CROSS-REFERENCE TO RELATED APPLICATIONS

The present application is a continuation of U.S. patent application Ser. No. 16/025,935 filed on Jul. 2, 2018, entitled INTERBODY SPACER AND BONE PLATE ASSEMBLY, which claims the benefit of U.S. Provisional Patent Application Ser. No. 62/527,035, entitled INTERBODY SPACER AND BONE PLATE ASSEMBLY, which was filed on Jun. 30, 2017. The above-referenced applications are incorporated by reference herein as though set forth in its entirety.

TECHNICAL FIELD

The present disclosure relates to surgical devices, systems, and methods. More specifically, the present disclosure relates to orthopedic spinal surgical devices, systems, and methods utilizing a bone plate coupled to an interbody spacer and at least one fastener in order to stabilize a joint between a superior vertebra and an inferior vertebra.

BACKGROUND

Spinal fixation implants are often used to immobilize, stabilize, and/or fuse spinal joints between a superior vertebra and an inferior vertebra. Spinal fixation implants may help to speed up and promote fusion of spinal joints to treat spinal deformities and instabilities in the cervical, thoracic, lumbar, and/or sacral regions of the spine. Example spinal maladies which may require spinal fusion may include: spondylolisthesis; degenerative disc disease (DDD); trauma; excessive scoliosis, kyphosis, or lordosis; spinal stenosis; spinal tumors; pseudoarthrosis; a failed previous fusion surgery, etc.

Interbody spacers may be implanted using techniques such as Anterior Lumbar Interbody Fusion (ALIF), Posterior Lumbar Interbody Fusion (PLIF), or Transforaminal Lumbar Interbody Fusion (TLIF) surgical techniques.

Interbody spacers may be placed in the intervertebral space between adjacent vertebrae of the spine and an exterior bone plate may also be used to help stabilize adjacent vertebrae while fusion occurs. The interbody spacers and/or associated exterior bone plates should have sufficient structural integrity to withstand the stress of maintaining an intervertebral space during the fusion process in order to stay firmly in place while bone fusion occurs.

Robust and efficient spinal fixation implants, systems, and methods are desired to help lessen risks associated with spinal fixation procedures, promote better outcomes for patients, decrease costs, and increase efficiencies in associated surgical techniques.

SUMMARY

The various systems and methods of the present disclosure have been developed in response to the present state of the art, and in particular, in response to the problems and needs in the art that have not yet been fully solved by currently available technology.

In some embodiments, an implant for stabilizing a joint between a superior vertebra and an inferior vertebra may include a plate member that has an anterior end plate with an anterior surface, at least one superior fastener aperture formed in the anterior end plate, and at least one inferior fastener aperture formed in the anterior end plate. The implant may also include an interbody spacer that has a posterior end, an anterior end configured to engage the posterior surface of the anterior end plate, a superior bone-facing surface extending between the anterior end and the posterior end of the interbody spacer, the superior bone-facing surface having at least one superior bone-engagement aperture, and an inferior bone-facing surface extending between the anterior end and the posterior end of the interbody spacer, the inferior bone-facing surface having at least one inferior bone-engagement aperture. The implant may also include at least one superior fastener sized to pass through the at least one superior fastener aperture, through a first interior space of the interbody spacer, through the at least one superior bone-engaging aperture, and into a superior vertebra to anchor within the superior vertebra, as well as, at least one inferior fastener sized to pass through the at least one inferior fastener aperture, through a second interior space of the interbody spacer, through the at least one inferior bone-engaging aperture, and into an inferior vertebra to anchor within the inferior vertebra. The at least one superior fastener and the at least one inferior fastener may be spikes that include a proximal end, a distal end, and a shank extending longitudinally between the proximal end and the distal end. The shank may include a smooth surface extending along a proximal-distal length of the shank and a plurality of bone-engagement fins arranged along a majority of the proximal-distal length of the shank. The plurality of bone-engagement fins may extend away from a longitudinal center of the shank, and each of the plurality of bone-engagement fins may occupy more than half, but less than all, of a perimeter of an associated cross-section of the shank taken perpendicular to the smooth surface of the shank.

In other embodiments, an apparatus for stabilizing a joint between a superior vertebra and an inferior vertebra may include a plate member that has an anterior end plate with an anterior surface, at least one superior fastener aperture formed in the anterior end plate, and at least one inferior fastener aperture formed in the anterior end plate. The implant may also include an interbody spacer that has a posterior end, an anterior end configured to engage the posterior surface of the anterior end plate, a superior bone-facing surface extending between the anterior end and the posterior end of the interbody spacer, the superior bone-facing surface having at least one superior bone-engagement aperture, and an inferior bone-facing surface extending between the anterior end and the posterior end of the interbody spacer, the inferior bone-facing surface having at least one inferior bone-engagement aperture. The implant may also include at least one superior fastener sized to pass through the at least one superior fastener aperture, through a first interior space of the interbody spacer, through the at least one superior bone-engaging aperture, and into a superior vertebra to anchor within the superior vertebra, as well as, at least one inferior fastener sized to pass through the at least one inferior fastener aperture, through a second interior space of the interbody spacer, through the at least one inferior bone-engaging aperture, and into an inferior vertebra to anchor within the inferior vertebra. The at least one superior fastener and the at least one inferior fastener may be spikes that include a proximal end, a distal end, and a shank extending longitudinally between the proximal end and the distal end. The shank may include a smooth surface extending along a proximal-distal length of the shank, the smooth surface having a convex curvature extending along the proximal-distal length of the shank. The shank may also include a plurality of bone-engagement fins extending away from a longitudinal center of the shank.

In yet other embodiments, an assembly for stabilizing a joint between a superior vertebra and an inferior vertebra may include a plate member that has an anterior end plate with an anterior surface, at least one superior fastener aperture formed in the anterior end plate, and at least one inferior fastener aperture formed in the anterior end plate. The implant may also include an interbody spacer that has a posterior end, an anterior end configured to engage the posterior surface of the anterior end plate, a superior bone-facing surface extending between the anterior end and the posterior end of the interbody spacer, the superior bone-facing surface having at least one superior bone-engagement aperture, and an inferior bone-facing surface extending between the anterior end and the posterior end of the interbody spacer, the inferior bone-facing surface having at least one inferior bone-engagement aperture. The implant may also include at least one superior fastener sized to pass through the at least one superior fastener aperture, through a first interior space of the interbody spacer, through the at least one superior bone-engaging aperture, and into a superior vertebra to anchor within the superior vertebra, as well as, at least one inferior fastener sized to pass through the at least one inferior fastener aperture, through a second interior space of the interbody spacer, through the at least one inferior bone-engaging aperture, and into an inferior vertebra to anchor within the inferior vertebra. The at least one superior fastener and the at least one inferior fastener may be spikes that include a proximal end, a distal end, and a shank extending longitudinally between the proximal end and the distal end. The shank may include a smooth surface extending along a proximal-distal length of the shank and a plurality of bone-engagement fins coupled to the shank and extending away from a longitudinal center of the shank. The plurality of bone-engagement fins may have a plurality of apexes that cooperate to define a major diameter that tapers from the proximal end toward the distal end. The bone-engagement fins may further define troughs between adjacent bone-engagement fins that cooperate to define a minor diameter that tapers from the proximal end toward the distal end of the shank.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

FIGS. 1A-C are perspective, anterior elevation, and lateral elevation views, respectively, of an assembly for stabilizing a spinal joint, according to one embodiment of the present disclosure;

FIGS. 4A-C are perspective views of the assembly of FIGS. 1A-C depicting various stages of fastener deployment;

FIG. 9A depicts a perspective view of a fastener, according to one embodiment of the present disclosure; FIG. 9B depicts a perspective view of a fastener, according to another embodiment of the present disclosure; and FIG. 9C depicts an exploded view of the fastener of FIG. 9B;

FIGS. 12A-C depict a fastener with an expandable configuration, according to another embodiment of the present disclosure;

FIGS. 14A-C are perspective, anterior elevation, and lateral elevation views, respectively, of an assembly for stabilizing a spinal joint, according to another embodiment of the present disclosure;

FIGS. 16A-D illustrate various views of the interbody spacer utilized in the assembly shown in FIGS. 14A-C;

FIGS. 17A-D illustrate various views of the plate member utilized in the assembly shown in FIGS. 14A-C;

FIGS. 22A-C are section views, along the sagittal plane, of the assembly of FIGS. 14A-C during various stages of assembly;

FIGS. 34A-C are perspective, anterior elevation, and lateral elevation views, respectively, of the assembly of FIGS. 14A-C utilizing bone screws;

Figure 2:
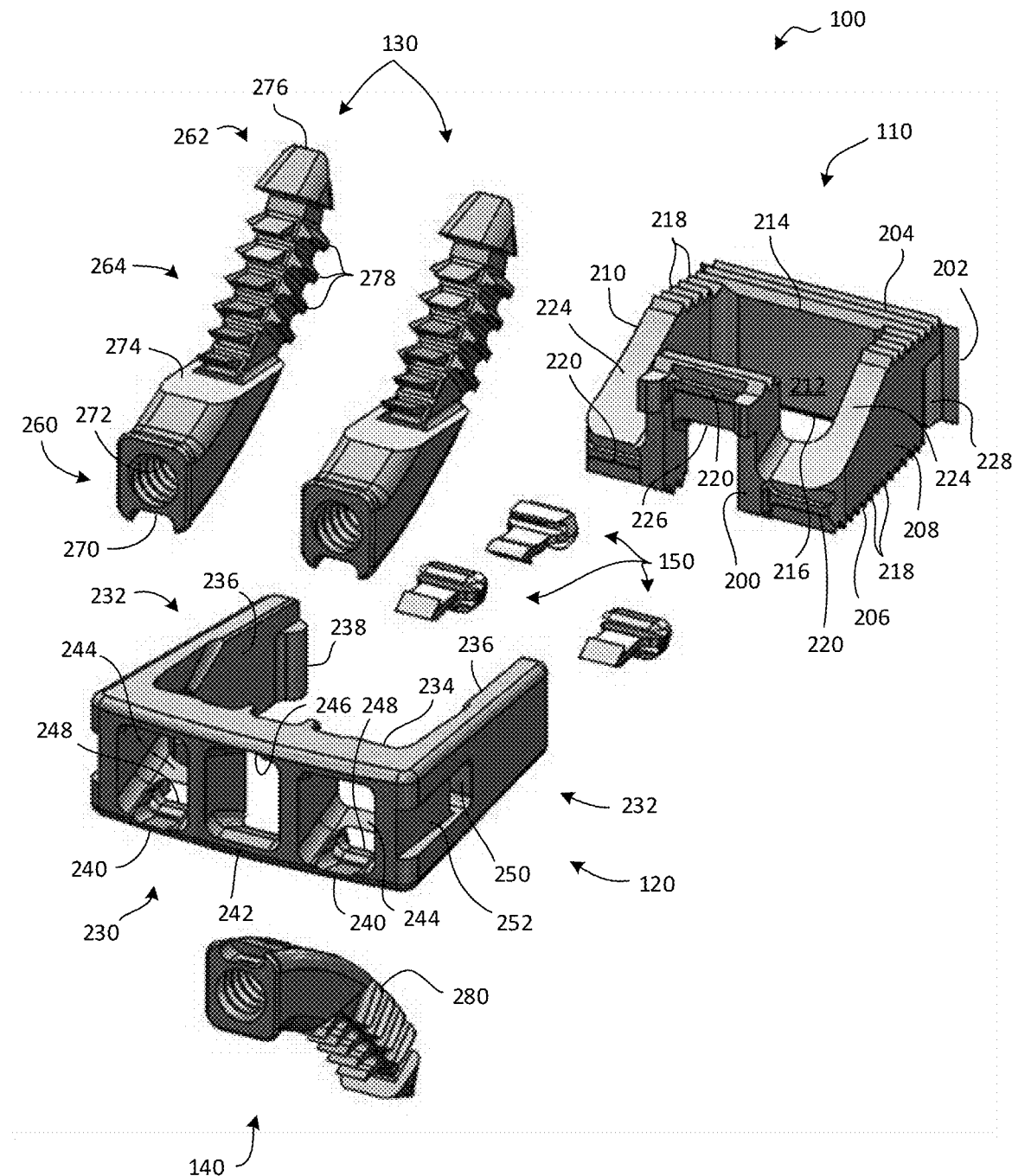
FIG. 2 is an exploded view of the assembly of FIGS. 1A-1C.

It is to be understood that the drawings are for purposes of illustrating the concepts of the disclosure and are not to scale. Furthermore, the drawings illustrate exemplary embodiments and do not represent limitations to the scope of the disclosure.

DETAILED DESCRIPTION

Exemplary embodiments of the disclosure will be best understood by reference to the drawings, wherein like parts are designated by like numerals throughout. It will be readily understood that the components of the disclosure, as generally described and illustrated in the Figures herein, could be arranged and designed in a wide variety of different configurations. Thus, the following more detailed description of the embodiments of the apparatus, systems, and methods, as represented in the Figures, is not intended to limit the scope of the disclosure, as claimed, but is merely representative of exemplary embodiments of the disclosure.

FIGS. 1A, 1B, and 1C are perspective, anterior elevation, and lateral elevation views, respectively, of an assembly 100 according to one embodiment. The assembly 100 may be designed to stabilize a joint between a superior vertebra and an inferior vertebra. Specifically, the assembly 100 may perform the functions normally carried out by an interbody spacer and a bone plate, particularly for a cervical joint. Thus, as embodied in FIGS. 1A through 1C, the assembly 100 may have an interbody spacer 110, a bone plate or plate member 120, two superior fasteners 130, an inferior fastener 140, and three locking clips 150 (two for the superior fasteners 130 and one for the inferior fastener 140). The configuration and operation of these components will be further described in connection with FIG. 2.

FIG. 2 is a section view of the assembly 100 of FIGS. 1A through 1C, according to one embodiment. The interbody spacer 110 and the bone plate 120 may be complimentarily shaped so that they can be coupled together (for example, via snap fitting), and then inserted together into the intervertebral space. The interbody spacer 110 and the bone plate 120 may then be secured to the superior vertebra and the inferior vertebra through the use of the superior fasteners 130 and the inferior fastener 140. The locking clips 150 may operate to prevent the superior fasteners and the inferior fastener 140 from "backing out," or withdrawing over time, from the superior and inferior vertebrae, respectively.

The interbody spacer 110 may have an anterior end 200, a posterior end 202, a superior bone-facing surface 204, and an inferior bone-facing surface 206. These elements are named according to the orientation in which the interbody spacer 110 will be inserted into the intervertebral space. The interbody spacer may also have a left lateral side 208 and a right lateral side 210. The interbody spacer 110 may define an interior cavity 212 bounded by a superior bone-engagement aperture 214 defined in the superior bone-facing surface 204, and an inferior bone-engagement aperture 216 defined in the inferior bone-facing surface 206. The interior cavity 212 may have a size and shape suited to retention of bone graft or other materials suitable for encouraging formation of a column of bone that connects the superior vertebra and the inferior vertebra together.

The superior bone-facing surface 204 and the inferior bone-facing surface 206 may each have teeth 218 that engage the superior vertebra and the inferior vertebra to help keep the interbody spacer 110 in place relative to the superior vertebra and the inferior vertebra as the bone column forms. The anterior end 200 may have engagement features 220 that engage the bone plate 120 and/or the locking clips 150 in order to help keep the interbody spacer 110 in place relative to the bone plate 120 and the locking clips 150. The engagement features 220 may, for example, be ridges that abut the locking clips 150 to keep the locking clips 150 in place between the engagement features 220 and corresponding engagement features 248 of the bone plate 120.

The anterior end 200 and the superior bone-facing surface 204 may further be shaped to define superior ramps 224, one at the left lateral side 208 and one at the right lateral side 210. The superior ramps 224 may extend superiorly as they extend posteriorly, thereby redirecting the superior fasteners 130 from a posterior trajectory to a superior trajectory suitable for piercing and anchoring in the vertebral body of the superior vertebra, as will be shown and described subsequently. Similarly, the anterior end 200 and the inferior bone-facing surface 206 may be further shaped to define an inferior ramp 226, which may extend inferiorly as it extends posteriorly, thereby redirecting the inferior fastener 140 from a posterior trajectory to an inferior trajectory suitable for piercing and anchoring in the vertebral body of the inferior vertebra, as will also be shown and described subsequently.

The left lateral side 208 and the right lateral side 210 may each have a recess 228. The recesses 228 may facilitate engagement of the bone plate 120 with the interbody spacer 110. The bone plate 120 may be secured to the interbody spacer 110 prior to insertion of the interbody spacer 110 and bone plate 120 into the intervertebral space.

In some embodiments, the assembly 100 may be implanted between two vertebrae of the cervical spine, from along an anterior approach. The terms "superior," "inferior," "anterior," "posterior," "medial," and "lateral" are used in this description with reference to such an embodiment. In such an implementation, the bone plate 120 may be an "anterior bone plate." However, those of skill in the art will recognize that the systems and methods disclosed herein are not limited to such an implantation site, or to such an approach.

The bone plate 120 may have an anterior end 230 and two posterior extensions 232 that extend posteriorly from the anterior end 230. The anterior end 230 may define a posterior surface 234 that abuts and engages the anterior end 200 of the interbody spacer 110. Similarly, each of the posterior extensions 232 may define an interior surface 236 that abuts and engages the corresponding one of the left lateral side 208 and the right lateral side 210 of the interbody spacer 110. Further, each of the posterior extensions 232 may have an engagement feature designed to enter and engage one of the recess 228 of the left lateral side 208 and the right lateral side 210.

Specifically, as embodied in FIG. 2, the engagement features may be nubs 238 that extend medially. The nubs 238 may be rounded such that they facilitate assembly of the interbody spacer 110 and the bone plate 120 from along an anterior-posterior direction. For example, the interbody spacer 110 and the bone plate 120 may be assembled by aligning the interbody spacer 110 and the bone plate at the same superior/inferior level, with the bone plate 120 anterior to the interbody spacer 110, and then moving the bone plate 120 posteriorly into engagement with the interbody spacer 110. The nubs 238 may abut the anterior end 200 of the interbody spacer 110, and their rounded shape may cause the posterior extensions 232 to spread apart to receive the interbody spacer 110 between the posterior extensions 232. The bone plate 120 may slide posteriorly along the interbody spacer 110 until the nubs 238 enter the recesses 228 of the left lateral side 208 and the right lateral side 210 of the interbody spacer. Thus, the bone plate 120 may be snap fitted to the interbody spacer 110.

In alternative embodiments, different assembly modes may be used. For example, the interbody spacer 110 may be positioned directly superior to the bone plate 120, and then moved inferiorly until the interbody spacer 110 is positioned between the posterior extensions 232 of the bone plate 120. The nubs 238 may enter the recesses 228 of the left lateral side 208 and the right lateral side 210 along a superior trajectory, causing the bone plate 120 to engage and retain the interbody spacer 110.

The anterior end 230 of the bone plate 120 may be shaped to define superior fastener apertures 240 proximate each of the posterior extensions 232, and an inferior fastener aperture 242 between the superior fastener apertures 240. The superior fastener apertures 240 and the inferior fastener aperture 242 may be sized to receive the superior fasteners 130 and the inferior fastener 140, respectively. The anterior end 230 of the bone plate 120 may further be shaped to define ramps 244 adjacent to the superior fastener apertures 240, and a ramp 246 adjacent to the inferior fastener aperture 242.

In the embodiment of FIGS. 1A through 4C, there are two superior fasteners 130 and one inferior fastener 140. In alternative embodiments, any combination of fasteners may be used. For example, there may be two inferior fasteners and one superior fastener, one of each type, two of each type, or the like. Further, in some embodiments, more than four fasteners may be used, with any combination of superior and inferior fasteners.

Further, the interbody spacer 110 and the bone plate 120 may, in some embodiments, be used independently of each other. For example, the interbody spacer 110 may be implanted between two adjacent vertebrae without the use of an anterior bone plate, and/or without the use of fasteners. In some embodiments, the interbody spacer 110 may, without the use of the bone plate 120, the superior fasteners 130, and/or the inferior fastener 140, satisfy the reimbursement requirements for interbody spacers, such as those associated with the OBP reimbursement code.

Further to the foregoing, the bone plate 120 may also be used with the superior fasteners 130 and/or the inferior fastener 140, independently of the use of the interbody spacer 110. The bone plate 120 may be implanted between two adjacent vertebrae, with the posterior extensions 232 extending posteriorly between the central portions of the vertebral bodies. The ramps 244 and the ramp 246 may be used to redirect the superior fasteners 130 and the inferior fastener 140 from posterior trajectories to superior and inferior trajectories, respectively, such that the superior fasteners 130 and the inferior fastener 140 anchor in the adjacent vertebral bodies to secure the bone plate 120 in place without the interbody spacer 110. In some embodiments, the bone plate 120, superior fasteners 130, and inferior fastener 140 may, without the use of the interbody spacer 110, satisfy the reimbursement requirements for anterior bone plates, such as those associated with the KWQ reimbursement code.

Yet further to the foregoing, the interbody spacer 110 and the bone plate 120 may be assembled and implanted together and may cooperate to facilitate implantation of the superior fasteners 130 and the inferior fastener 140, as will be discussed below. In some embodiments, the interbody spacer 110, the bone plate 120, the superior fasteners 130, and the inferior fastener 140 may cooperate to satisfy the reimbursement requirements for a system including an anterior bone plate and an interbody spacer, such as those associated with the OVE reimbursement code.

When the interbody spacer 110 and the bone plate 120 are assembled together, the ramps 244 may align with the superior ramps 224 of the interbody spacer 110 to define two continuous superiorly-angled ramp surfaces extending from the bone plate 120 to the interbody spacer 110. Similarly, when the interbody spacer 110 and the bone plate 120 are assembled together, the ramp 246 may align with the inferior ramp 226 of the interbody spacer 110 to define one continuous inferiorly-angled ramp surface extending from the bone plate 120 to the interbody spacer 110.

The bone plate 120 may have features that facilitate gripping of the bone plate 120 by an inserter. Specifically, in the embodiment of FIG. 2, each of the posterior extensions 232 of the bone plate 120 may have a window 250 extending therethrough, and a groove 252 extending from the anterior end 230 of the bone plate 120 to the window 250. An inserter may have arms that engage the windows 250 via the grooves 252, as will be shown and described subsequently.

In some embodiments, the inferior fastener 140 may have the same configuration as the superior fasteners 130. Each of the superior fasteners 130 may have a proximal end 260, a distal end 262, and a shank 264 extending between the proximal end 260 and the distal end 262.

Each proximal end 260 may have a retention feature 270 that facilitates retention of the proximal end 260 at a desired position relative to the bone plate 120, and a hole 272 that may be used for supplemental retention and/or withdrawal of the superior fasteners 130 and/or the inferior fastener 140 from the bone plate 120 for revision. More specifically, the hole 272 may have female threads that can receive male threads of a set screw to help keep the fastener in place relative to the bone plate 120 and the interbody spacer 110, or the male threads of a removal tool designed to remove the fastener from the bone plate 120 and the interbody spacer 110. A shoulder 274 may separate the proximal end 260 from the shank 264.

The distal end 262 may have a sharpened tip 276 shaped to penetrate bone. The shank 264 may have a plurality of bone-engagement fins 278 that engage the bone and help prevent unintended withdrawal of the superior fasteners 130 and the inferior fastener 140 from the bone. The bone-engagement fins 278 may each have a thickness selected to enable the bone-engagement fins 278 to bend toward the proximal end 260 during insertion of the superior fasteners 130 and inferior fastener 140 into the bone. The bone-engagement fins 278 may then set themselves in the bone in a barb-like manner in response to force tending to urge the superior fasteners 130 and the inferior fastener 140 to pull out of the bone. The shank 264 may further have a smooth, convex surface 280 that slides along the superior ramps 224, the inferior ramp 226, the ramps 244, and/or the ramp 246.

The locking clips 150 may be used to further retain the superior fasteners 130 and the inferior fastener 140 in place, relative to the bone plate 120. The configuration and operation of the locking clips 150 will be further described in connection with FIGS. 8A and 8B.

The interbody spacer 110, the bone plate 120, the superior fasteners 130, the inferior fastener 140, and the locking clips 150 may be made from various bio-compatible materials. Metals, plastics, ceramics, and combinations thereof may be used. In some embodiments, some components may be made of metal while others are plastic. For example, in one embodiment, the interbody spacer 110 may be formed of a biocompatible polymer such as PEEK, and the bone plate 120 may be made of a biocompatible metal such as Titanium. The superior fasteners 130 and the inferior fastener 140 may be made of Titanium, polymers, and/or combinations thereof. The locking clips 150 may also be made of Titanium, if desired.

The curved shapes of the superior fasteners 130 and the inferior fastener 140, in combination with the superior ramps 224, the inferior ramp 226, the ramps 244, and the ramp 246 may allow the superior fasteners 130 and the inferior fastener 140 to be inserted and urged along a posterior direction to move superiorly and inferiorly, respectively, into the superior vertebra and the inferior vertebra. This will be further described in connection with FIGS. 3A through 7B, as follows.

Figure 3A:
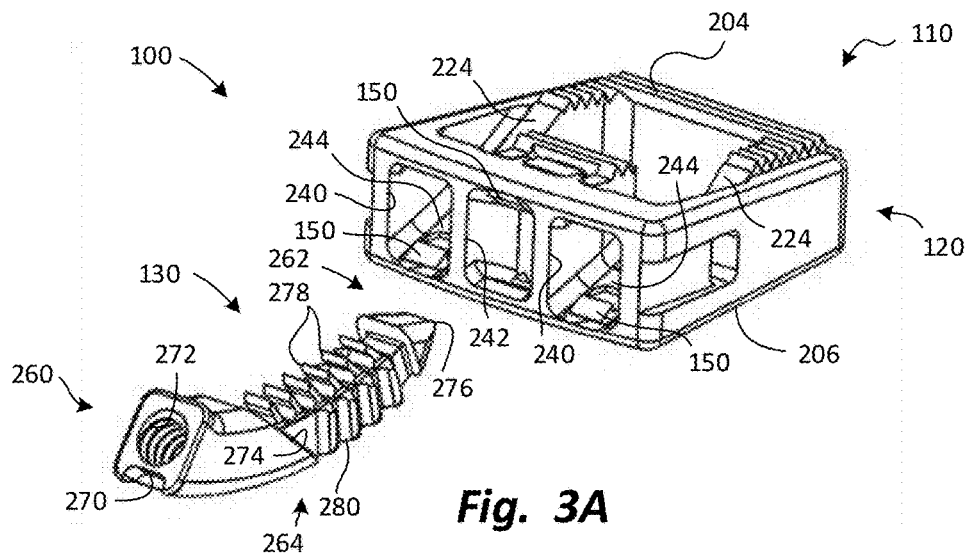
FIGS. 3A-C are perspective views of the assembly of FIGS. 1A-C depicting various stages of fastener insertion.
Figure 3B:
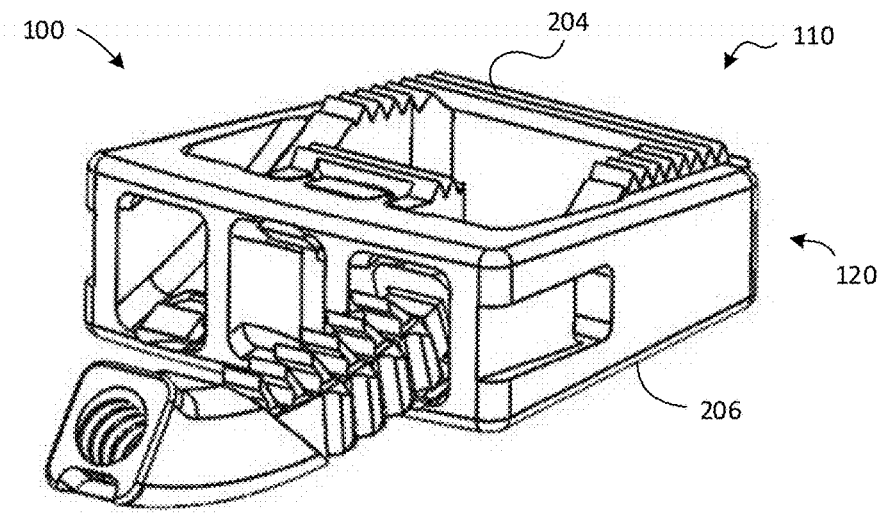
Figure 3C:
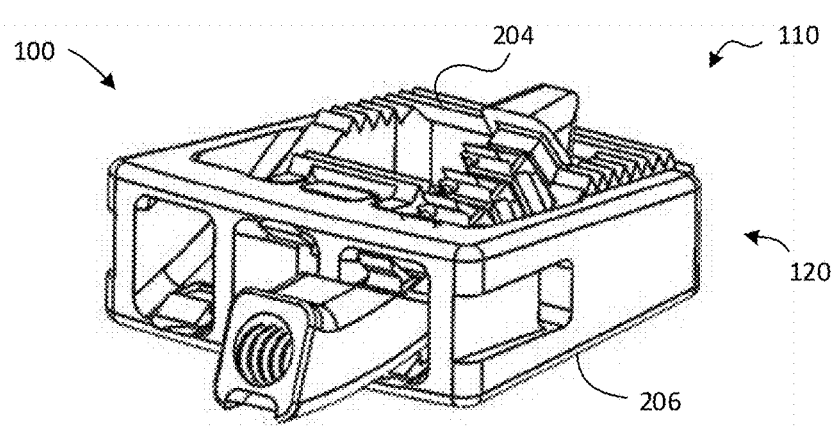

FIGS. 3A, 3B, and 3C depict the interbody spacer 110, the bone plate 120, and one of the superior fasteners 130, in various stages of fastener insertion, according to one embodiment. In FIG. 3A, one of the superior fasteners 130 has been aligned with one of the superior fastener apertures 240 of the anterior end 230 of the bone plate 120. The distal end 262 of one of the superior fasteners 130 may be inserted along a posterior trajectory into one of the superior fastener apertures 240, such that the convex surface 280 engages the corresponding one of the ramps 244 of the bone plate 120. This is the position depicted in FIG. 3B.

As mentioned previously, when the interbody spacer 110 and the bone plate 120 are secured together, the superior ramps 224 and the ramps 244 may align with each other to define two continuous, superiorly-oriented ramps traversing the bone plate 120 and the interbody spacer 110. Similarly, the inferior ramp 226 and the ramp 246 may align with each other to define one continuous, inferiorly-oriented ramp traversing the bone plate 120 and the interbody spacer 110. Thus, further posterior motion of the superior fasteners 130 may cause the convex surface 280 of each of the superior fasteners 130 to move from the ramps 244 of the bone plate 120 to the adjoining superior ramps 224 of the interbody spacer 110. This motion along the ramps 244 and the superior ramps 224 may redirect the distal end 262 of each of the superior fasteners 130 from the posterior trajectory in which the superior fasteners 130 entered the bone plate 120, to a superior trajectory by which the superior fasteners 130 are able to penetrate the vertebral body co of the superior vertebra. This is depicted in FIG. 3C.

FIGS. 4A, 4B, and 4C depict the assembly 100, with one of the superior fasteners 130 fully inserted into the bone plate 120 and the interbody spacer 110, with both of the superior fasteners 130 inserted, and with the superior fasteners 130 and the inferior fastener 140 fully inserted, respectively. As shown, the superior fasteners 130 may be inserted into the superior fastener apertures 240 of the bone plate 120, and the inferior fastener 140 may be inserted into the inferior fastener aperture 242 of the bone plate 120. Insertion may progress until the proximal end 260 of each of the superior fasteners 130 and the inferior fastener 140 has reached, and resides within, the superior fastener apertures 240 and the inferior fastener aperture 242, respectively. In this position, the distal end 262 of each of the superior fasteners 130 and the inferior fastener 140 may be positioned well within the vertebral body of the corresponding superior or inferior vertebra.

The locking clips 150 may be used to lock the proximal end 260 of each of the superior fasteners 130 and the inferior fastener 140 in place within the superior fastener apertures 240 and the inferior fastener aperture 242, respectively, of the bone plate 120. This will be further shown and described in connection with FIGS. 8A and 8B. Further, supplemental and/or alternative retention mechanisms may be used, as will be discussed in connection with FIGS. 10A and 10B. Additional alternatives may include, but are not limited to, snap rings, tangs, secondary bone plates, wires, clips, chemical or adhesive bonds, and the like.

The superior fasteners 130 and the inferior fastener 140 need not be inserted sequentially as shown in FIGS. 4A, 4B, and 4C. Rather, the superior fasteners 130 and the inferior fastener 140 may, in some embodiments, be inserted simultaneously, as will be further shown and described in connection with FIGS. 5A through 6C, as follows.

Figure 5A:
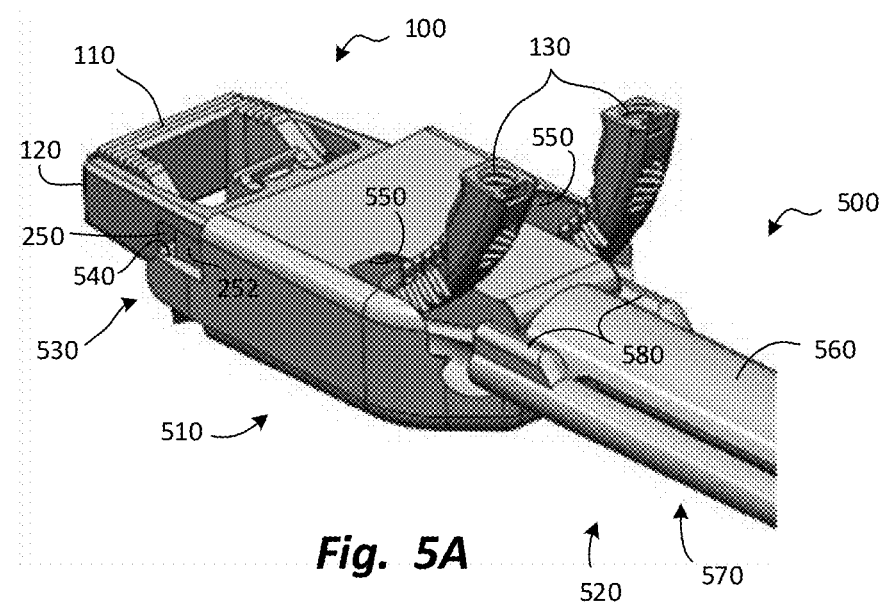
FIGS. 5A-C depict the assembly of FIGS. 1A-C coupled to an inserter, according to one embodiment of the present disclosure.
Figure 5B:
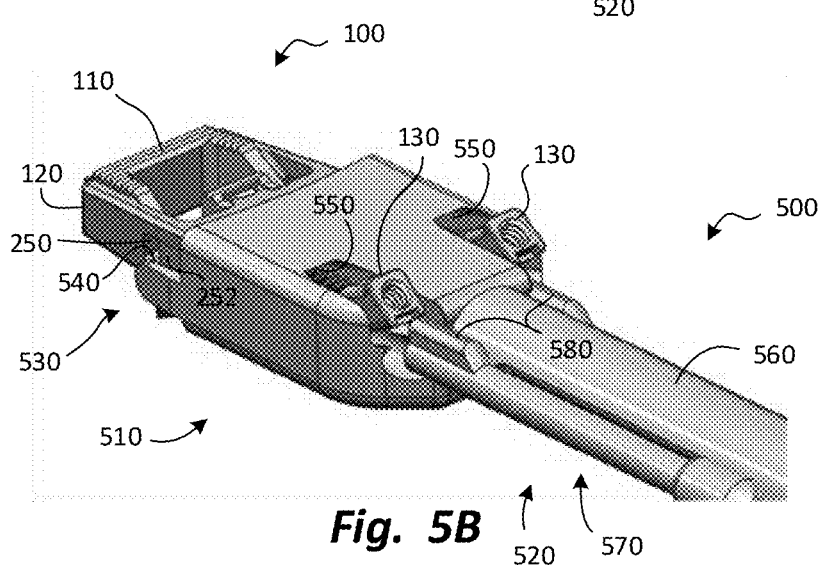
Figure 5C:
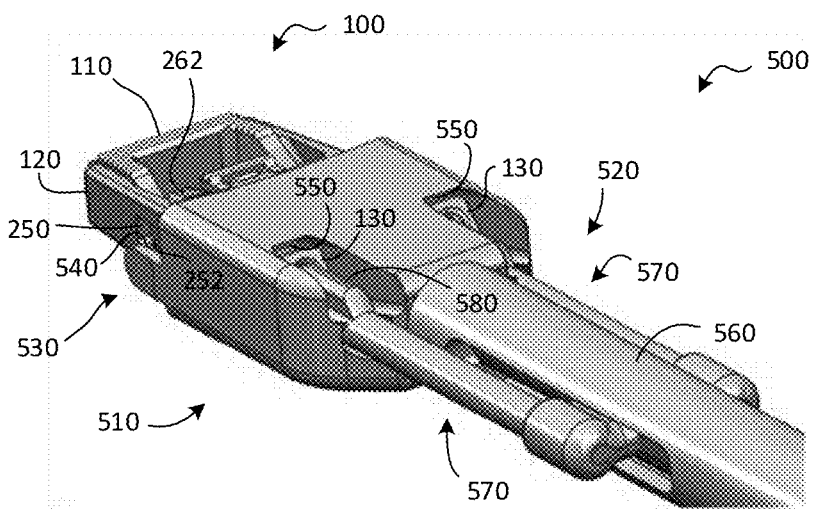

FIGS. 5A, 5B, and 5C depict the assembly 100, coupled to an inserter 500 that facilitates insertion and positioning of the assembly 100, and also aids in deployment of the superior fasteners 130 and the inferior fastener 140, according to one embodiment. The inserter 500 may have a proximal end (not shown in FIGS. 5A through 5C) and a distal end with a head 510 connected to the proximal end via a shank 520.

The head 510 may have features that help to retain the assembly 100. Specifically, the head 510 may have a pair of arms 530 that extend distally and are spaced apart to accommodate the assembly 100 between them. The arms 530 may be sized and positioned to reside in the grooves 252 of the bone plate 120 when the assembly 100 is secured to the inserter 500. The arms 530 may have inwardly-extending tabs 540 that extend into the windows 250 of the bone plate 120 when the arms 530 are positioned in the grooves 252.

The head 510 may also have three bores 550, two exiting on the superior side of the head 510, and one (not shown) exiting on the inferior side of the head 510. The bores 550 may have each have an internal ramp and/or curvature that helps the superior fasteners 130 and the inferior fastener 140 enter the superior fastener apertures 240 and the inferior fastener aperture 242, respectively, of the bone plate 120 along a posterior trajectory that arcs superiorly or inferiorly, as applicable. The superior fasteners 130 and the inferior fastener 140 may all be inserted into the proximal end of the head 510 as shown and may be oriented along arcuate trajectories by which the proximal ends 260 of the superior fasteners 130 and the inferior fastener 140 are able to swing together into a common plane as the distal ends 262 of the fasteners and the inferior fastener 140 swing superiorly and inferiorly, respectively.

According to one example, the bores 550 may have internal ramps that align with the ramps 244 and the ramp 246 of the bone plate 120. Thus, the internal ramps of the bores 550 on the left and right sides of the head 510 may cooperate with the ramps 244 of the bone plate 120 and the superior ramps 224 of the interbody spacer 110 to define two continuous, ramping surfaces. Similarly, the internal ramp of the bore 550 in the center of the head 510 may cooperate with the ramp 246 of the bone plate 120 and the inferior ramp 226 of the interbody spacer 110 to define one continuous ramping surface.

The shank 520 may have a central shaft 560 and three push rods 570. The push rods 570 may be aligned with the bores 550 of the head 510 so that two of the push rods 570 are present on either side of the central shaft 560, and the third of the push rods 570 (not shown) is within the hollow interior of the central shaft 560. Each of the push rods 570 may terminate, at its distal end, in a head 580 shaped to engage the proximal end 260 of one of the superior fasteners 130 and the inferior fastener 140, and to fit within the corresponding one of the bores 550.

In FIG. 5A, the interbody spacer 110 and the bone plate 120 have already been secured together, for example, as described previously. The locking clips 150 may be captured between the interbody spacer 110 and the bone plate 120, as will be shown and described subsequently.

The assembly 100 may be secured to the inserter 500 via engagement of the arms 530 with the windows 250 and the groove 252 of the bone plate 120, as discussed previously. This may be done, for example, by positioning the head 510 of the inserter 500 immediately anterior to the bone plate 120 and the interbody spacer 110, and then urging the head 510 to move posteriorly relative to the interbody spacer 110 and the bone plate 120. The inwardly-extending tabs 540 of the arms 530 of the head 510 may engage the grooves 252 of the bone plate 120, causing the arms 530 to flex apart. The head 510 may continue to be urged proximally until the inwardly-extending tabs 540 enter the windows 250 of the bone plate 120, and the arms 530 reside in the grooves 252 of the bone plate 120.

Once the assembly 100 (excluding the superior fasteners 130 and the inferior fastener 140) has been secured to the head 510, the assembly 100 may be positioned within the intervertebral space using the inserter 500. This may be done after retraction of the tissues surrounding the joint to be secured, and resection of the intervertebral disc.

Once the assembly 100 has been properly positioned, the distal ends 262 of the superior fasteners 130 and the inferior fastener 140 may be inserted into the bores 550 of the head 510 of the inserter 500, as depicted in FIG. 5A. The superior fasteners 130 and the inferior fastener 140 may be inserted proximally through the bores 550 until the proximal ends 260 of the superior fasteners 130 and the inferior fastener 140 are positioned in the proximal openings of the bores 550, as depicted in FIG. 5B. In the alternative, the superior fasteners 130 and/or the inferior fastener 140 may be loaded into the head 510 after assembly of the interbody spacer 110 and the bone plate 120, but prior to insertion of the interbody spacer 110 and the bone plate 120 into the intervertebral space. Thus, the superior fasteners 130 and/or the inferior fastener 140 may be positioned in the head 510 without interference from tissues surrounding the implantation site, and with less risk of accidental damage to such tissues.

Once the proximal ends 260 of the superior fasteners 130 and the inferior fastener 140 are positioned in the proximal openings of the bores 550, the push rods 570 of the shank 520 may be advanced so that the heads 580 of the push rods 570 engage the proximal ends 260 of the superior fasteners 130 and the inferior fastener 140. The inserter 500 may have a mechanism that facilitates advancement of the push rods 570 relative to the central shaft 560.

As shown in FIG. 5C, the push rods 570 may be advanced proximally until the distal ends 262 of the superior fasteners 130 and the inferior fastener 140 have moved along the ramps 244, the superior ramps 224, the ramp 246, and the inferior ramp 226, respectively, and are ready to protrude through the superior bone-facing surface 204 and the inferior bone-facing surface 206, respectively. The tips 276 of the superior fasteners 130 and the inferior fastener 140 may then be ready to pierce and enter the bone of the adjoining superior and inferior vertebral bodies.

Figure 6A:
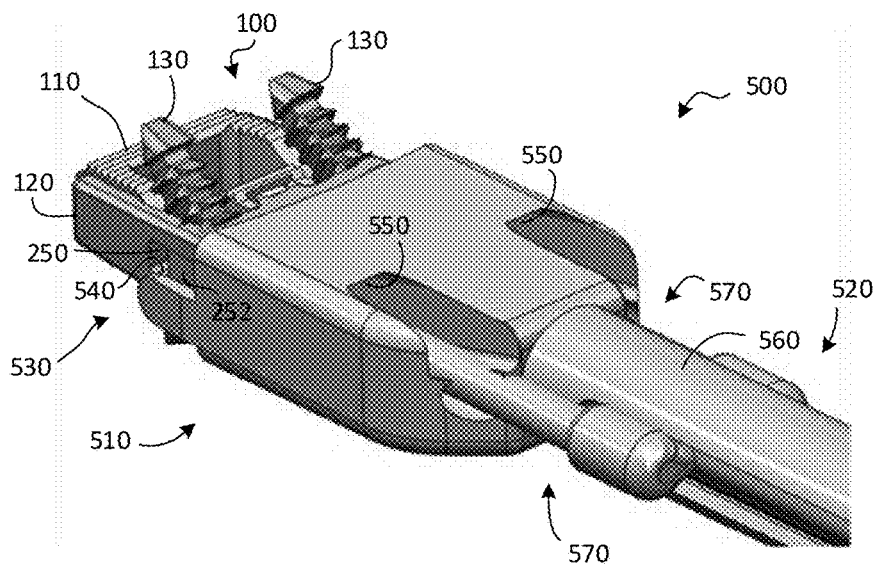
FIGS. 6A-C depict the assembly and inserter of FIGS. 5A-C with deployed fasteners.
Figure 6B:
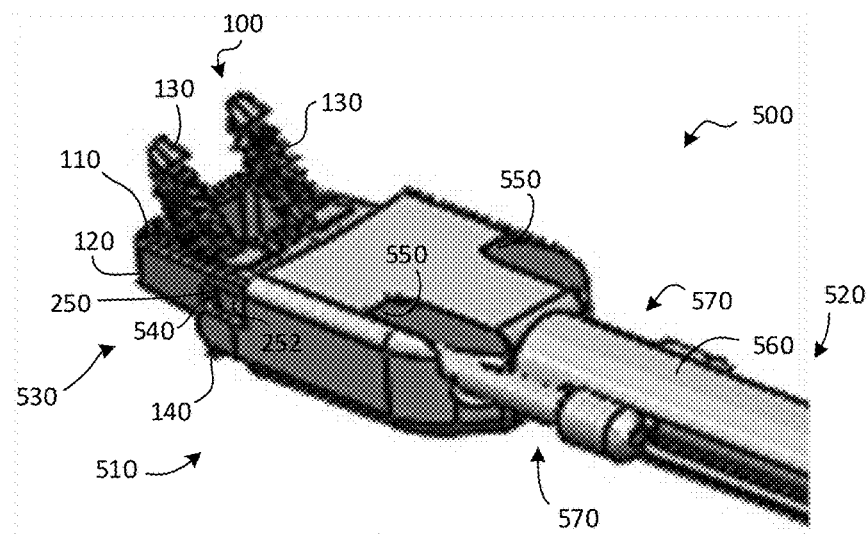
Figure 6C:
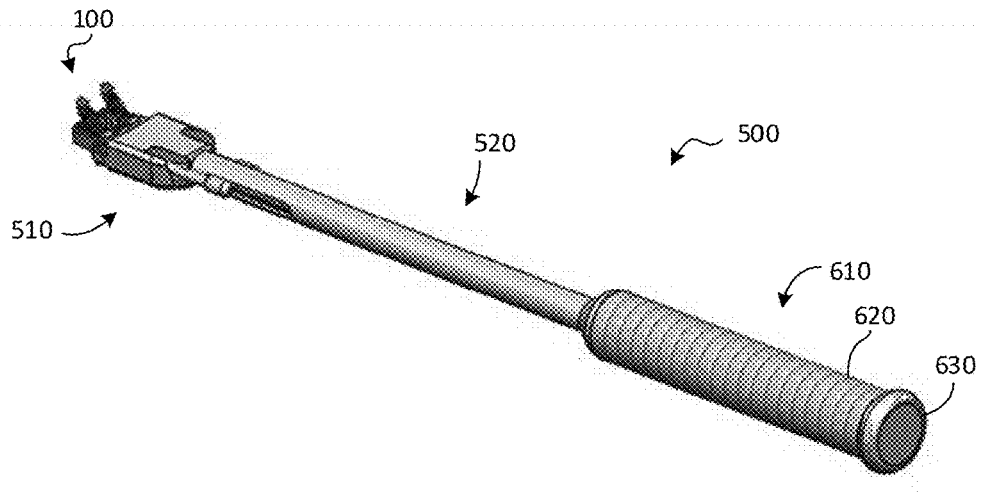

FIGS. 6A, 6B, and 6C depict the assembly 100, coupled to the inserter 500, after performance of the steps described in connection with FIG. 5C. With the superior fasteners 130 and the inferior fastener 140 positioned as in FIG. 5C, the push rods 570 may be further moved posteriorly to urge the superior fasteners 130 and the inferior fastener 140 to move along the ramps 244 and the superior ramps 224, and along the ramp 246 and the inferior ramp 226, respectively.

This further posterior motion of the superior fasteners 130 and the inferior fastener 140 may cause the tips 276 of the superior fasteners 130 to protrude through the superior bone-facing surface 204 of the interbody spacer 110 and may cause the tip 276 of the inferior fastener 140 to protrude through the inferior bone-facing surface 206 of the interbody spacer 110. The tips 276 of the superior fasteners 130 and the inferior fastener 140 may thus enter the vertebral bodies superior and inferior to the assembly 100, along with the adjoining portion of the shank 264 of each of the superior fasteners 130 and the inferior fastener 140. This is the configuration depicted in FIG. 6A.

From the configuration of FIG. 6A, the push rods 570 may be further moved posteriorly to urge the superior fasteners 130 and the inferior fastener 140 to move along the ramps 244 and the superior ramps 224, and along the ramp 246 and the inferior ramp 226, respectively, until the proximal ends 260 of the superior fasteners 130 and the inferior fastener 140 are flush with the anterior surface of the anterior end 230 of the bone plate 120, as depicted in FIG. 6B and FIG. 4C. Thus, the shank 264 of each of the superior fasteners 130 and the inferior fastener 140 may be extended fully superiorly and inferiorly, respectively, to achieve maximum purchase in the bone of the adjacent vertebral bodies. As depicted in FIG. 4C, the shoulders 274 of the superior fasteners 130 may be flush with the superior bone-facing surface 204 of the interbody spacer 110. Similarly, the shoulder 274 of the inferior fastener 140 may be flush with the inferior bone-facing surface 206 of the interbody spacer 110.

The push rods 570 may be advanced in various ways. In some embodiments, the inserter 500 may have a handle that carries a device that can be actuated to advance the push rods 570. One such embodiment is shown in FIG. 6C. As shown, the inserter 500 may have a handle 610 connected to the head 510 by the shank 520. The handle 610 may have a grip 620 and a knob 630. The grip 620 may be hollow, and the knob 630 may be coupled to the push rods 570 by an interior rod (not shown) extending through the length of the central shaft 560 and the grip 620.

When the push rods 570 are retracted, the knob 630 may be withdrawn proximally from the proximal end of the grip 620 to expose a length of the interior rod. Thus, a user, such as a surgeon, may push the knob 630 toward the grip 620 to advance the push rods 570, thereby urging the superior fasteners 130 and the inferior fastener 140 to move proximally as described previously. When the superior fasteners 130 and the inferior fastener 140 have been fully advanced as in FIGS. 6B and 6C, the knob 630 may abut the proximal end of the grip 620.

The assembly 100 may advantageously help to minimize soft tissue retraction (and thence soft tissue injury) via insertion of the superior fasteners 130 and the inferior fastener 140 along a posterior trajectory. In alternative embodiments, straight fasteners may be used, and may be inserted along other trajectories, such as superior-posterior and inferior-posterior trajectories.

With the superior fasteners 130 and the inferior fastener 140 fully advanced, the head 510 may be detached from the assembly 100. In some embodiments, the head 510 may be able to be pulled anteriorly free of the assembly 100. Due to the engagement of the superior fasteners 130 and the inferior fastener 140 with the superior and inferior vertebrae, respectively, the assembly 100 may remain lodged between the vertebrae. The anterior force on the head 510 may cause the arms 530 of the head 510 to spread, allowing the inwardly-extending tabs 540 to pull free of the windows 250 of the bone plate 120 so that the head 510 can be detached from the assembly 100. The disposition of the assembly 100 will be shown and described in connection with FIGS. 7A and 7B, as follows.

Figure 7A:
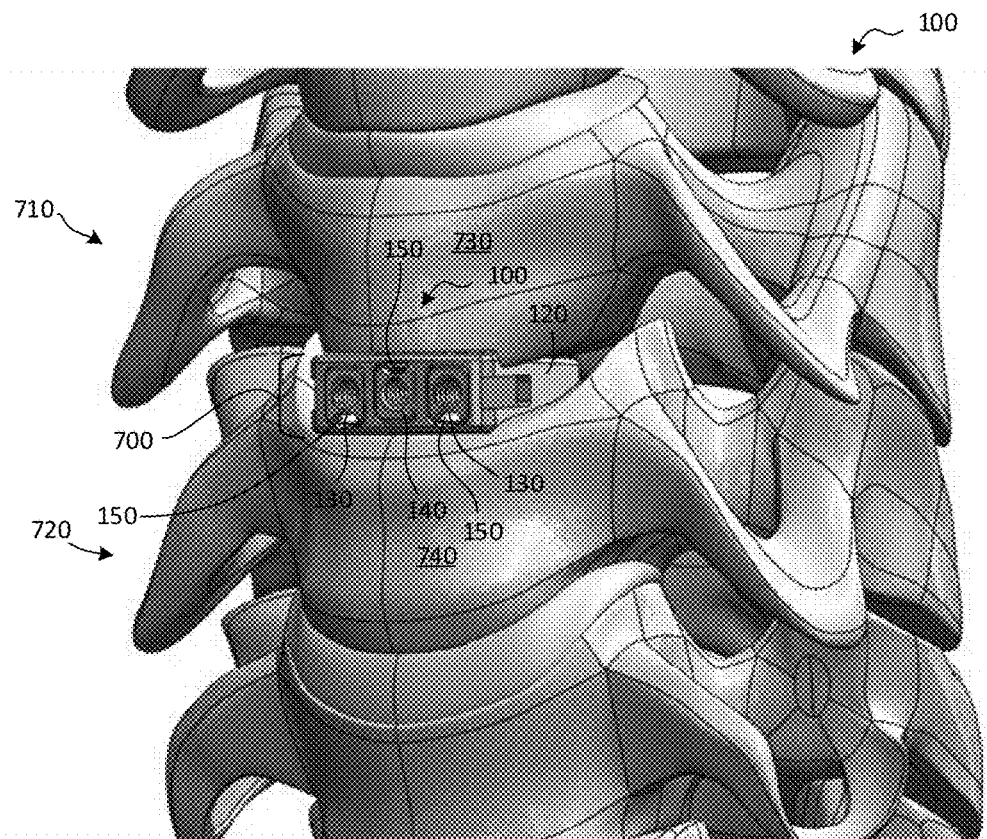
FIGS. 7A-B depict the assembly of FIGS. 1A-C implanted within an intervertebral space.
Figure 7B:
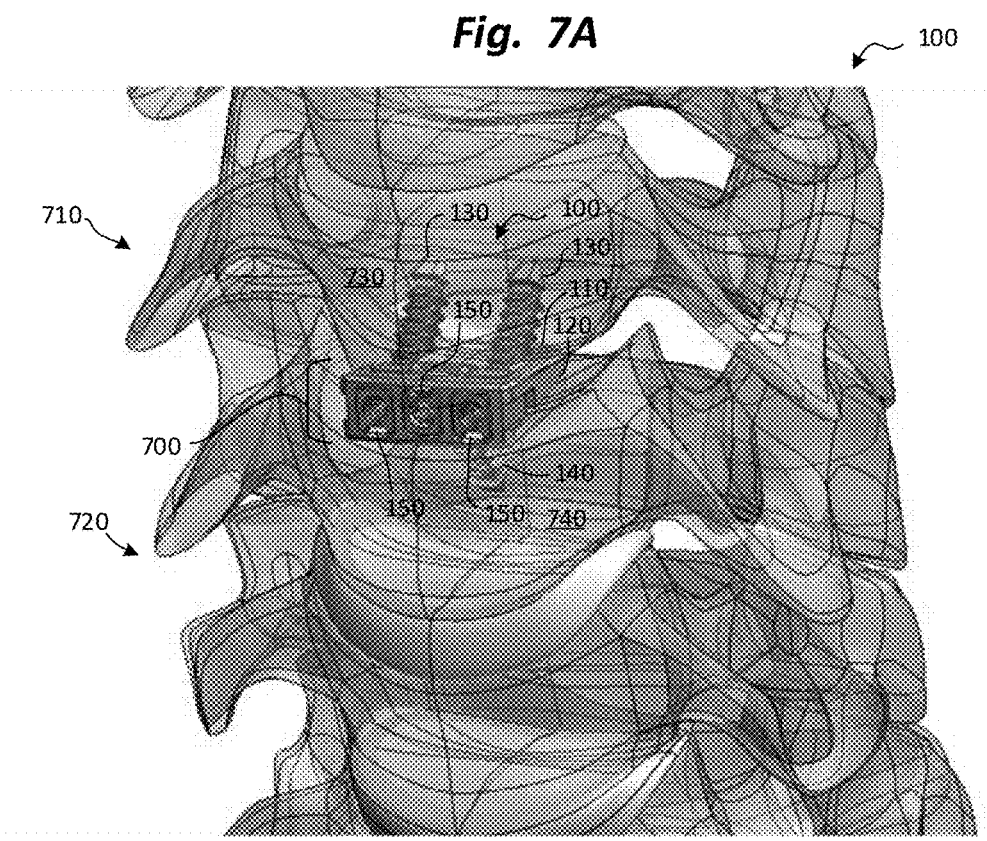

FIGS. 7A and 7B depict the assembly 100 in its fully assembled state, with the superior fasteners 130 and the inferior fastener 140 deployed to retain the assembly 100 within an intervertebral space 700 between a superior vertebra 710 and an inferior vertebra 720. As shown in FIG. 7B, the superior fasteners 130 extend into a superior vertebral body 730 of the superior vertebra 710, and the inferior fastener 140 extends into an inferior vertebral body 740 of the inferior vertebra 720.

Notably, the interbody spacer 110 and the bone plate 120 may cooperate to stabilize the joint between the superior vertebra 710 and the inferior vertebra 720. Specifically, the interbody spacer 110 may help restrict compression of the intervertebral space 700, and the bone plate 120 may help ensure that the intervertebral space 700 does not widen excessively and may help retain the interbody spacer 110 in place between the superior vertebral body 730 and the inferior vertebral body 740. As mentioned previously, bone graft or other substances may be inserted into the interior cavity 212 of the interbody spacer 110 to encourage the growth of a column of bone through the interior cavity 212, connecting the superior vertebral body 730 to the inferior vertebral body 740. The interbody spacer 110 and the bone plate 120 may keep the joint immobilized to permit growth of such a column. As mentioned previously, the interbody spacer 110 and the bone plate 120 may, in some embodiments, be used independently of each other. In such cases, the interbody spacer 110 and/or the bone plate 120 (with the superior fasteners 130 and/or the inferior fastener 140) may provide sufficient fixation, independently, to permit formation of bone to fuse the two adjacent vertebral bodies together.

The proximal ends 260 of the superior fasteners 130 and the inferior fastener 140 may advantageously be secured relative to the bone plate 120 and the interbody spacer 110 to ensure that the superior fasteners 130 and the inferior fastener 140 do not work themselves loose over time. This may be done in various ways, including through the use of the locking clips 150. The manner in which the locking clips 150 operate will be further shown and described in connection with FIGS. 8A and 8B.

Figure 8A:
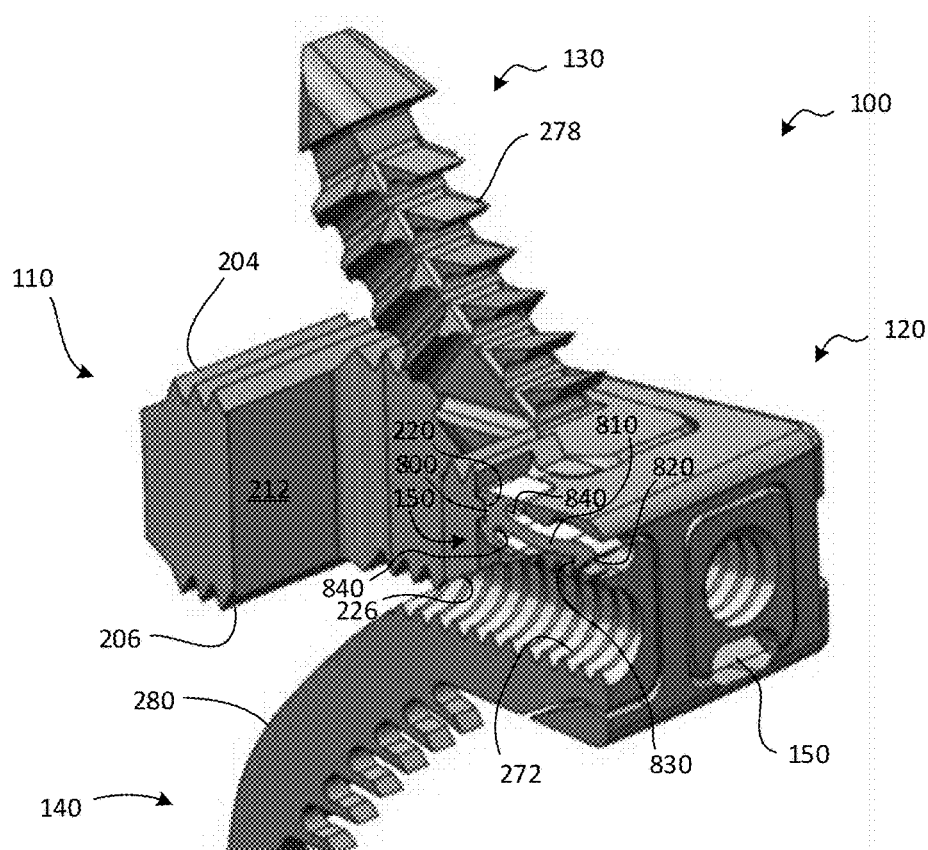
FIGS. 8A-B are section views, along the sagittal plane, of the assembly of FIGS. 1A-C in a fully-assembled state.
Figure 8B:
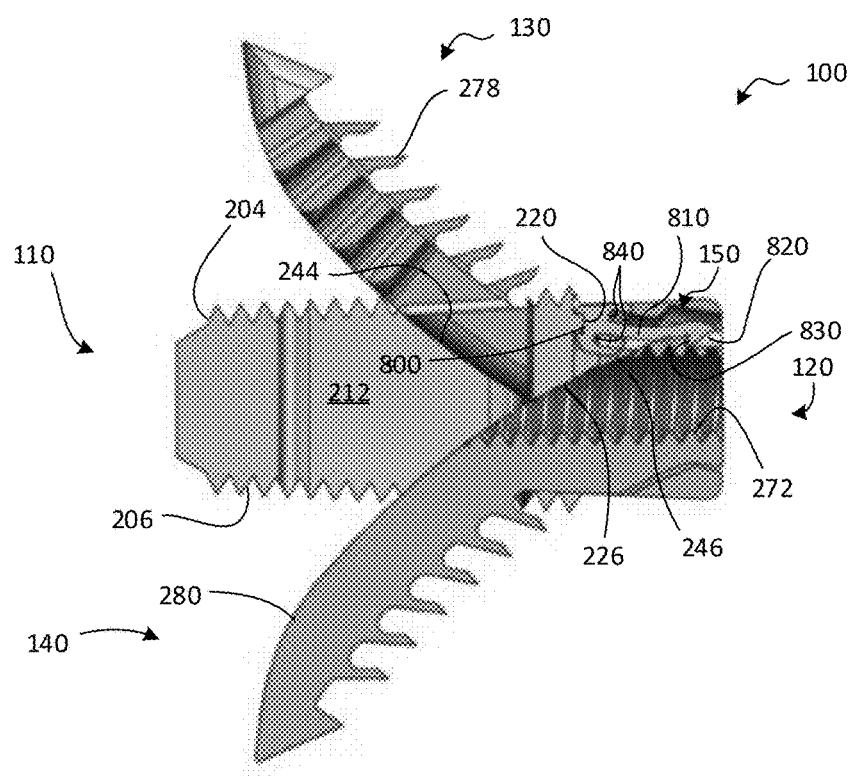

FIGS. 8A and 8B are section views, along the sagittal plane, depicting the assembly 100 in a fully-assembled state. As shown, one of the locking clips 150 may be positioned proximate the proximal end 260 of each of the superior fasteners 130 and the inferior fastener 140. The locking clips 150 may be used to restrict posterior motion of the proximal ends 260 of the superior fasteners 130 and the inferior fastener 140, relative to the bone plate 120.

The locking clips 150 may be sandwiched between the interbody spacer 110 and the bone plate 120. Each of the locking clips 150 may have a posterior recess 800 sized to receive the ridge of one of the engagement features 220. Positioning of the ridges in the posterior recesses 800 may help keep the locking clips 150 in place. In some embodiments, the locking clips 150 may remain in place between the interbody spacer 110 and the bone plate 120 without further fixation. In alternative embodiments, the locking clips 150 may be secured in place via mechanical fastening, chemical or adhesive bonding, welding, and/or the like. For example, in some embodiments, the locking clips 150 may be welded to the bone plate 120 prior to assembly of the interbody spacer 110 and the bone plate 120.

Each of the locking clips 150 may have a tongue 810 that extends anteriorly, and terminates, at its anterior end, in a beveled surface 820. The beveled surface 820 may slide along the convex surface 280 of the corresponding fastener of the superior fasteners 130 and the inferior fastener 140, causing the tongue 810 to deflect during insertion. Each tongue 810 may also have a posterior surface 830 that is oriented substantially parallel to the coronal plane. After the proximal end 260 of the corresponding fastener of the superior fasteners 130 and the inferior fastener 140 passes beyond the posterior surface 830, the tongue 810 may snap back toward the fastener such that the posterior surface 830 abuts the anteriorly-facing surface of the retention feature 270 of the proximal end 260 of the fastener. Thus, the posterior surface 830 may block motion of the fastener in the anterior direction.

Each of the locking clips 150 may further have a pair of grooves 840 toward the anterior end of the locking clip 150, facing anteriorly and positioned superior to and inferior to the tongue 810. The grooves 840 may help to provide the tongue 810 with more length, making the tongue 810 sufficiently flexible to easily permit the tongue 810 to flex out of the way when the corresponding one of the superior fasteners 130 and the inferior fastener 140 is inserted. The tongue 810 may still be rigid enough to provide secure fixation of the fastener when the tongue 810 snaps back into the undeflected (or less deflected) state.

If desired, one or more alternative forms of fixation may also be used to secure the superior fasteners 130 and the inferior fastener 140 in place relative to the bone plate 120 and the interbody spacer 110, in addition to the locking clip 150. According to one example, the holes 272 of the superior fasteners 130 and the inferior fastener 140 may be threaded such that a set screw (not shown in FIGS. 8A and 8B) can be inserted into each of the holes 272. The set screws may impinge against the corresponding ones of the superior ramps 224, ramps 244, inferior ramp 226, and ramp 246, causing the exterior surface of the fastener opposite the ramp to frictionally engage the material surrounding the superior fastener apertures 240 and the inferior fastener aperture 242. Thus, the set screws may provide additional retention force to hold the superior fasteners 130 and the inferior fastener 140 in place relative to the interbody spacer 110 and the bone plate 120.

As mentioned previously, each of the superior fasteners 130 and the inferior fastener 140 may be designed to provide purchase in bone. Advantageously, the superior fasteners 130 and the inferior fastener 140 need not be screwed in place, but can simply be advance directly into the bone, for example, along an arcuate pathway. The bone-engagement fins 278 may flex during insertion, and the tips of the bone-engagement fins 278 may set against and/or embed into the surrounding bone in response to a force urging the fastener to withdraw from the bone, thereby causing the bone-engagement fins 278 to firmly lodge the fastener in place. The superior fasteners 130 and the inferior fastener 140 may be constructed and embodied in various ways.

FIG. 9A depicts one of the fasteners (for example, the inferior fastener 140) with a one-piece configuration. The inferior fastener 140 may all be formed of a metal, plastic, or the like. In some embodiments, the inferior fastener 140 may be formed of Titanium.

FIGS. 9B and 9C are fully assembled and exploded views, respectively, of a fastener 940 according to one alternative embodiment. The fastener 940 may have a two-piece design, which may be suitable for use in place of the superior fasteners 130 and/or the inferior fastener 140 of the assembly 100. More particularly, the fastener 940 may have a metal component 950 and a polymer component 960. The metal component 950 may be formed of a metal such as Cobalt Chromium, stainless steel, or Titanium. The polymer component 960 may be formed of a polymer, such as PEEK or a more flexible biocompatible polymer.

As shown, the metal component 950 may have the proximal end 260, the distal ends 262, and a rod 970 extending through a shank 964. The polymer component 960 may have the bone-engagement fins 978 and a convex surface 980. The polymer component 960 may also have an interior channel (not shown) that receives the rod 970 so that the polymer component 960 can be secured to the rod 970 of the metal component 950. In some embodiments, the polymer component 960 may be insert molded over the metal component 950. The polymer construction of the polymer component 960 may provide the bone-engagement fins 278 with a higher degree of flexibility and/or a thicker shape than their metal counterparts, which may be desirable in some implementations. The metal component 950 may provide rigidity and structural strength that facilitates bone penetration and enhances the operating life of the fastener 940.

As mentioned previously, various forms of fixation may be used to secure a fastener relative to the remaining components of the system. Some alternatives will be shown and described in connection with FIGS. 10A and 10B, as follows.

Figure 10A:
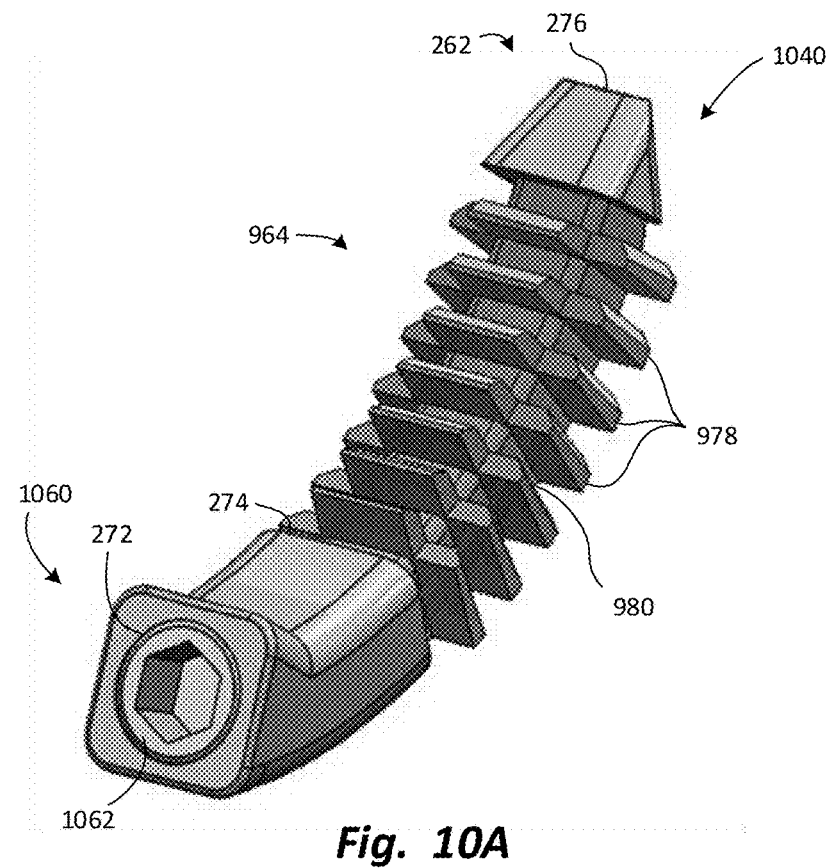
FIGS. 10A-B depict perspective views of alternative fasteners, according to other embodiments of the present disclosure.

FIG. 10A depicts a fastener 1040 according to one alternative embodiment. The fastener 1040 may have a distal end 262 and a shank 964 similar to those of the fastener 940 of FIGS. 9B and 9C. However, in place of the proximal end 260, the fastener 1040 may have a proximal end 1060 that lacks the retention feature 270 and has a hole 272 in which a set screw 1062 is positioned. The set screw 1062 may operate as described above, by engaging one or more of the superior ramps 224, the inferior ramp 226, the ramps 244, and the ramp 246, to compress the opposing side of the fastener against the interior of the bone plate 120.

Figure 10B:
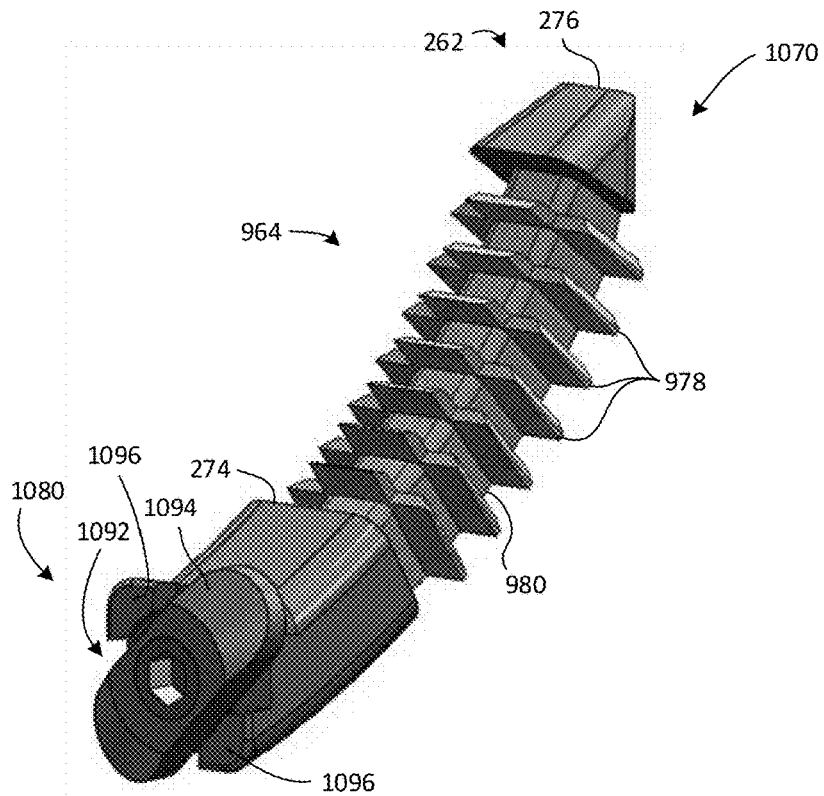

FIG. 10B depicts a fastener 1070 according to another alternative embodiment. The fastener 1070 may have a distal end 262 and a shank 964 similar to those of the fastener 940. However, in place of the proximal end 260, the fastener 1070 may have a proximal end 1080 that lacks the retention feature 270 and has a hole (not shown) that can receive a winged screw 1092. The winged screw 1092 may have wings 1094 that fit into slots or other features (not shown) of a bone plate to keep the proximal end 1080 from moving anteriorly. The proximal end 1080 may further have bosses 1096 that control the range of motion of the winged screw 1092, to limit the winged screw 1092 to a predetermined range of motion, such as 45° or 90°.

In order to provide enhanced fixation in bone, it may be desirable to use a fastener that expands after penetrating the bone. Any expandable fasteners known in the art may be used. Some expanding alternatives will be shown and described in connection with FIGS. 11A through 12C, as follows.

Figures 11A, 11B:
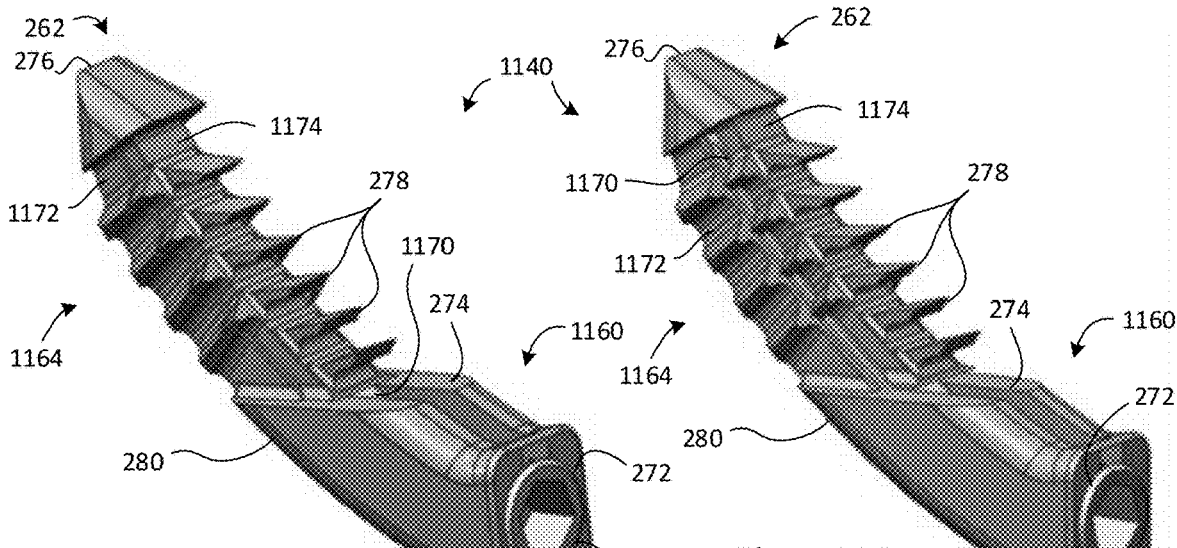
FIGS. 11A-F depict a fastener, according to yet another embodiment of the present disclosure.
Figures 11C, 11D:
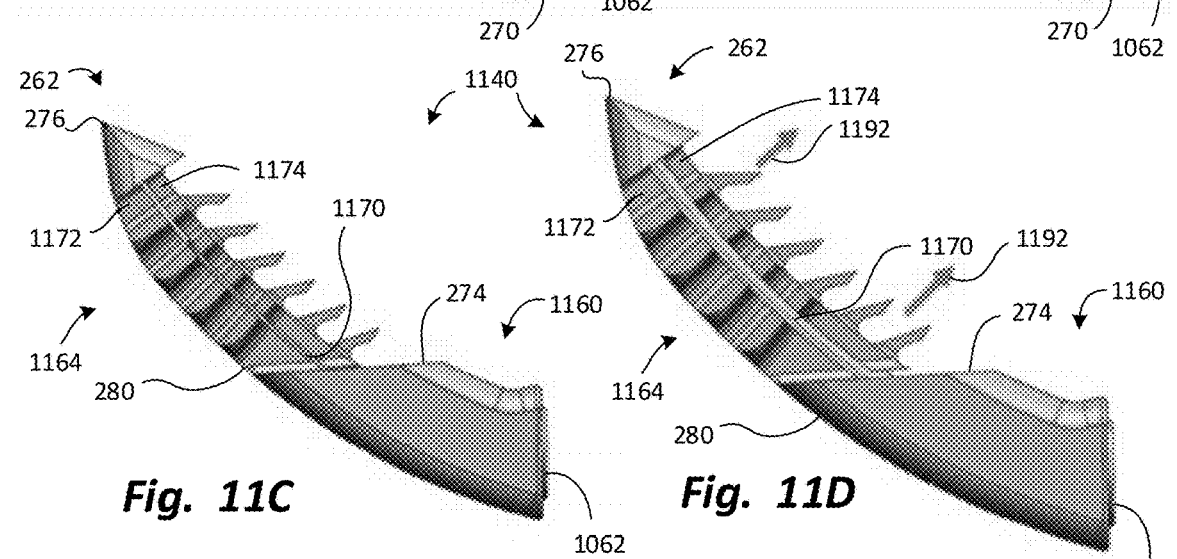
Figures 11E, 11F:
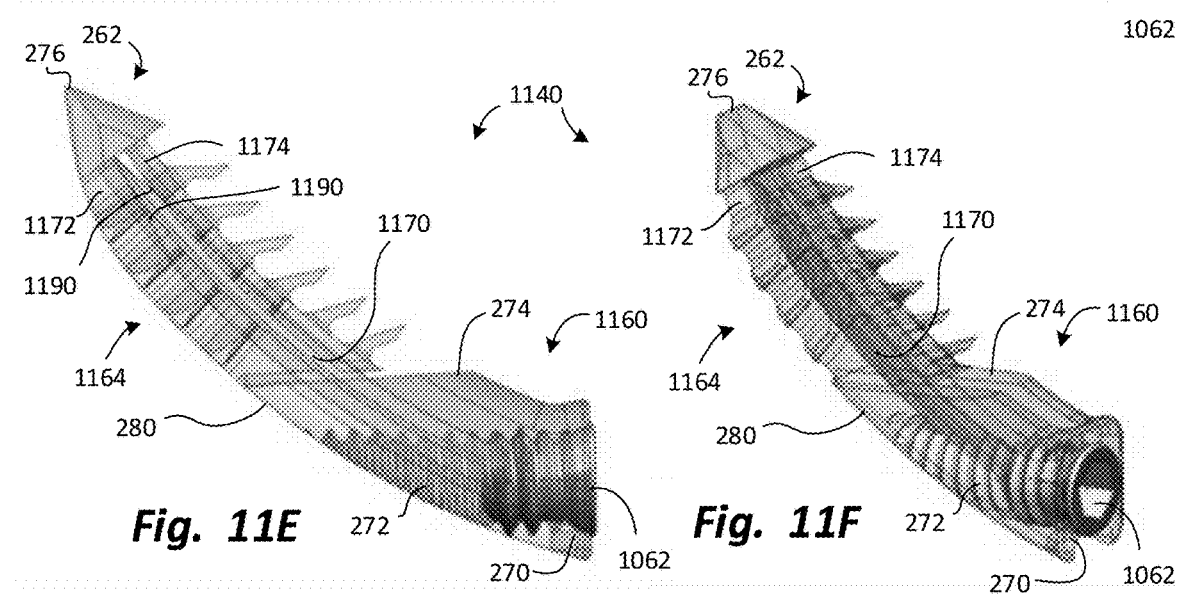

FIGS. 11A through 11F depict a fastener 1140 according to one alternative embodiment. The fastener 1140 may have a stowed configuration, in which the fastener 1140 has a smaller cross-sectional area suitable for bone penetration, and a deployed configuration, in which the fastener 1140 has an enlarged cross-sectional area that provides more secure fixation with the surrounding bone once the fastener 1140 is in place. FIGS. 11A and 11C depict the fastener 1140 in the stowed configuration, and FIGS. 11B and 11D through 11F depict the fastener 1140 in the deployed configuration.

As shown, the fastener 1140 may have a distal end 262 similar to that of the fastener 940. However, in place of the proximal end 260 and the shank 964, the fastener 1140 may have a proximal end 1160 and a shank 1164, respectively, that facilitate expansion of the fastener 1140 within the bone. The proximal end 1160 may have a retention feature 270 and a hole 272 like those of the superior fasteners 130 and the inferior fastener 140. A set screw 1062 may reside within the hole 272. A shoulder 274 may separate the proximal end 1160 from the shank 1164.

The shank 1164 may have a wedge member 1170 that divides a first portion 1172 from a second portion 1174. The shank 1164 may have bone-engagement fins 278, which may reside on the first portion 1172 and on the second portion 1174. Some of the bone-engagement fins 278 may be divided between the first portion 1172 and the second portion 1174. The shank 1164 may further have a convex surface 280 on the first portion 1172.

In the stowed configuration of FIGS. 11A and 11C, the first portion 1172 and the second portion 1174 may be relatively close to each other, and the wedge member 1170 may be retracted away from the distal end 262 of the fastener 1140. After the fastener 1140 has been inserted into the bone such that the distal end 262 and the shank 1164 reside in the bone, the fastener 1140 may be actuated to the deployed configuration by rotating the set screw 1062 to move the set screw 1062 further (i.e., distally) into the hole 272. The distal end of the set screw 1062 may abut the proximal end of the wedge member 1170, thereby urging the wedge member 1170 to move distally, toward the distal end 262. The wedge member 1170 may exert pressure on adjoining sloped surfaces 1190 (shown in FIG. 11E) of the first portion 1172 and the second portion 1174, causing the second portion 1174 to move away from the first portion 1172 in the direction shown by the arrows 1192 of FIG. 11D.

The result may be that the shank 1164 assumes a larger cross-sectional area in the deployed configuration. The outward motion of the first portion 1172 and/or the second portion 1174 may serve to compact the bone surrounding the shank 1164 and may drive the bone-engagement fins 278 into the bone, providing more secure purchase in the bone to resist pullout of the fastener 1140 from the bone.

FIGS. 12A through 12C depict a fastener 1240 with an expandable configuration, according to another embodiment. Like the fastener 1140, the fastener 1240 may be inserted into the bone in a stowed, or compact, configuration, and then expanded in-situ for enhanced bone-engagement and pull-out strength. The fastener 1240 may have a shell 1250 and a core 1252 that can be moved axially within the shell 1250 to move the shell 1250 from the stowed configuration (shown in FIG. 12A) to the deployed configuration (not shown).

As shown in FIG. 12B, the shell 1250 may have a proximal end 1260, a distal end 1262, and a shank 1264 that connects the proximal end 1260 to the distal end 1262. The shell 1250 may have a bore 1266 that extends axially through the shell 1250, from the proximal end 1260 to the distal end 1262. The proximal end 1260 may have a flange 1270 with a generally discoid shape. The shank 1264 may have longitudinal slots 1272 that divide the shank 1264 into a plurality of segments 1274 that are able to bend away from each other in the deployed configuration. The distal end 1262 may have a plurality of bone-engagement fins 1276, which may traverse the circumference of the distal end 1262 and may be split by the longitudinal slots 1272.

As shown in FIG. 12C, the core 1252 may have a proximal end 1280, a distal end 1282, and a shank 1284 that connects the proximal end 1280 to the distal end 1282. The proximal end 1280 may have a flange 1290, and the distal end 1282 may have a tip 1296, and a proximal shoulder 1298 with a generally conical shape.

During insertion into the bone, the shank 1284 of the core 1252 may reside within the bore 1266 of the shell 1250, and the flange 1290 of the core 1252 may be positioned proximate the flange 1270 of the shell 1250. The proximal shoulder 1298 may not exert significant pressure on the distal ends of the segments 1274, so the segments 1274 may remain generally parallel to each other, in the stowed configuration. The fastener 1240 may be inserted into the bone, for example, by impacting the flange 1290 with a hammer or other striking instrument to cause the tip 1296 to penetrate the bone.

When the fastener 1240 has reached the desired position within the bone, the fastener 1240 may be moved to the deployed configuration. This may be done, for example, by drawing the flange 1290 of the core 1252 proximally, away from the flange 1270 of the shell 1250. This may be done, for example, by inserting one or more wedge members or shims into the space between the flange 1270 and the flange 1290 to move the flange 1290 proximally, relative to the flange 1270.

This proximal motion of the core 1252 may draw the proximal shoulder 1298 proximally against the distal ends of the segments 1274. The distal ends of the segments 1274 may have ramps (not shown) matched to the contour of the proximal shoulder 1298. In response to proximal pressure of the proximal shoulder 1298, the distal ends of the segments 1274 may be splayed apart, causing the shell 1250 to move to the deployed configuration. The bone-engagement fins 1276 may be driven outward into the surrounding bone, increasing bone-engagement and pullout strength.

The assembly 100 previously described is merely exemplary. Many other assemblies may be devised within the scope of the present disclosure. A wide variety of interbody spacers, bone plates, and fixation elements may also be used. One alternative assembly will be shown and described in connection with FIG. 13.

Figure 13:
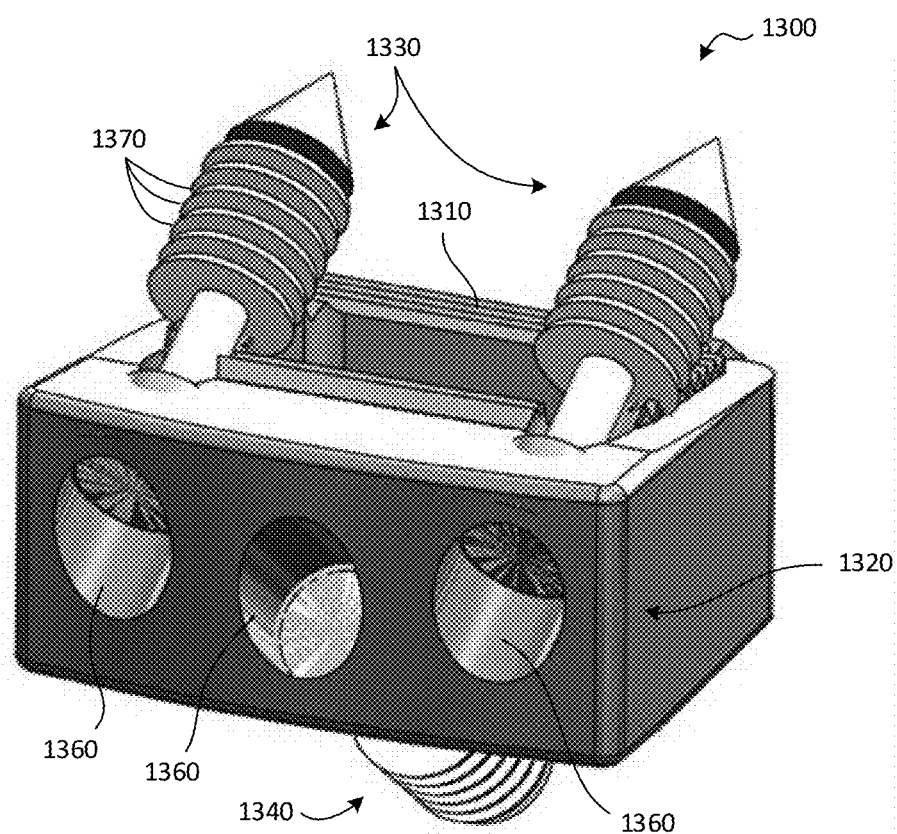
FIG. 13 depicts an assembly for stabilizing a spinal joint, according to another embodiment of the present disclosure.

FIG. 13 depicts an assembly 1300 for stabilizing a spinal joint, according to one alternative embodiment. The assembly 1300 may have an interbody spacer 1310, a bone plate 1320, two superior fasteners 1330, and an inferior fastener 1340. These components may perform functions generally similar to those of their counterparts in the assembly 100. However, the superior fasteners 1330 and the inferior fastener 1340 may be inserted along superior-posterior trajectories, and an inferior-posterior trajectory, respectively. The superior fasteners 1330 and the inferior fastener 1340 may be straight, rather than curved, to accommodate such a trajectory. In alternative embodiments, the superior fasteners 1330 and/or the inferior fasteners 1340 may be curved, for example, like the superior fasteners 130 and the inferior fasteners 140, to facilitate insertion of the superior fasteners 1330 and/or the inferior fasteners 1340 along a posterior trajectory, as in the assembly 100 of FIGS. 1A through 4C.

The bone plate 1320 and the interbody spacer 1310 may not need ramps to redirect the trajectory of the superior fasteners 1330 and the inferior fastener 1340 because the superior fasteners 1330 and the inferior fastener 1340 may be inserted along straight pathways. Accordingly, the bone plate 1320 may have three holes 1360, with the holes 1360 in the lateral positions angled superiorly to receive the superior fasteners 1330, and the hole 1360 in the medial position angled inferiorly to receive the inferior fastener 1340. As in previous embodiments, different numbers of fasteners may be used in any combination of superior and inferior fasteners.

The superior fasteners 1330 and the inferior fastener 1340 may have bone-engagement fins 1370, which may flex during insertion of the superior fasteners 1330 and the inferior fastener 1340 into the bone to facilitate entry. The bone-engagement fins 1370 may lodge against the bone in response to force tending to withdraw the superior fasteners 1330 and the inferior fastener 1340 from the bone. If desired, the superior fasteners 1330 and the inferior fastener 1340 may each have a two-piece construction, with a core member formed of a metal, and a coating formed of a polymer that may also carry the bone-engagement fins 1370. The metal may provide rigidity, and the polymer may provide additional flexure and retention in the bone.

FIGS. 14A-C are perspective, anterior elevation, and lateral elevation views, respectively, of an assembly 2100 according to another embodiment of the present disclosure. The assembly 2100 may be designed to stabilize a joint between a superior vertebra and an co inferior vertebra. Specifically, the assembly 2100 may perform the functions normally carried out by an interbody spacer and a bone plate, particularly for a cervical joint. Thus, as embodied in FIGS. 14A-C, the assembly 2100 may have an interbody spacer 2110, a bone plate or plate member 2120, two superior fasteners 2130, and an inferior fastener 2140. The configuration and operation of these components will be further described in connection with FIG. 15.

Figure 15:
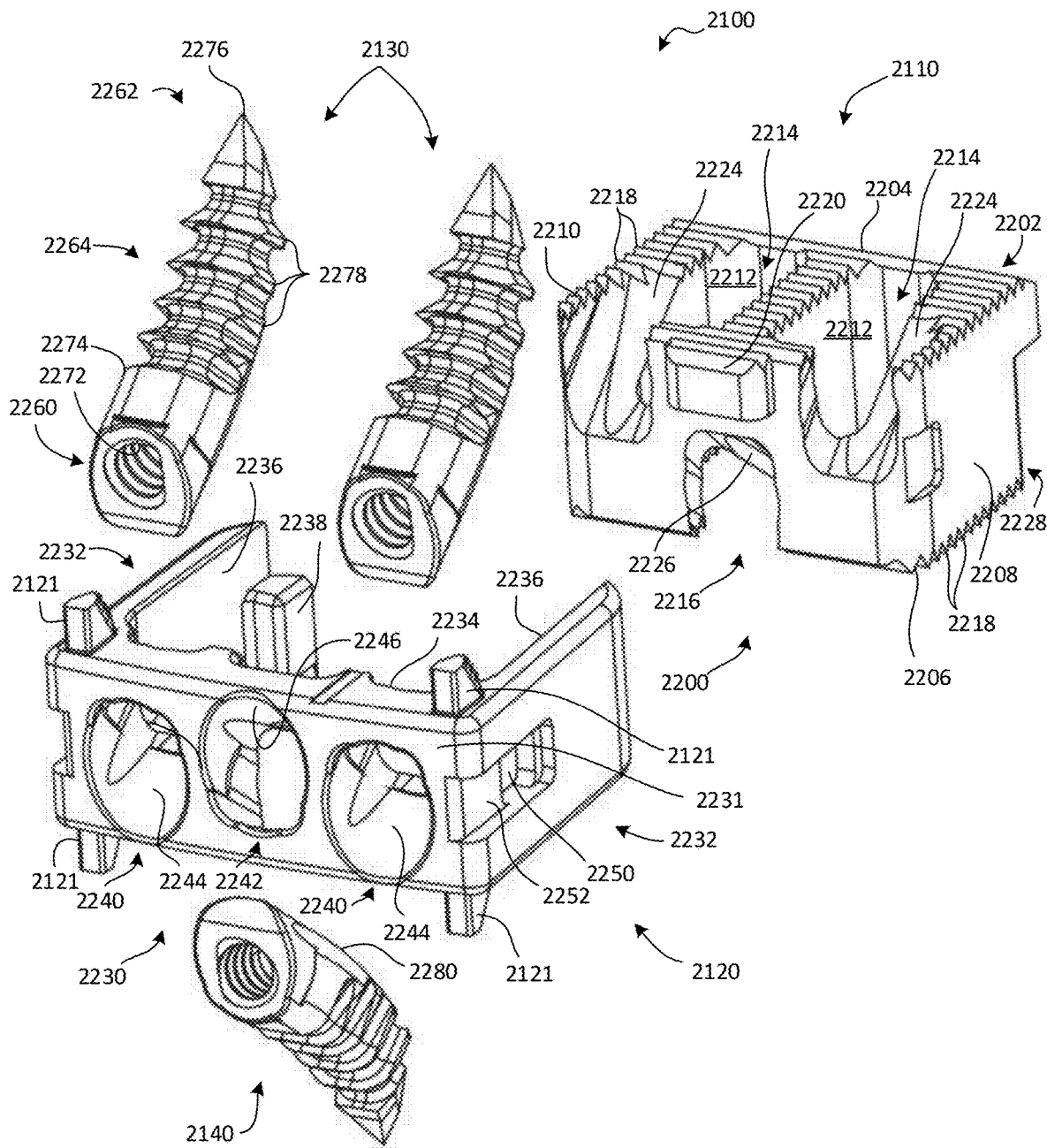
FIG. 15 is an exploded view of the assembly of FIGS. 14A-C.

FIG. 15 is an exploded view of the assembly of FIGS. 14A-C. The interbody spacer 2110 and the bone plate 2120 may be complimentarily shaped so that they can be coupled together (for example, via snap fitting), and then inserted together into the intervertebral space. The interbody spacer 2110 and the bone plate 2120 may then be secured to the superior vertebra and the inferior vertebra through the use of the superior fasteners 2130 and the inferior fastener 2140. A locking plate, as will be discussed further with regard to FIGS. 23A-C, may additionally operate to prevent the superior fasteners and the inferior fastener 2140 from "backing out," or withdrawing over time, from the superior and inferior vertebrae, respectively.

FIGS. 16A-D illustrate various views of the interbody spacer utilized in the assembly shown in FIGS. 14A-C and FIG. 15. With reference to FIGS. 15 and 16A-D, the interbody spacer 2110 may have an anterior end 2200, a posterior end 2202, a superior bone-facing surface 2204, and an inferior bone-facing surface 2206. These elements are named according to the orientation in which the interbody spacer 2110 will be inserted into the intervertebral space. The interbody spacer 2110 may also have a left lateral side 2208 and a right lateral side 2210. The interbody spacer 2110 may define one or more interior cavities 2212 bounded by one or more superior bone-engagement apertures 2214 defined in the superior bone-facing surface 2204, and one or more inferior bone-engagement apertures 2216 defined in the inferior bone-facing surface 2206. The interior cavities 2212 may have a size and shape suited to retention of bone graft or other materials suitable for encouraging formation of a column of bone that connects the superior vertebra and the inferior vertebra together.

The superior bone-facing surface 2204 and the inferior bone-facing surface 2206 may each have teeth 2218 that engage the superior vertebra and the inferior vertebra to help keep the interbody spacer 2110 in place relative to the superior vertebra and the inferior vertebra as the bone column forms. The anterior end 2200 may have engagement features 2220 that may engage the bone plate 2120 in order to help keep the interbody spacer 2110 in place relative to the bone plate 2120. The engagement features 2220 may, for example, be an outwardly extending tab that fits into a complementary shaped recess 2221 formed in the bone plate 2120 to help keep the interbody spacer 2110 in place relative to the bone plate 2120.

The anterior end 2200 and the superior bone-facing surface 2204 may further be shaped to define superior ramps 2224, one at the left lateral side 2208 and one at the right lateral side 2210. The superior ramps 2224 may extend superiorly as they extend posteriorly, thereby redirecting the superior fasteners 2130 from a posterior trajectory to a superior trajectory suitable for piercing and anchoring in the vertebral body of the superior vertebra, as will be shown and described subsequently. The space above the superior ramps 2224, inside the interbody spacer 2110, may define first interior spaces which may receive the superior fasteners 2130. Similarly, the anterior end 2200 and the inferior bone-facing surface 2206 may be further shaped to define an inferior ramp 2226, which may extend inferiorly as it extends posteriorly, thereby redirecting the inferior fastener 2140 from a posterior trajectory to an inferior trajectory suitable for piercing and anchoring in the vertebral body of the inferior vertebra, as will also be shown and described subsequently. The space below the inferior ramp 2224, inside the interbody spacer 2110, may define a second interior space which may receive the inferior fastener 2140.

The left lateral side 2208 and the right lateral side 2210 may each have a recess 2228 and an additional recess 2111. The recesses 2228, 2111 may each facilitate engagement of the bone plate 2120 with the interbody spacer 2110. The bone plate 2120 may be secured to the interbody spacer 2110 prior to insertion of the interbody spacer 2110 and bone plate 2120 into the intervertebral space.

In some embodiments, the assembly 2100 may be implanted between two vertebrae of the cervical spine, from along an anterior approach. The terms "superior," "inferior," "anterior," "posterior," "medial," and "lateral" are used in this description with reference to such an embodiment. In such an implementation, the bone plate 2120 may be an "anterior bone plate." However, those of skill in the art will recognize that the systems and methods disclosed herein are not limited to such an implantation site, or to such an approach.

FIGS. 17A-D illustrate various views of the bone plate or plate member 2120 utilized in the assembly shown in FIGS. 14A-C and FIG. 15. With reference to FIGS. 15 and 17A-D, the bone plate 2120 may have an anterior end 2230 defined by an anterior end plate having an anterior surface 2231 and two posterior extensions 2232, or first and second posterior extension plates 2232, that extend posteriorly from the anterior end plate 2230. The anterior end 2230 may define a posterior surface 2234 that abuts and engages the anterior end 2200 of the interbody spacer 2110. Similarly, each of the posterior extensions 2232 may define an interior surface 2236 that abuts and engages the corresponding one of the left lateral side 2208 and the right lateral side 2210 of the interbody spacer 2110. Further, each of the posterior extensions 2232 may have engagement features 2238, 2112 designed to enter and engage one of the recess 2228, 2111 of the left lateral side 2208 and the right lateral side 2210 of the interbody spacer 2110.

Figure 18A:
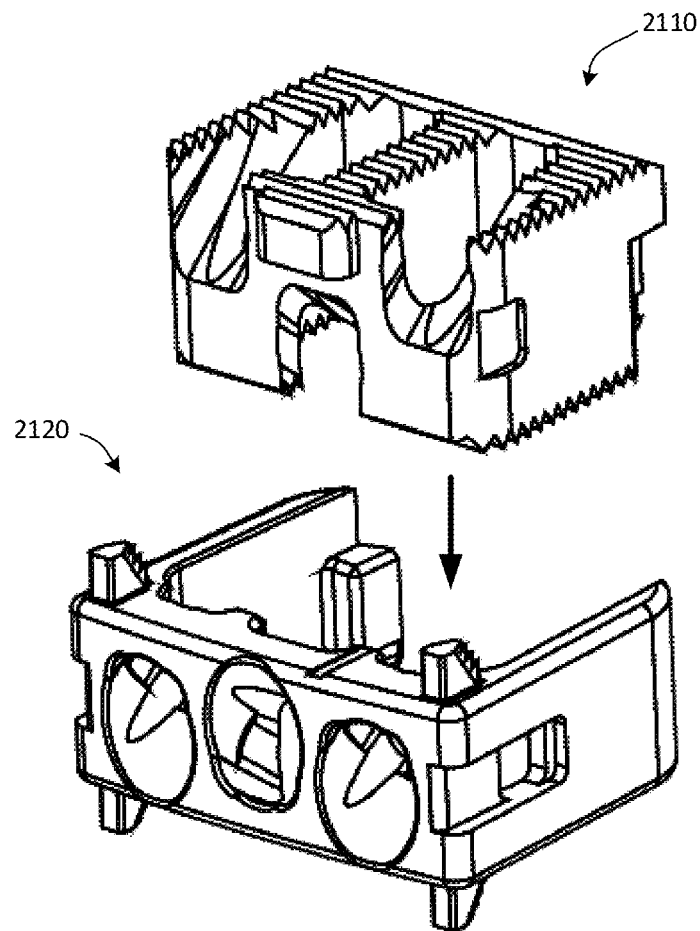
FIGS. 18A-B illustrate how the interbody spacer of FIGS. 16A-D may be inserted into the plate member of FIGS. 17A-D.
Figure 18B:
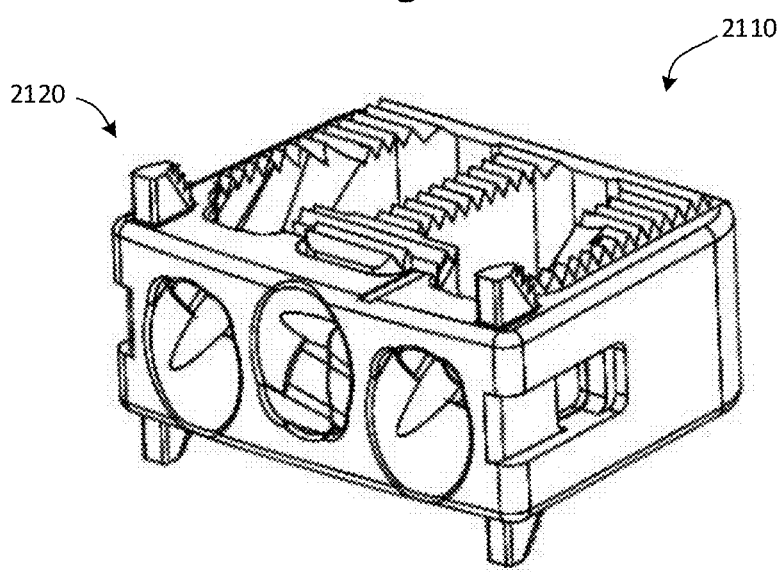
Figure 19A:
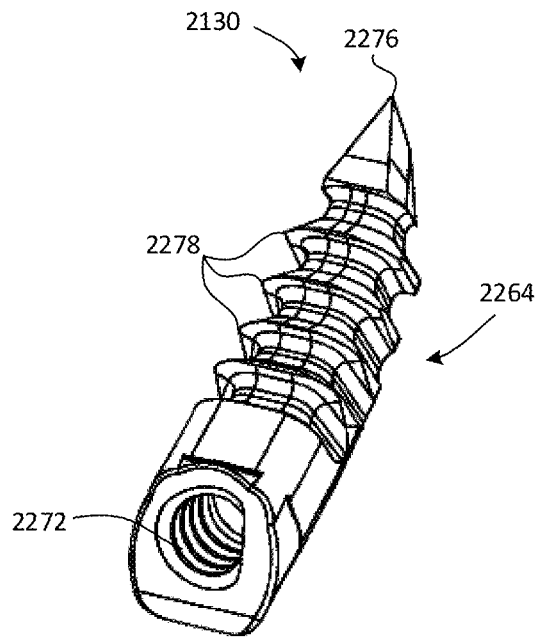
FIGS. 19A-D illustrate various views of a fastener that is utilized in the assembly shown in FIGS. 14A-C.
Figure 19B:
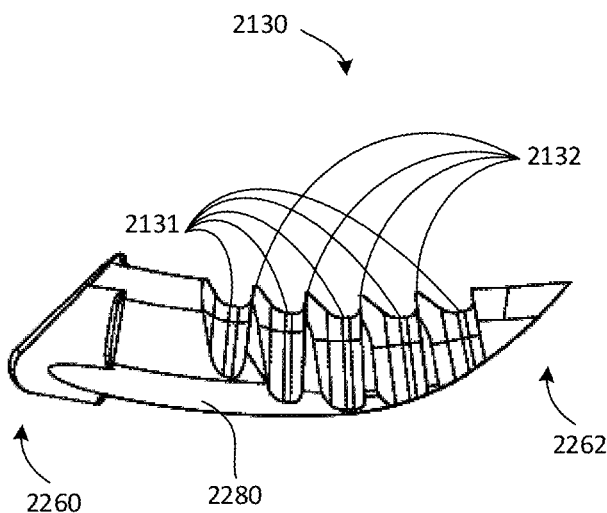
Figure 19C:
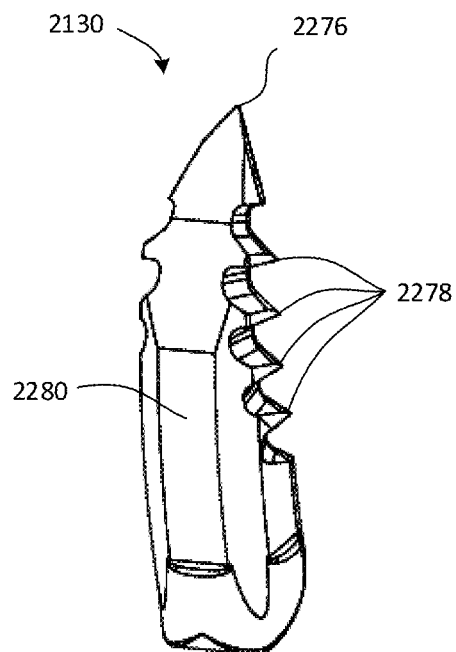
Figure 19D:
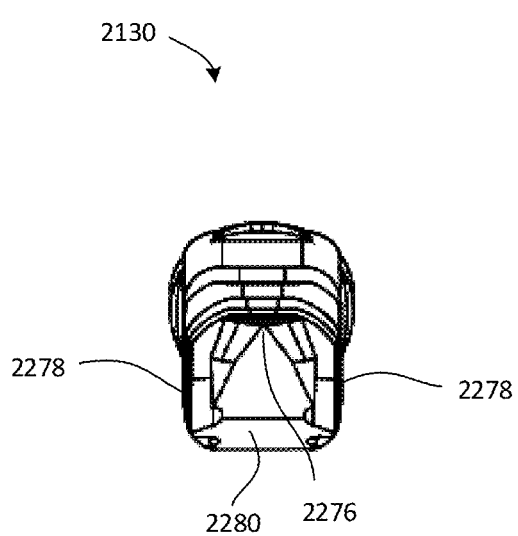

For example, the engagement features 2238, 2112 may be nubs 2238, 2112 that extend medially. The nubs 2238, 2112 may be rounded such that they facilitate assembly of the interbody spacer 2110 and the bone plate 2120 from along a superior-inferior direction, as shown in FIGS. 18A-B. For example, the interbody spacer 2110 and the bone plate 2120 may be assembled by aligning the interbody spacer 2110 and the bone plate 2120 at approximately the same anterior/posterior position, with the interbody spacer 2110 superior to the bone plate 2120, and then moving the interbody spacer 2110 inferiorly into engagement with the bone plate 2120. The nubs 2238, 2112 may abut the interbody spacer 2110 proximate the recesses 2228, 2111 of the interbody spacer 2110 and their rounded shape may cause the posterior extensions 2232 to spread apart to receive the interbody spacer 2110 between the posterior extensions 2232. The bone plate 2120 may slide superiorly along the interbody spacer 2110 until the nubs 2238, 2112 enter the recesses 2228, 2111 of the left lateral side 2208 and the right lateral side 2210 of the interbody spacer 2110. Thus, the bone plate 2120 may be snap fitted to the interbody spacer 2110.

In alternative embodiments, different assembly modes may be used. For example, the interbody spacer 2110 may be positioned directly posterior to the bone plate 2120, and then moved anteriorly until the interbody spacer 2110 is positioned between the posterior extensions 2232 of the bone plate 2120. The nubs 2238, 2112 may enter the recesses 2228, 2111 of the left lateral side 2208 and the right lateral side 2210 along an anterior trajectory, causing the bone plate 2120 to engage and retain the interbody spacer 2110.

The anterior end 2230 of the bone plate 2120 may be shaped to define superior fastener apertures 2240 proximate each of the posterior extensions 2232, and an inferior fastener aperture 2242 between the superior fastener apertures 2240. The superior fastener apertures 2240 and the inferior fastener aperture 2242 may be sized to receive the superior fasteners 2130 and the inferior fastener 2140, respectively. The anterior end 2230 of the bone plate 2120 may further be shaped to define ramps 2244 adjacent to the superior fastener apertures 2240, and a ramp 2246 adjacent to the inferior fastener aperture 2242.

The bone plate 2120 may also include a plurality of anti-torsion members 2121, each of which may extend away from the bone plate superiorly and/or inferiorly along a cephalad-caudal direction. Each of the anti-torsion members 2121 have an angled cutting edge or serrated leading end 2122 with broach-like teeth to facilitate penetration of cortical bone. The anti-torsion members 2121 may be configured to penetrate the cortical bone of at least one of the superior vertebra and the inferior vertebra and resist torsion forces that may be applied to the bone plate 2120 to further secure the bone plate 2120 to the superior and/or inferior vertebra.

In the embodiment of FIGS. 14A-23C, there are two superior fasteners 2130 and one inferior fastener 2140. In alternative embodiments, any combination of fasteners may be used. For example, there may be two inferior fasteners and one superior fastener, one of each type, two of each type, or the like. Further, in some embodiments, more than four fasteners may be used, with any combination of superior and inferior fasteners. Moreover, any fastener type may be utilized with any implant disclosed herein.

Further, the interbody spacer 2110 and the bone plate 2120 may, in some embodiments, be used independently of each other. For example, the interbody spacer 2110 may be implanted between two adjacent vertebrae without the use of an anterior bone plate, and/or without the use of fasteners. In some embodiments, the interbody spacer 2110 may, without the use of the bone plate 2120, the superior fasteners 2130, and/or the inferior fastener 2140, satisfy the reimbursement requirements for interbody spacers, such as those associated with the OBP reimbursement code.

Further to the foregoing, the bone plate 2120 may also be used with the superior fasteners 2130 and/or the inferior fastener 2140, independently of the use of the interbody spacer 2110. The bone plate 2120 may be implanted between two adjacent vertebrae, with the posterior extensions 2232 extending posteriorly between the central portions of the vertebral bodies. The ramps 2244 and the ramp 2246 may be used to redirect the superior fasteners 2130 and the inferior fastener 2140 from posterior trajectories to superior and inferior trajectories, respectively, such that the superior fasteners 2130 and the inferior fastener 2140 anchor in the adjacent vertebral bodies to secure the bone plate 2120 in place without the interbody spacer 2110. In some embodiments, the bone plate 2120, superior fasteners 2130, and inferior fastener 2140 may, without the use of the interbody spacer 2110, satisfy the reimbursement requirements for anterior bone plates, such as those associated with the KWQ reimbursement code.

Yet further to the foregoing, the interbody spacer 2110 and the bone plate 2120 may be assembled and implanted together and may cooperate to facilitate implantation of the superior fasteners 2130 and the inferior fastener 2140, as will be discussed below. In some embodiments, the interbody spacer 2110, the bone plate 2120, the superior fasteners 2130, and the inferior fastener 2140 may cooperate to satisfy the reimbursement requirements for a system including an anterior bone plate and an interbody spacer, such as those associated with the OVE reimbursement code.

When the interbody spacer 2110 and the bone plate 2120 are assembled together, the ramps 2244 may align with the superior ramps 2224 of the interbody spacer 2110 to define two continuous superiorly-angled ramp surfaces extending from the bone plate 2120 to the interbody spacer 2110. Similarly, when the interbody spacer 2110 and the bone plate 2120 are assembled together, the ramp 2246 may align with the inferior ramp 2226 of the interbody spacer 2110 to define one continuous inferiorly-angled ramp surface extending from the bone plate 2120 to the interbody spacer 2110.

In a particular embodiment, the anterior end plate 2230 may include at least one superior plate member ramp 2244 formed between the anterior surface 2231 of the anterior end plate 2230 and the posterior surface 2234 of the anterior end plate 2230, the superior plate member ramp 2244 may be angled superiorly at a first angle. The anterior end plate 2230 may also include at least one inferior plate member ramp 2246 formed between the anterior surface 2231 of the anterior end plate 2230 and the posterior surface 2234 of the anterior end plate 2230. The inferior plate member ramp 2246 may be angled inferiorly at a second angle. The interbody spacer 2110 may also include at least one superior interbody spacer ramp 2224 formed between the anterior end 2200 of the interbody spacer 2110 and the posterior end 2202, or a posterior surface, of the interbody spacer 2110. The at least one superior interbody spacer ramp 2224 may be angled superiorly at a third angle. The interbody spacer 2110 may also include at least one inferior interbody spacer ramp 2226 formed between the anterior end 2200 of the interbody spacer 2110 and a posterior surface 2202 of the interbody spacer 2110. The at least one inferior interbody spacer ramp 2226 may be angled inferiorly at a fourth angle. In this embodiment, once the interbody spacer 2110 is assembled together with the bone plate 2120, the at least one superior plate member ramp 2244 may abut against the at least one superior interbody spacer ramp 2224, and the at least one inferior plate member ramp 2246 may abut against the at least one inferior interbody spacer ramp 2226 to form continuous ramps. However, the first angle of the at least one superior plate member ramp 2244 may be less than the third angle of the at least one superior interbody spacer ramp 2224 such that the at least one superior plate member ramp 2244 may cooperate with the at least one superior interbody spacer ramp 2224 to define a first discrete faceted curvature. Likewise, the second angle of the at least one inferior plate member ramp 2246 may be less than the fourth angle of the at least one inferior interbody spacer ramp 2226 such that the at least one inferior plate member ramp 2246 may cooperate with the at least one inferior interbody spacer ramp 2226 to define a second discrete faceted curvature. The first discrete faceted curvature and the second discrete faceted curvature may be configured to substantially conform to a convex curvature of a smooth surface 2280 of a shank 2264 of a suitable fastener to facilitate sliding the smooth surface 2280 of the shank 2264 of the fastener along the first discrete faceted curvature and the second discrete faceted curvature.

Continuing with FIGS. 15-17D, the bone plate 2120 may have features 2252, 2250 that facilitate gripping of the bone plate 2120 by an inserter. Specifically, in the embodiment of FIGS. 15-17D, each of the posterior extensions 2232 of the bone plate 2120 may have a window 2250 extending therethrough, and a groove 2252 extending from the anterior end 2230 of the bone plate 2120 to the window 2250. An inserter may have arms that engage the windows 2250 via the grooves 2252, as will be shown and described subsequently.

With reference to FIGS. 15 and 19A-D, in some embodiments, the inferior fastener 2140 may be a spike and may have the same configuration as the superior fasteners 2130. Each of the superior fasteners 2130 may have a proximal end 2260, a distal end 2262, and a shank 2264 extending longitudinally between the proximal end 2260 and the distal end 2262.

Each proximal end 2260 may have a hole 2272 that may be used for supplemental retention and/or withdrawal of the superior fasteners 2130 and/or the inferior fastener 2140 from the bone plate 2120 for revision. More specifically, the hole 2272 may have female threads that can receive male threads of a set screw to help keep the fastener in place relative to the bone plate 2120 and the interbody spacer 2110, or the male threads of a removal tool (not shown) designed to remove the fasteners from the bone plate 2120 and the interbody spacer 2110. A shoulder 2274 may also separate the proximal end 2260 from the shank 2264.

The distal end 2262 may have a sharpened tip 2276 shaped to penetrate bone. The shank 2264 may have a plurality of bone-engagement fins 2278 that engage the bone and help prevent unintended withdrawal of the superior fasteners 2130 and the inferior fastener 2140 from the bone. The bone-engagement fins 2278 may each have a thickness selected to enable the bone-engagement fins 2278 to bend toward the proximal end 2260 during insertion of the superior fasteners 2130 and inferior fastener 2140 into the bone. The bone-engagement fins 2278 may then set themselves in the bone in a barb-like manner in response to force tending to urge the superior fasteners 2130 and the inferior fastener 2140 to pull out of the bone. The shank 2264 may further have a smooth and/or convex surface 2280 extending along a proximal-distal length of the shank 2264. The smooth and/or convex surface 2280 of the shank 2264 may be configured to slide along the superior ramps 2224, the inferior ramp 2226, the ramps 2244, and/or the ramp 2246.

In a particular embodiment, the plurality of bone-engagement fins 2278 may be arranged along a majority of the proximal-distal length of the shank 2264. The plurality of bone-engagement fins 2278 may extend away from a longitudinal center of the shank 2264. Each of the plurality of bone-engagement fins 2278 may occupy more than half, but less than all, of a perimeter of an associated cross-section of the shank 2264 taken perpendicular to the smooth surface 2280 of the shank.

However, it will also be understood that in other embodiments the plurality of bone-engagement fins 2278 may occupy less than half, in some embodiments, and/or all, in other embodiments, of a perimeter of an associated cross-section of the shank 2264 taken perpendicular to the smooth surface 2280 of the shank.

In another particular embodiment, the plurality of bone-engagement fins 278 may be coupled to the shank 2264 and extend away from a longitudinal center of the shank 2264. The plurality of bone-engagement fins 2278 may include a plurality of apexes 2132 that cooperate to define a major diameter of the shank 2264, which may taper from the proximal end 2260 of the shank 2264 toward the distal end 2262 of the shank 2264. The bone-engagement fins 2278 may also define a plurality of troughs 2133 between adjacent bone-engagement fins 2278 that may cooperate to define a minor diameter of the shank 2264 that may also taper from the proximal end 2260 of the shank 2264 toward the distal end 2262 of the shank 2264.

A locking plate 2160 may also be used to further retain the superior fasteners 2130 and/or the inferior fastener 2140 in place, relative to the bone plate 2120, as will be further described in connection with FIGS. 23A-C.

The interbody spacer 2110, the bone plate 2120, the superior fasteners 2130, the inferior fastener 2140, and the locking plate 2160 may be made from various bio-compatible materials. Metals, plastics, ceramics, and combinations thereof may be used. In some embodiments, some components may be made of metal while others are plastic. For example, in one embodiment, the interbody spacer 2110 may be formed of a biocompatible polymer such as PEEK, and the bone plate 2120 may be made of a biocompatible metal such as Titanium. The superior fasteners 2130 and the inferior fastener 2140 may be made of Titanium, polymers, and/or combinations thereof. The locking plate 2160 may also be made of Titanium, polymers, and/or combinations thereof.

The curved shapes of the superior fasteners 2130 and the inferior fastener 2140, in combination with the superior ramps 2224, the inferior ramp 2226, the ramps 2244, and the ramp 2246 may allow the superior fasteners 2130 and the inferior fastener 2140 to be inserted and urged along a posterior direction to move superiorly and inferiorly, respectively, into the superior vertebra and the inferior vertebra. This will be further described in connection with FIGS. 20A-22C, as follows.

Figure 20A:
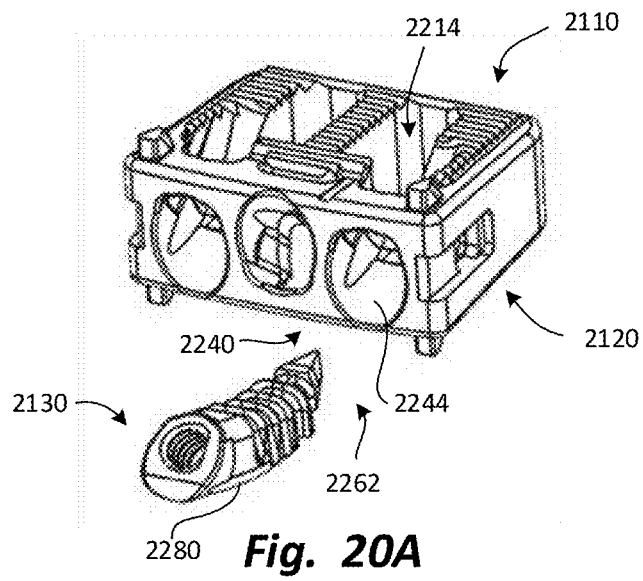
FIGS. 20A-C are perspective views of the assembly of FIGS. 14A-C depicting various stages of fastener insertion.
Figure 20B:
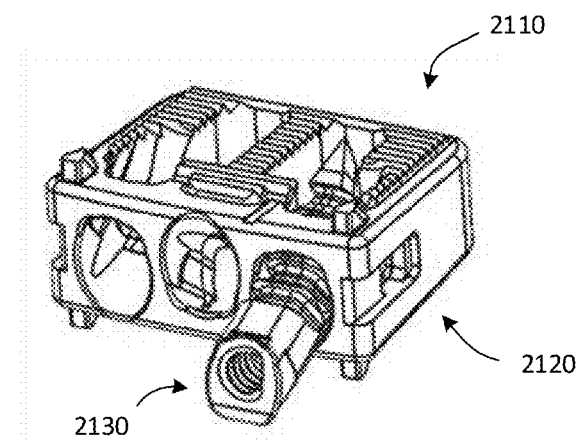
Figure 20C:
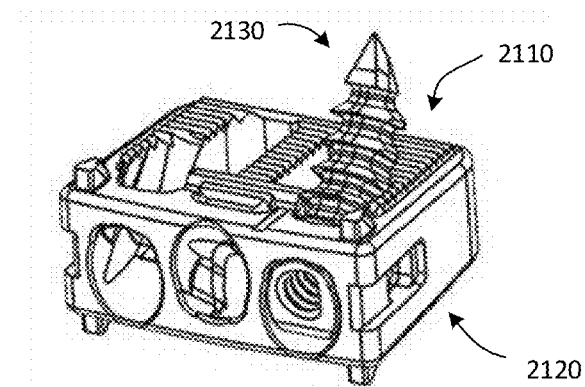

FIGS. 20A-C depict the interbody spacer 2110, the bone plate 2120, and one of the superior fasteners 2130, in various stages of fastener insertion. In FIG. 20A, one of the superior fasteners 2130 has been aligned with one of the superior fastener apertures 2240 of the anterior end 2230 of the bone plate 2120. The distal end 2262 of one of the superior fasteners 2130 may be inserted along a posterior trajectory into one of the superior fastener apertures 2240, such that the convex surface 2280 engages the corresponding one of the ramps 2244 of the bone plate 2120. This is the position depicted in FIG. 20B.

As mentioned previously, when the interbody spacer 2110 and the bone plate 2120 are secured together, the superior ramps 2224 (also referred to herein as the superior interbody spacer ramps 2224) and the ramps 2244 (also referred to herein as the superior plate member ramps 2244) may align with each other to define two continuous, superiorly-oriented ramps traversing the bone plate 2120 and the interbody spacer 2110. Similarly, the inferior ramp 2226 (also referred to herein as the inferior interbody spacer ramp 2226) and the ramp 2246 (also referred to herein as the inferior plate member ramp 2246) may align with each other to define one continuous, inferiorly-oriented ramp traversing the bone plate 2120 and the interbody spacer 2110. Thus, further posterior motion of the superior fasteners 2130 may cause the smooth, convex surface 2280 of each of the superior fasteners 2130 to move from the ramps 2244 of the bone plate 2120 to the adjoining superior ramps 2224 of the interbody spacer 2110. This motion along the ramps 2244 and the superior ramps 2224 may redirect the distal end 2262 of each of the superior fasteners 2130 from the posterior trajectory in which the superior fasteners 2130 entered the bone plate 2120, to a superior trajectory by which the superior fasteners 2130 are able to penetrate the vertebral body of the superior vertebra. This is depicted in FIG. 20C.

Figure 21A:
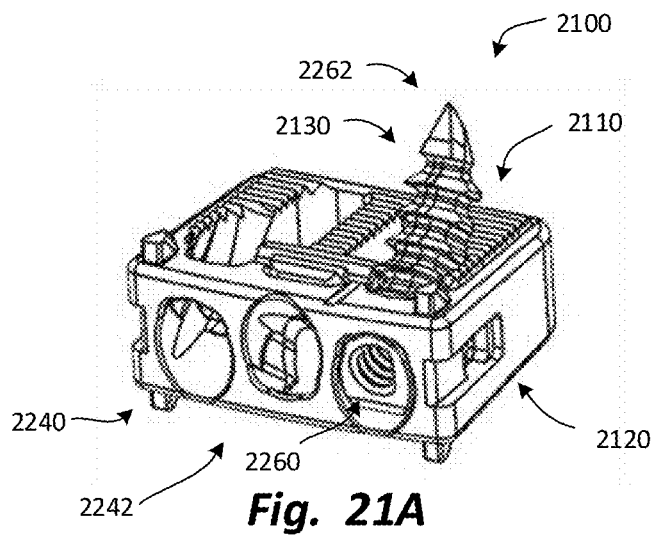
FIGS. 21A-C are perspective views of the assembly of FIGS. 14A-C depicting various states of fastener deployment.
Figure 21B:
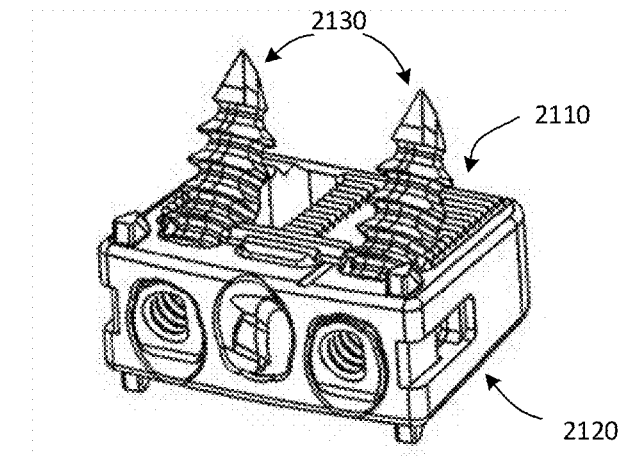
Figure 21C:
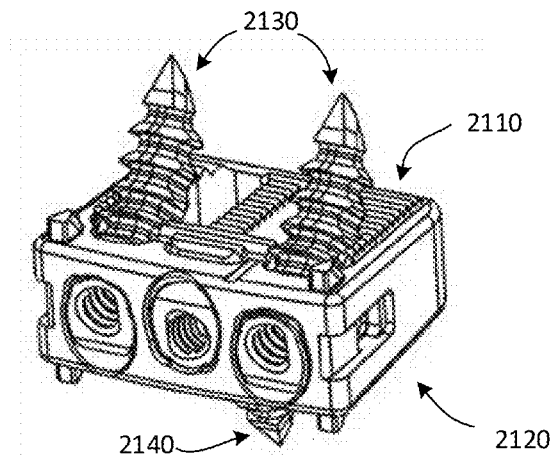

FIGS. 21A-C depict the assembly 2100, with one of the superior fasteners 2130 fully co inserted into the bone plate 2120 and the interbody spacer 2110, with both of the superior fasteners 2130 inserted, and with the superior fasteners 2130 and the inferior fastener 2140 fully inserted, respectively. As shown, the superior fasteners 2130 may be inserted into the superior fastener apertures 2240 of the bone plate 2120, and the inferior fastener 2140 may be inserted into the inferior fastener aperture 2242 of the bone plate 2120. Insertion may progress until the proximal end 2260 of each of the superior fasteners 2130 and the inferior fastener 2140 has reached, and resides within, the superior fastener apertures 2240 and the inferior fastener aperture 2242, respectively. In this position, the distal end 2262 of each of the superior fasteners 2130 and the inferior fastener 2140 may be positioned well within the vertebral body of the corresponding superior or inferior vertebra.

The superior fasteners 2130 and the inferior fastener 2140 need not be inserted sequentially as shown in FIGS. 21A-C. Rather, the superior fasteners 2130 and the inferior fastener 2140 may, in some embodiments, be inserted simultaneously, as will be further shown and described in connection with FIGS. 31B-33A.

FIGS. 22A-C depict section views, along the sagittal plane, of the assembly 2100 of FIGS. 14A-C during various stages of assembly. FIG. 22A shows how a discrete faceted curvature may be formed between one of the superior plate member ramps 2244 having a first angle in the superior direction, and a corresponding one of the superior interbody spacer ramps 2224 having a second angle in the superior direction. The first angle may be less than the second angle and the first and second angles may be chosen such that the resulting discrete faceted curvature substantially conforms to the convex curvature of the smooth, convex surface 2280 of the shank 2264 of the superior fastener 2130. In this manner, the discrete faceted curvature may facilitate sliding of the smooth, convex surface 2280 of the shank 2264 along the discrete faceted curvature. FIGS. 22B-C illustrate how the discrete faceted curvature conforms to a superior fastener 2130 once it has been inserted into the superior fastener aperture 2240 of the bone plate 2120 and protrudes out from the interbody spacer 2110.

Figure 23A:
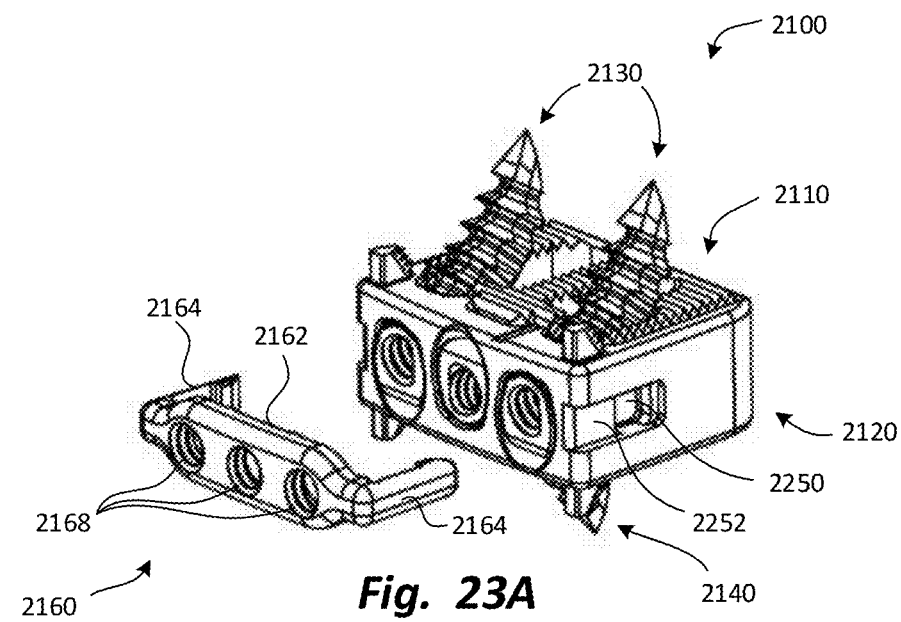
FIGS. 23A-C depict various views of the assembly of FIGS. 14A-C in relation to a locking plate.
Figure 23B:
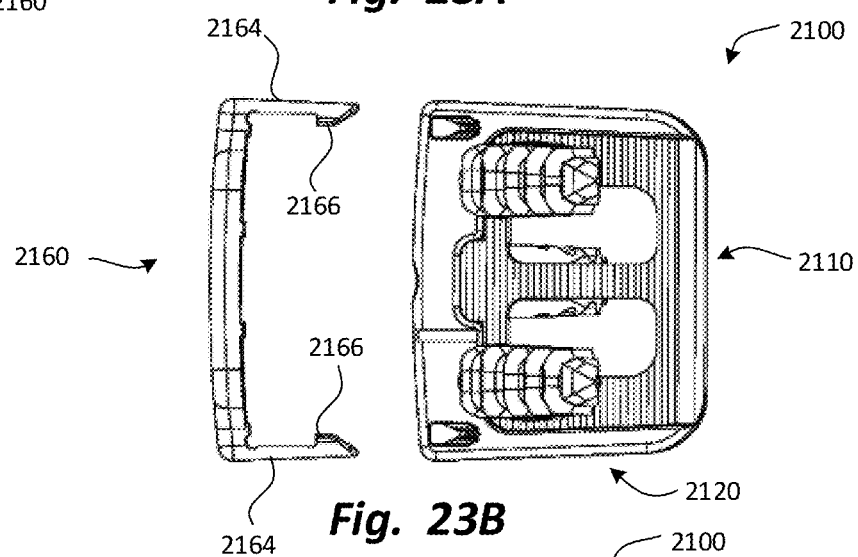
Figure 23C:
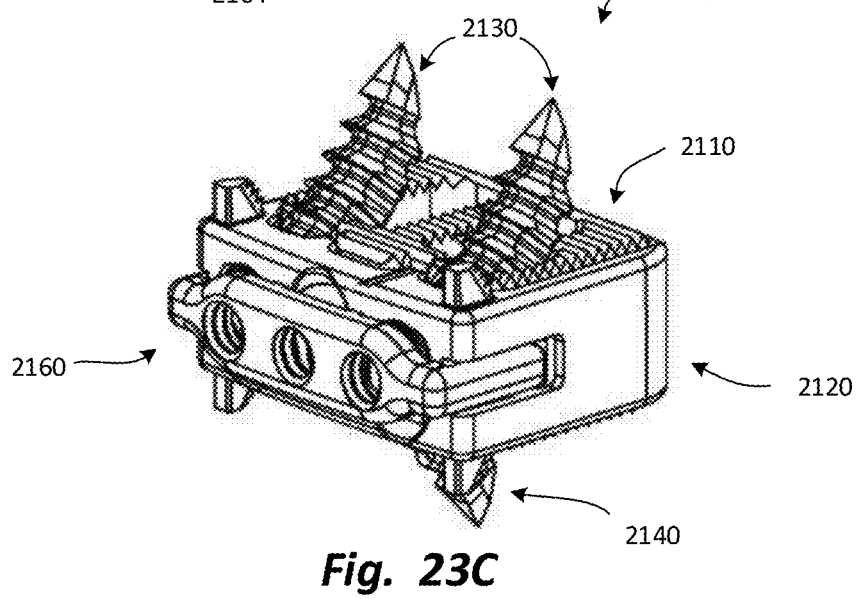
Figure 24A:
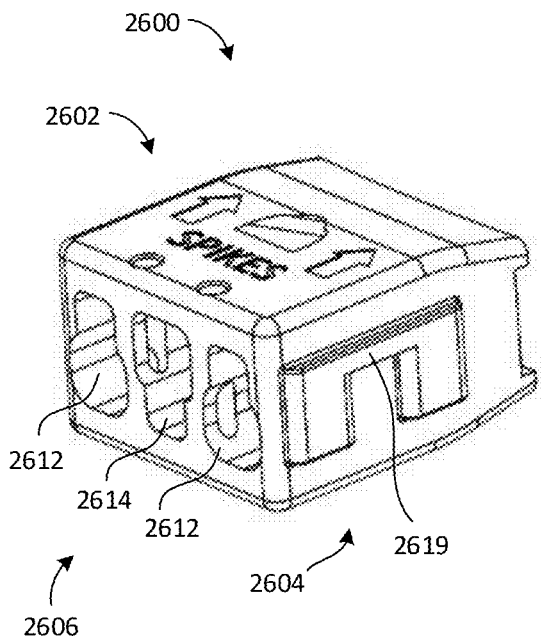
FIGS. 24A-D illustrate various views of a carriage, according to one embodiment of the present disclosure.
Figure 24B:
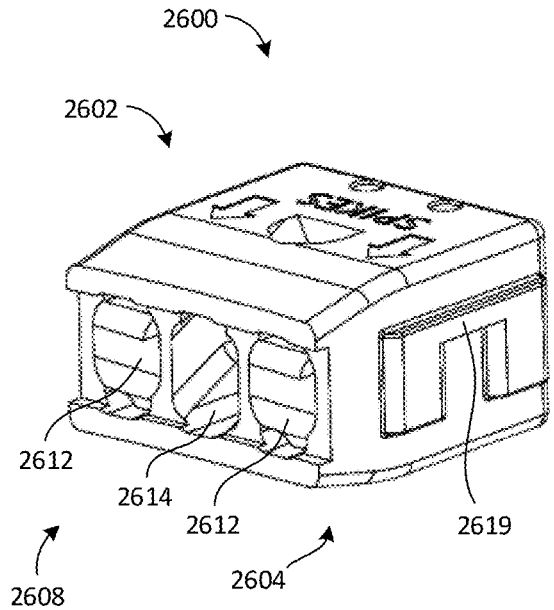
Figure 24C:
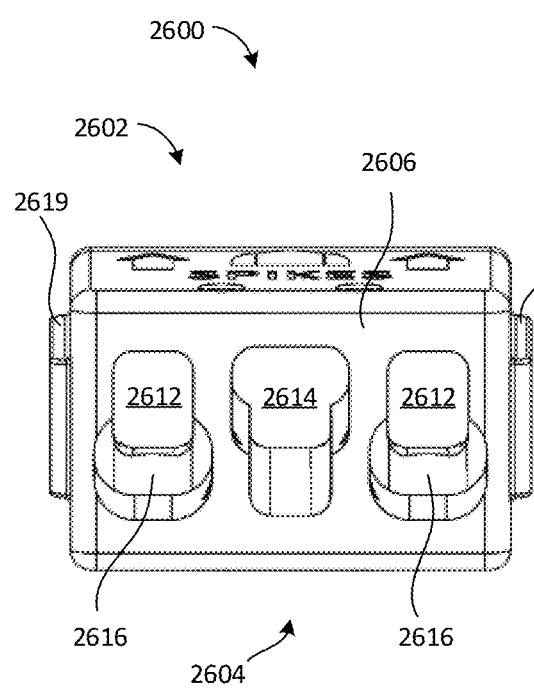
Figure 24D:
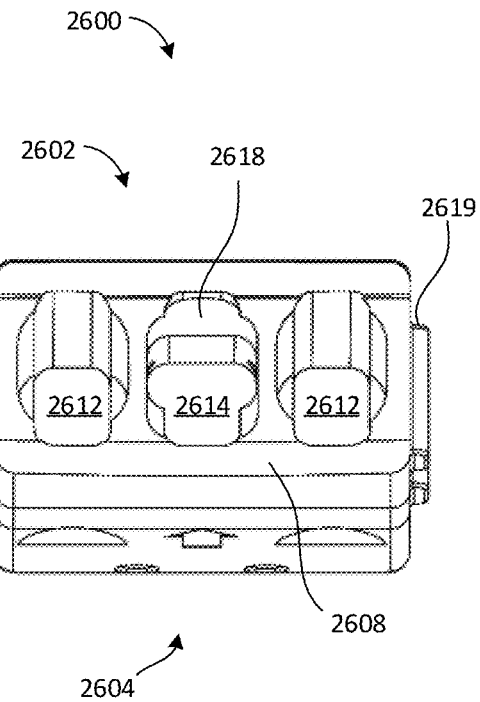

FIGS. 23A-C depict various views of the assembly 2100 of FIGS. 14A-C with a locking plate 2160. The locking plate 2160 may generally operate to prevent the fasteners from "backing out," or withdrawing over time, from the superior and/or inferior vertebrae, respectively. More co specifically, the locking plate 2160 may be removably securable to the anterior surface 2231 of the bone plate 2120 to prevent the superior fasteners 2130 and/or the inferior fastener 2140 from backing out of the superior fastener apertures 2240 and/or the inferior fastener aperture 2242, respectively, when the locking plate 2160 is coupled to the anterior surface 2231 of the bone plate 2120. The locking plate 2160 may include an anterior plate 2162 and two posteriorly extending plates 2164. The two posteriorly extending plates 2164 may further include inwardly extending tabs 2166 which may be configured to fit within the windows 2250 formed in the bone plate 2120 in order to secure the locking plate 2160 to the bone plate 2120, as can be seen in FIG. 23C. The locking plate 2160 may also include threaded apertures 2168 which may help facilitate insertion and/or removal of the locking plate 2160 from the bone plate 2120 with a suitable tool (not shown).

FIGS. 24A-D illustrate various views of a carriage 2600, according to one embodiment of the present disclosure. The carriage 2600 may include a superior end 2602, an inferior end 2604, an anterior end 2606, and a posterior end 2608. The carriage 2600 may generally be configured to house superior and/or inferior fasteners 2130, 2140. The carriage 2600 may also be configured to help align and/or guide the trajectories of the superior and/or inferior fasteners 2130, 2140 as they are urged from the carriage 2600 into a suitable implant assembly 2100 placed adjacent to the carriage 2600, as will be discussed in more detail below with reference to FIGS. 26A and 31B-33A.

The carriage 2600 may also include superior channels 2612 configured to receive superior fasteners 2130, as well as an inferior channel 2614 configured to receive an inferior fastener 2140. The superior channels 2612 and the inferior channel 2614 may be arranged with respect to a suitable assembly 2100 placed adjacent to the carriage 2600, such that the superior channels 2612 maintain the superior fasteners 2130 in alignment with the superior fastener apertures 2240 of the assembly 2100, and the inferior channel 2614 maintains the inferior fastener 2140 in alignment with the inferior fastener aperture 2242 of the implant assembly 2100. For example, each different implant assembly 2100 size may have a different height, width, and/or depth (i.e., footprint). Accordingly, different carriage 2600 sizes with similar heights, widths, and/or depths that correspond to a given assembly 2100 size may be utilized. In this manner, the superior channels 2612 of a correspondingly sized carriage 2600 may maintain the superior fasteners 2130 in alignment with the superior fastener apertures 2240 of the assembly 2100, and the inferior channel 2614 may also maintain the inferior fastener 2140 in alignment with the inferior fastener aperture 2242 of the implant assembly 2100. Moreover, the spacing and arrangement of the superior channels 2612 and/or the inferior channel 2614 for each carriage 2600 size, corresponding to a given implant assembly 2100 size, may be configured such that each differently sized carriage 2600 and its correspondingly sized implant assembly 2100 may be received by a single inserter tool, as will be discussed in more detail with respect to FIGS. 27-33A. The superior channels 2612 may also include superiorly angled ramps 2616 configured to help guide the trajectories of the superior fasteners 2130 as the superior fasteners 2130 are urged from the carriage 2600 into the implant assembly 2100, and the inferior channel 2614 may also include an inferiorly angled ramp 2618 configured to help guide a trajectory of the inferior fastener 2140 as the inferior fastener 2140 is urged from the carriage 2600 into the implant assembly 2100, as will be shown in more detail with reference to FIGS. 26A-B. The carriage 2600 may also include engagement features 2619 that may engage complementary shaped features formed in an inserter to help keep the carriage 2600 in place relative to the inserter, as will be discussed in more detail below with reference to FIGS. 27-30B.

Figure 25A:
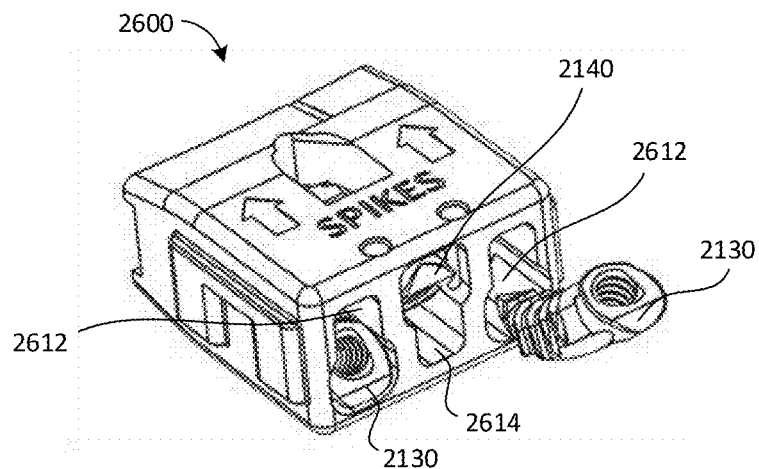
FIGS. 25A-C are perspective views of the carriage of FIGS. 24A-D showing various stages of fastener insertion into the carriage.
Figure 25B:
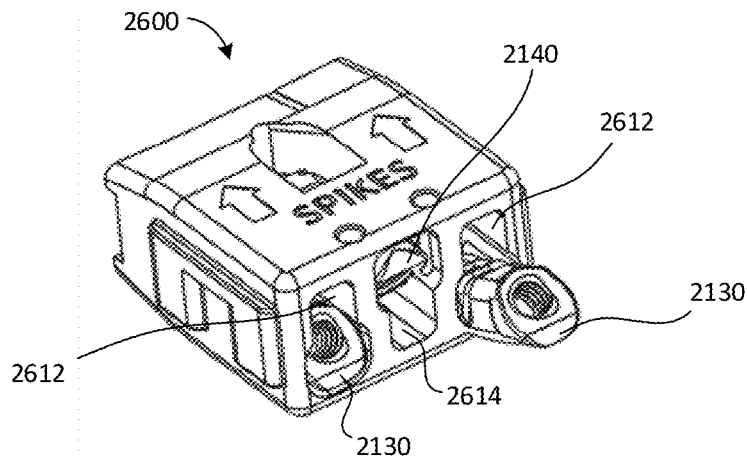
Figure 25C:
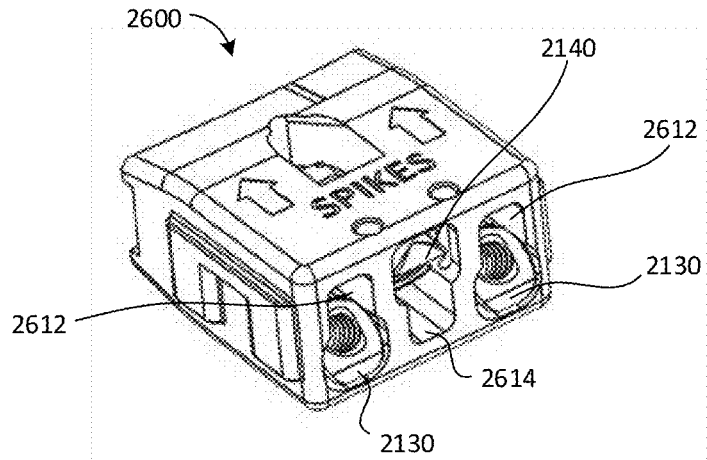

FIGS. 25A-C are perspective views of the carriage 2600 of FIGS. 24A-D showing various stages of fastener insertion into the carriage 2600. In this manner, the fasteners 2130, 2140 may be pre-loaded into the carriage 2600 before the carriage 2600 is coupled to a suitable inserter, as will be discussed with reference to FIGS. 30A-B. FIGS. 25A-C illustrate the carriage 2600 with one superior fastener 2130 loaded into one of the superior channels 2612, an inferior fastener 2140 loaded into the inferior channel 2614, and another superior fastener 2130 in various stages of being loaded into the other superior channel 2612 in FIGS. 25A-C.

Figure 26A:
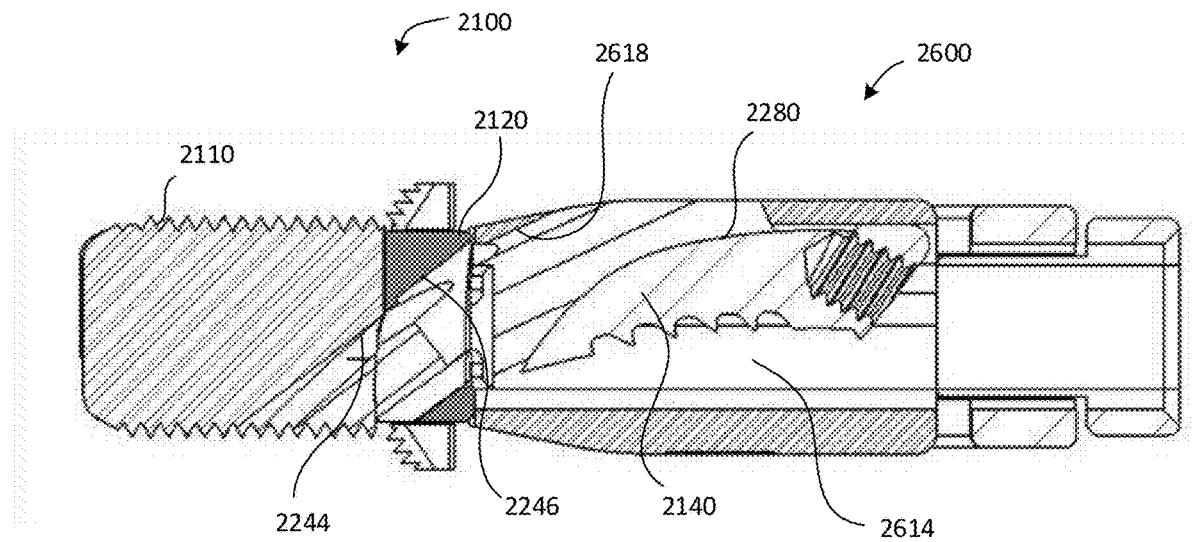
FIGS. 26A-B are section views, along the sagittal plane, of the assembly of FIGS. 14A-C coupled to the loaded carriage 2600 of FIG. 25C at various stages of fastener deployment.
Figure 26B:
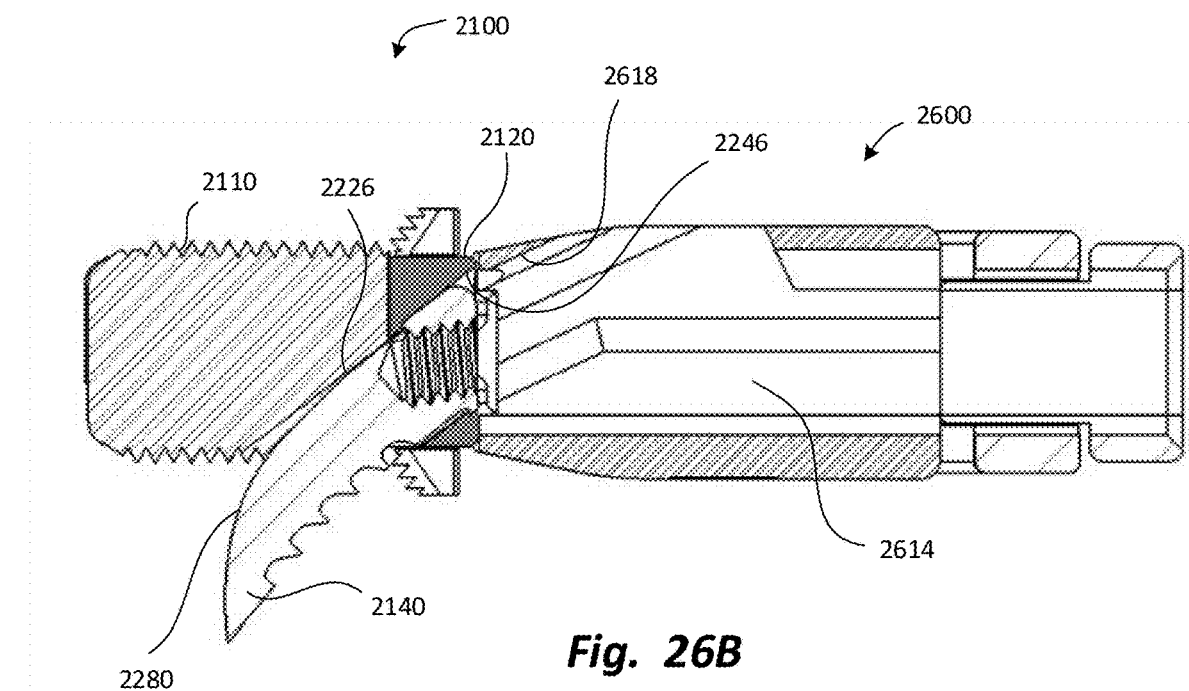

FIGS. 26A-B depict section views, along the sagittal plane, of the assembly 2100 of FIGS. 14A-C coupled to the loaded carriage 2600 of FIG. 25C, at various stages of deploying the inferior fastener 2140. In FIG. 26A, the inferior fastener 2140 is shown residing within the inferior channel 2614 of the carriage 2600 prior to deployment. The inferior fastener 2140 may then be urged toward the implant assembly 2100 and away from the carriage 2600, such that the smooth, convex surface 2280 of the inferior fastener 2140 may contact and slide along the inferiorly angled ramp 2618 located within the inferior channel 2614, the inferior plate member ramp 2246 located within the bone plate 2120, and the inferior interbody spacer ramp 2226 located within the interbody spacer 2110. FIG. 26B shows the inferior fastener 2140 after it has been fully deployed.

In at least one embodiment, the inferiorly angled ramp 2618 of the carriage 2600 may have a first angle that is less than a second angle of the inferior plate member ramp 2246 of the bone plate 2120, and the second angle of the inferior plate member ramp 2246 of the bone plate 2120 may be less than a third angle of the inferior interbody spacer ramp 2226 of the interbody spacer 2110. In this manner, a single large ramp may be formed from each of these smaller ramps that are abutted together against each other. This single large ramp may have a three part discrete faceted curvature which may be further configured to substantially conform to the smooth, convex surface 2280 of the inferior fastener 2140 to facilitate sliding of the smooth, convex surface 2280 of the inferior fastener 2140 along the three part discrete faceted curvature of the large ramp.

Figure 27:
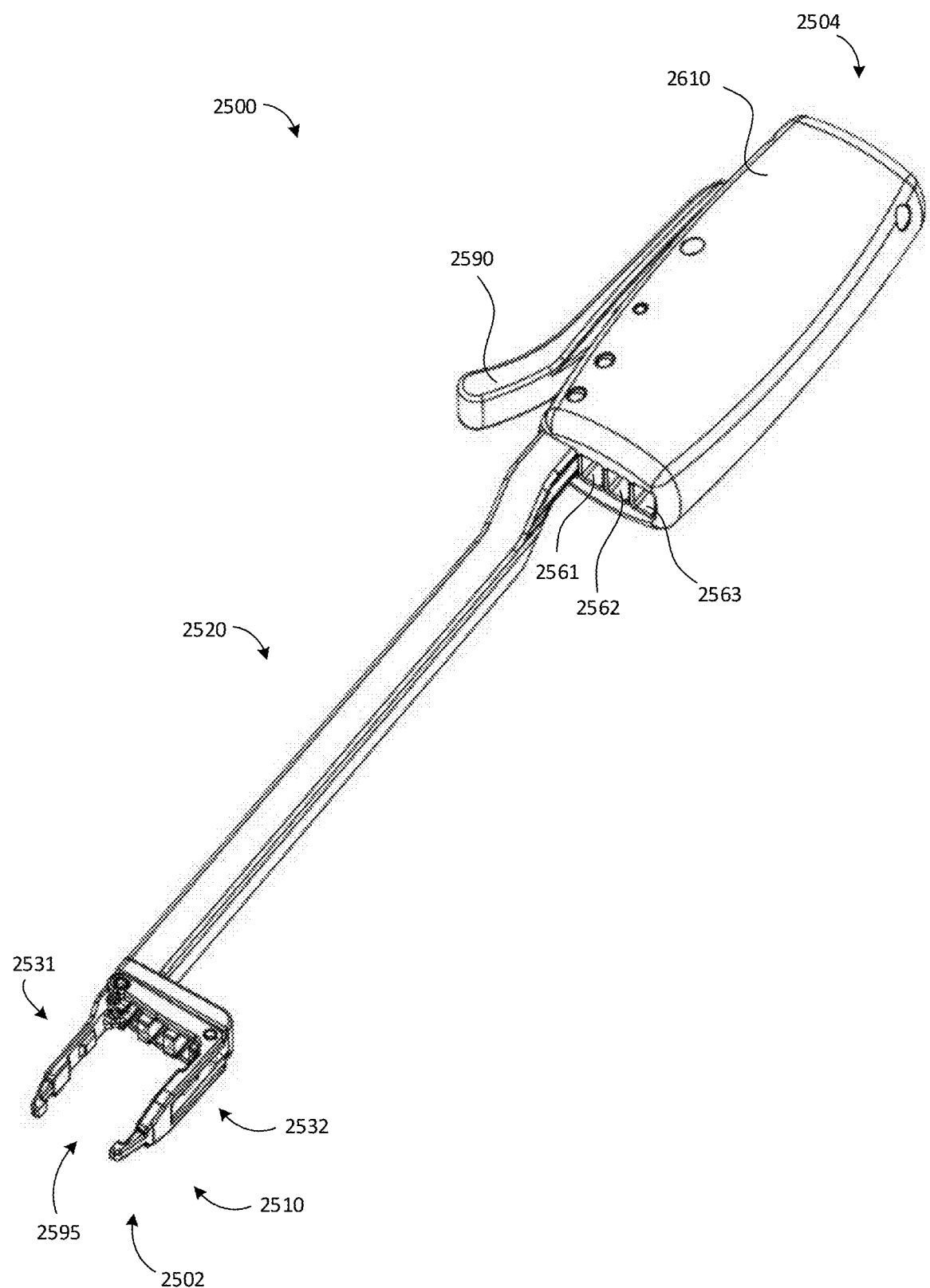
FIG. 27 is a top perspective view of an inserter, according to another embodiment of the present disclosure.
Figure 28:
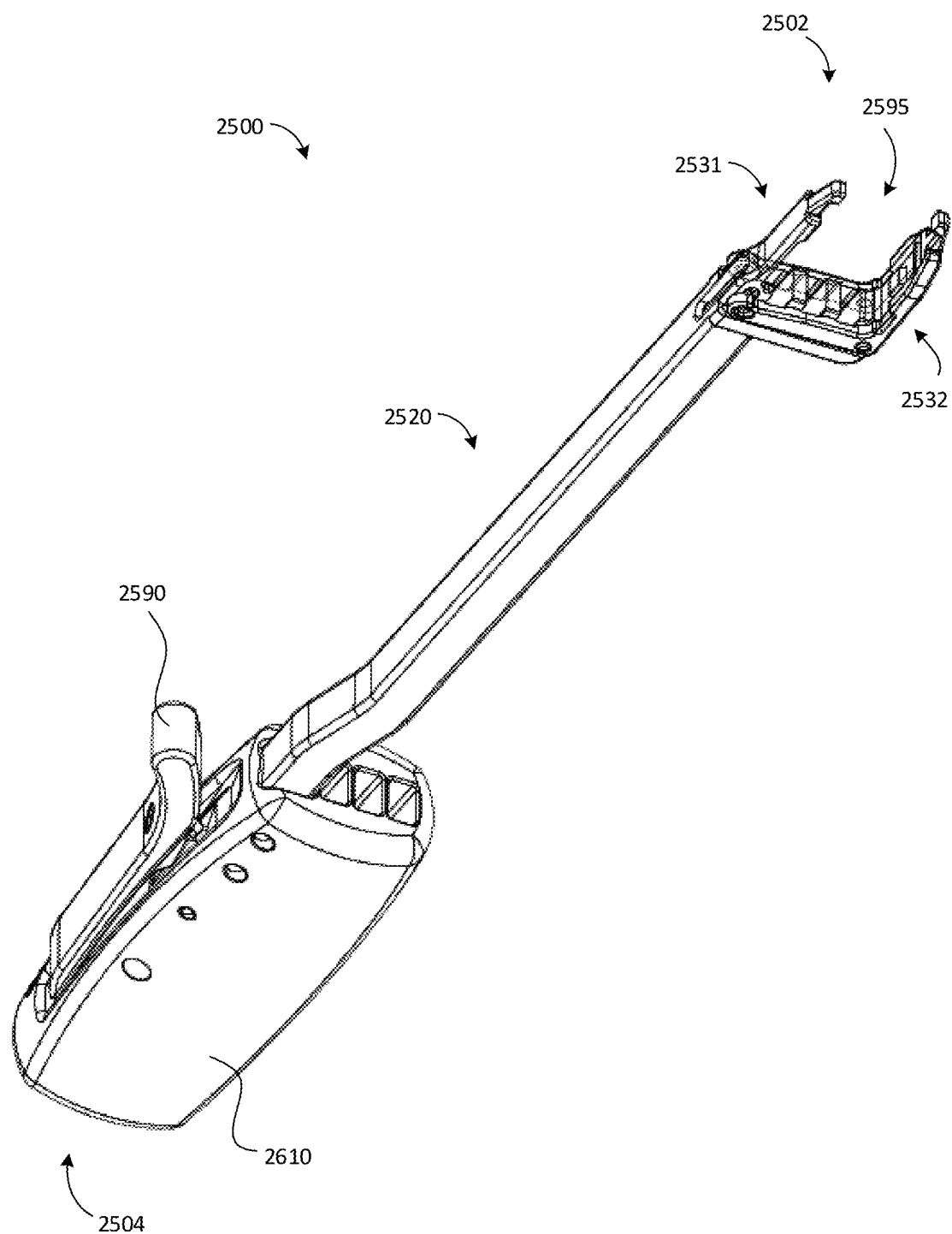
FIG. 28 is a bottom perspective view of the inserter of FIG. 27.

FIGS. 27-33A show various views of an inserter 2500 that may facilitate insertion and positioning of the assembly 2100, and also aid in deployment of the superior fasteners 2130 and the inferior fastener 2140, according to another embodiment of the present disclosure. FIG. 27 shows a top perspective view of the inserter 2500, FIG. 28 shows a bottom perspective view of the inserter 2500, FIG. 29A shows an anterior perspective view of the inserter 2500, and FIG. 29B shows a bottom perspective view of the head 2510 of the inserter 2500.

The inserter 2500 may generally include a handle 2610 at a proximal end 2504 of the inserter 2500, a quick release lever 2590 coupled to the handle 2610, a head 2510 at a distal end 2502 of the inserter 2500, and a shank 2520 intermediate the proximal end 2504 and the distal end 2502 of the inserter 2500. The head 2510 may further include a first implant retention arm 2531, a second implant retention arm 2532, and a carriage housing space 2595 located intermediate the first and second implant retention arms 2531, 2532 distal to the shank 2520 of the inserter 2500.

The first and second implant retention arms 2531, 2532 may be configured to engage co opposing sides of an implant, such as the implant assembly 2100 of FIGS. 14A-C, to removably couple the implant assembly 2100 to the head 2510 of the inserter 2500. The first and second implant retention arms 2531, 2532 may also be configured to engage opposing sides of a carriage 2600 and/or a drill guide 2650 to removably couple, or removably secure, the carriage 2600 and/or drill guide 2650 to the head 2510 of the inserter 2500, as will be discussed in more detail below.

Figure 31A:
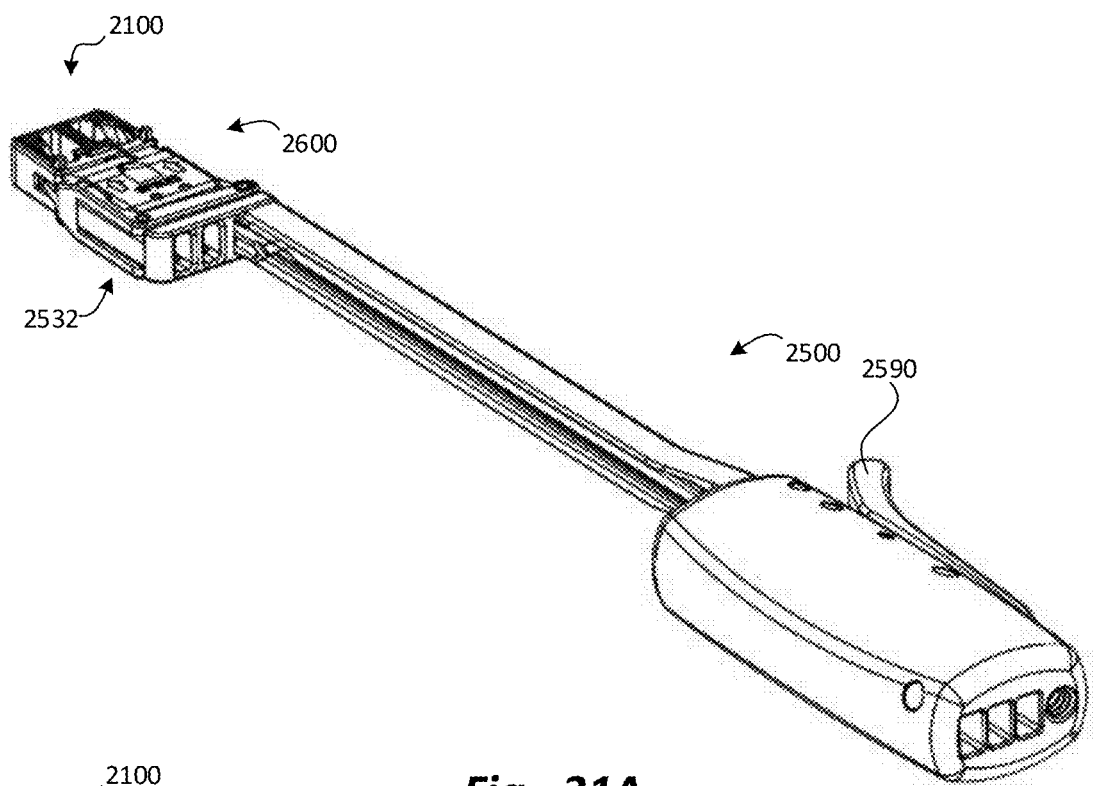
FIG. 31A is a perspective view of the inserter of FIG. 27 coupled to the carriage of FIGS. 24A-D and further coupled to the assembly of FIGS. 14A-C.
Figure 31B:
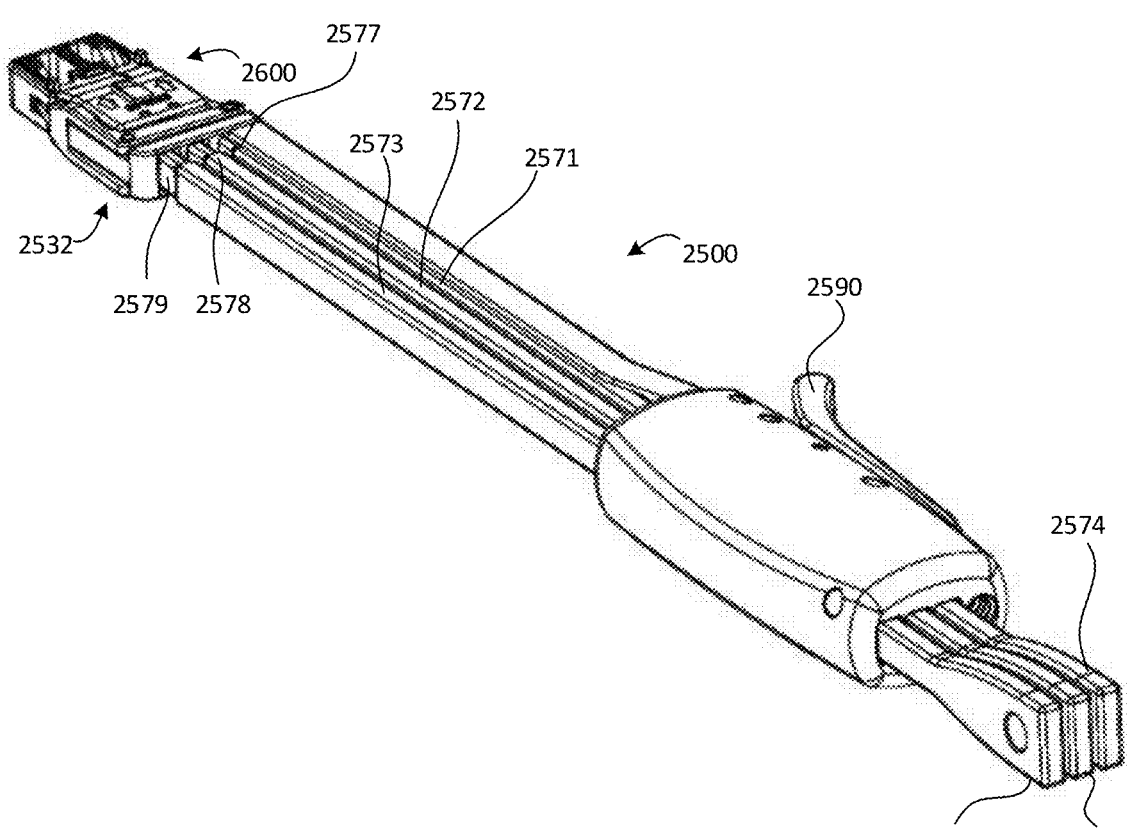
FIG. 31B is a perspective view of the inserter of FIG. 31A further coupled to three drivers.
Figure 33A:
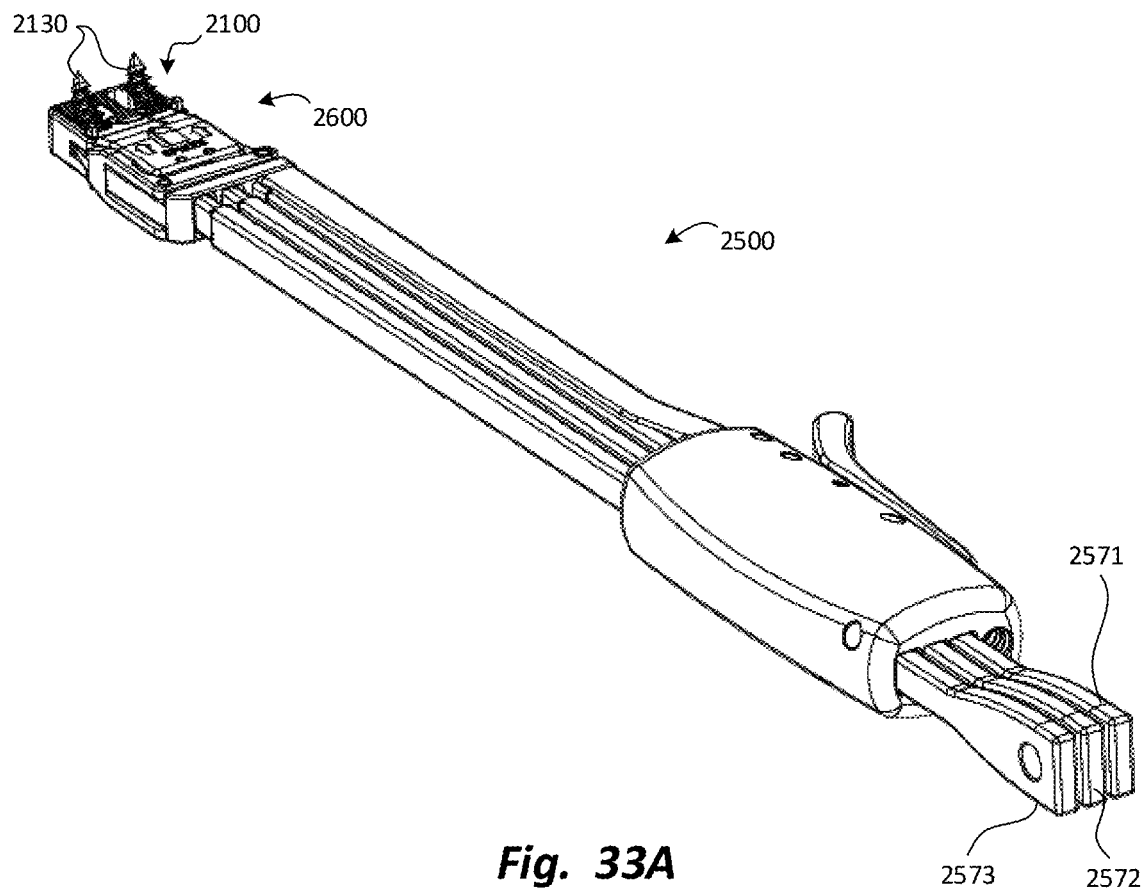
FIG. 33A is a perspective view of the inserter of FIG. 31B showing fully deployed fasteners.

The handle 2610 of the inserter 2500 may include a first driver retention feature 2561, a second driver retention feature 2562, and a third driver retention feature 2563. The head 2510 of the inserter 2500 may also include a corresponding first driver retention feature 2551, a second driver retention feature 2552, and a third driver retention feature 2553, respectively. These driver retention features may together receive a first driver 2571, a second driver 2572, and a third driver 2573, as can be seen in FIGS. 31B and 33A. The first, second, and third drivers may each have proximal ends 2574, 2575, 2576, respectively, and distal ends 2577, 2578, and 2579, respectively. The first, second, and third driver retention features 2561, 2562, 2563, 2551, 2552, 2553 may each be configured to engage the first, second, and third drivers 2571, 2572, 2573, respectively, between their distal ends 2577, 2578, 2579 and their proximal ends 2574, 2575, 2576, in order to guide the motion of each of the first, second, and third drivers 2571, 2572, 2573. Each of the proximal ends 2574, 2575, 2576 may also be exposed to permit the proximal ends 2574, 2575, 2576 to directly receive an impact to urge the drivers 2571, 2572, 2573 toward the superior channels and the inferior channel of the carriage 2600 to urge the superior fasteners 2130 toward the superior fastener apertures 2240 and the inferior fastener 2140 toward the inferior fastener aperture 2242.

Figure 29A:
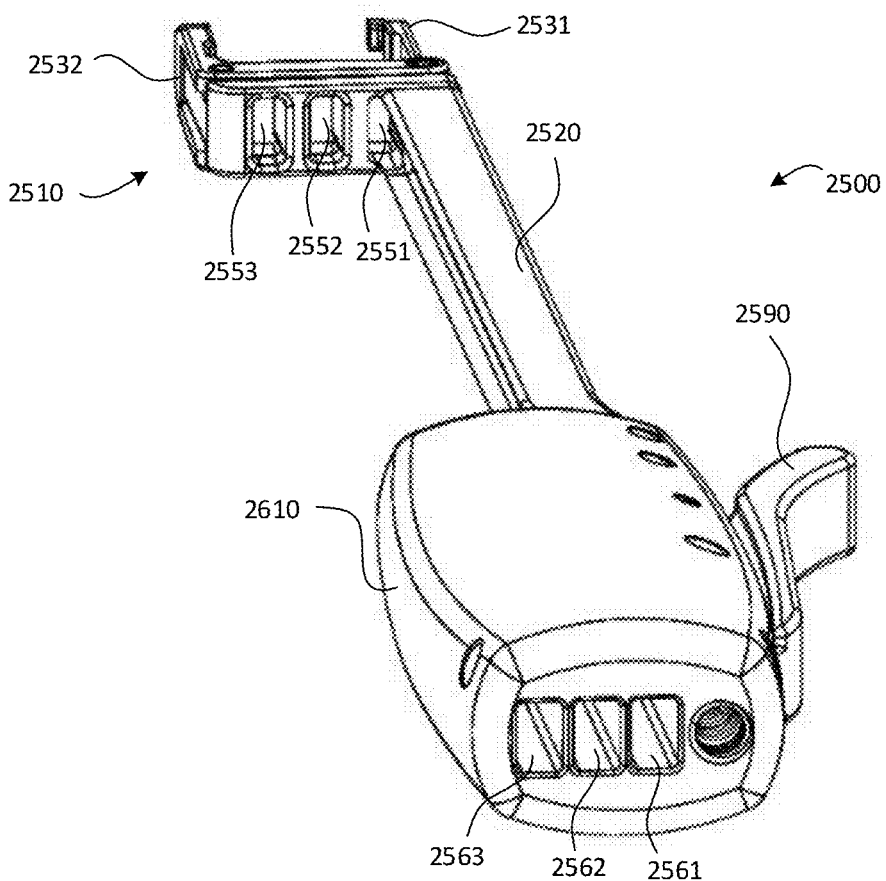
FIG. 29A is an anterior perspective view of the inserter of FIG. 27.
Figure 29B:
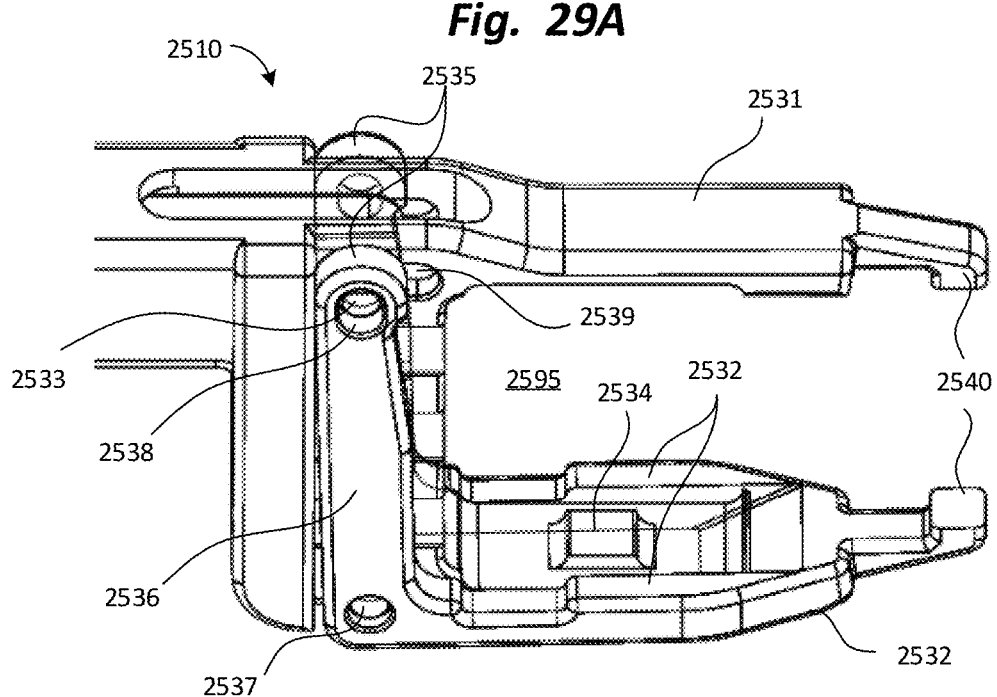
FIG. 29B is a bottom perspective view of the head of the inserter of FIG. 27.

FIG. 29B shows an enlarged perspective view of the head 2510 of the inserter 2500. The implant assembly 2100, carriage 2600, and/or drill guide 2650 may each be removably coupled to the head 2510 of the inserter 2500 by opening and/or closing the second implant retention arm 2532 with respect to the first implant retention arm 2531. This may be accomplished by selectively actuating the quick release lever 2590 to open and/or close the second implant retention arm 2532. However, it will be understood that other embodiments may use any number of different suitable mechanisms, such as a rotating knob (not shown) as one non-limiting example, in place of the quick release lever 2590 to open and/or close the second implant retention arm 2532.

The second implant retention arm 2532 may include actuation arms 2536 rigidly affixed to the second implant retention arm 2532. The actuation arms 2536 may be pivotally connected to the head 2510 of the inserter 2500 at a pivot point 2537. The distal ends 2535 of the actuation arms 2536 may include first cam-shaped apertures 2538 which may be coupled to second cam-shaped apertures 2539 formed in the first implant retention arm 2531 via a free-floating pin 2533 that fits within the first and second cam-shaped apertures 2538, 2539. In this manner, actuating the quick release lever 2590 in a first direction causes a push member (not shown) to move distally, pushing the free-floating pin 2533 distally, moving the actuation arms 2536 distally about the pivot point 2537, and causing the second implant retention arm 2532 to open with respect to the first implant retention arm 2531. Likewise, actuating the quick release lever 2590 in a second direction causes the push member (not shown) to move proximally, pulling the free-floating pin 2533 proximally, moving the actuation arms 2536 proximally about the pivot point 2537, and causing the second implant retention arm 2532 to close with respect to the first implant retention arm 2531.

The first and second implant retention arms 2531, 2532 may also include inwardly-extending tabs 2540 that may extend into correspondingly shaped windows 2250 formed in the bone plate 2120 of the implant assembly 2100 when the first and second implant retention arms 2531, 2532 are positioned in the grooves 2252 formed in the bone plate 2120 of the implant assembly 2100 that extend from the anterior end 2230 of the bone plate 2120 to the windows 2250. In this manner, the first and second implant retention arms 2531, 2532 may engage opposing sides of the implant assembly 2100 and removably couple the implant assembly 2100 to the head 2510 of the inserter 2500.

Likewise, at least one of the implant retention arms 2531, 2532 may include inwardly extending tabs 2534 and or shelves 2542 configured to interact with complementary shaped engagement features 2619, 2669 formed on the carriage 2600 and/or drill guide 2650, respectively, in order to removably couple the carriage 2600 and/or drill guide 2650 to the head 2510 of the inserter 2500 within the carriage housing space 2595.

Figure 30A:
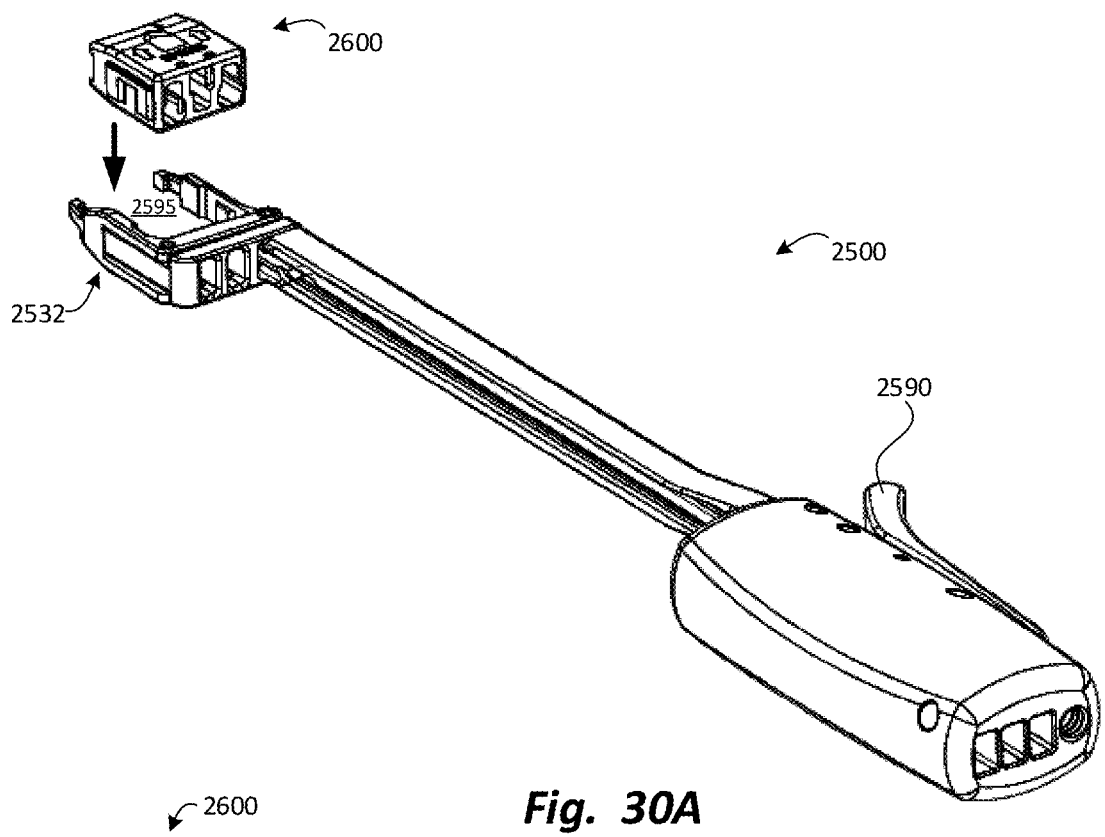
FIG. 30A is a perspective view of the inserter of FIG. 27 with the carriage of FIGS. 24A-D.
Figure 30B:
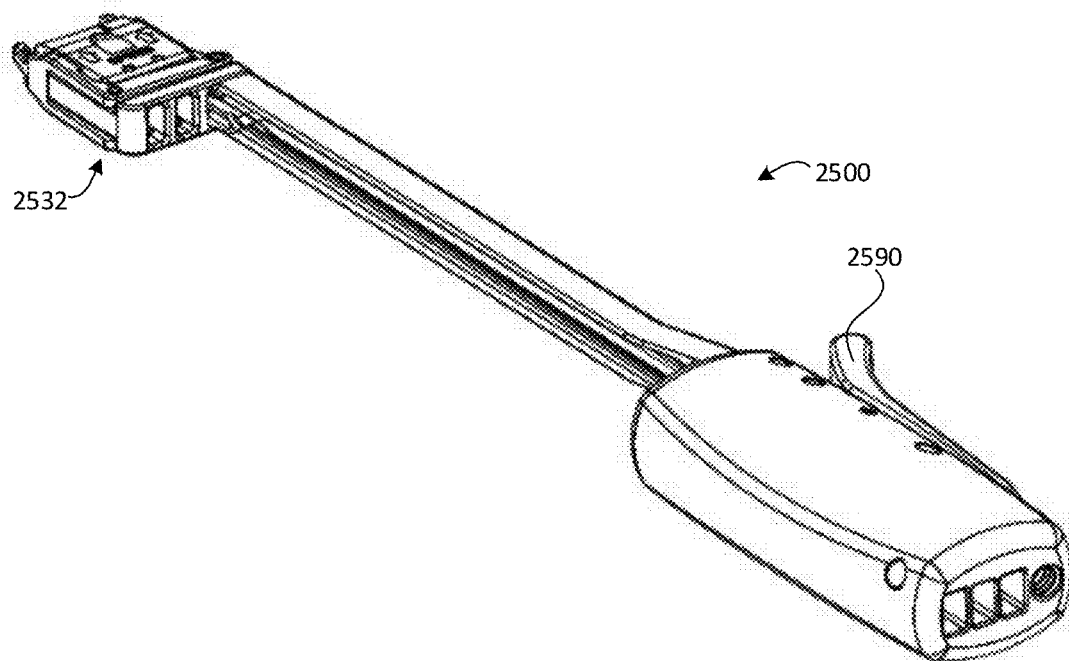
FIG. 30B is a perspective view of the inserter of FIG. 27 coupled to the carriage of FIGS. 24A-D.

For example, FIG. 30A shows a perspective view of the inserter 2500 of FIG. 27 with the loaded carriage 2600 placed above the carriage housing space 2595. The second implant retention arm 2532 may be opened by actuating the quick release lever 2590 in a first direction. The carriage 2600 may then be moved inferiorly into the carriage housing space 2595 of the inserter 2500. The second implant retention arm 2532 may then be closed by actuating the quick release lever 2590 in a second direction in order to couple the carriage 2600 to the head 2510 of the inserter 2500, as can be seen in FIG. 30B.

Once the loaded carriage 2600 is coupled to the head 2510 of the inserter 2500, a suitable implant assembly 2100 may be coupled to the distal end of the head 2510 of the inserter 2500. For example, FIG. 31A shows a perspective view of the inserter 2500 coupled to a carriage 2600 and to an implant assembly 2100. To achieve this configuration, the implant assembly 2100 may be placed distal to the inserter 2500 and to the carriage 2600. The second implant retention arm 2532 may then be opened by actuating the quick release lever 2590 in a first direction. The implant assembly 2100 may then be moved proximally to abut the proximal end of the implant assembly 2100 with the distal end of the carriage 2600, such that the implant assembly 2100 is also intermediate the first and second implant retention arms 2531, 2532. The second implant retention arm 2532 may then be closed by actuating the quick release lever 2590 in a second direction in order to engage opposing sides of the implant assembly 2100 with the first and second implant retention arms 2531, 2532 in order to couple the implant assembly 2100 to the head 2510 of the inserter 2500 (see FIGS. 31A-B).

Once the loaded carriage 2600 and the suitable implant assembly 2100 are coupled to the head 2510 of the inserter 2500, the inserter 2500 may then be coupled to a first driver 2571, a second driver 2572, and/or a third driver 2572, as shown in FIG. 31B. The fasteners loaded inside of the carriage 2600 may then be urged out of the carriage 2600, through the implant assembly 2100, and into a superior and/or inferior vertebra by driving the first, second, and/or third drivers 2571, 2572, 2573 to deploy one of the corresponding fasteners. This may be accomplished by inserting each of the first, second, and third driver distal ends 2574, 2575, 2576 into corresponding superior channels 2612 and/or inferior channels 2614 of the carriage 2600 until these driver distal ends 2574, 2575, 2576 abut the proximal ends of the superior fasteners 2130 and/or inferior fastener 2140 that are loaded within the carriage 2600.

Figure 32A:
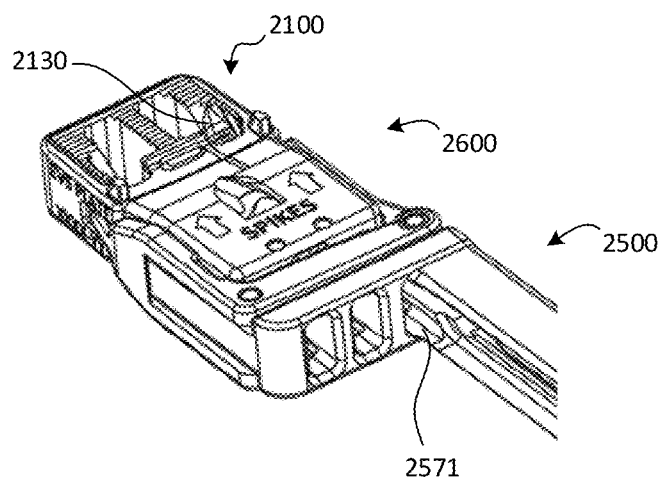
FIGS. 32A-C are perspective views of the distal end of the inserter of FIG. 31B depicting various stages of fastener deployment.
Figure 32B:
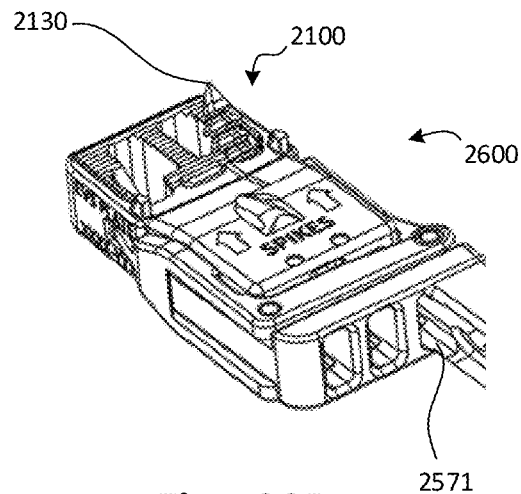
Figure 32C:
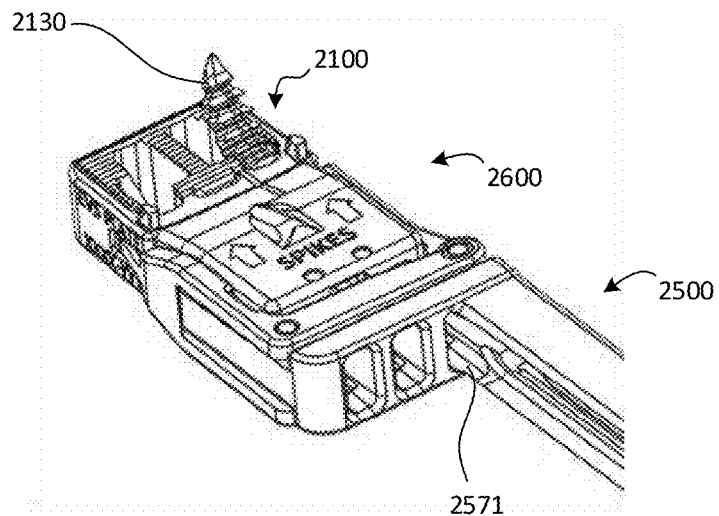

For example, FIGS. 32A-C are perspective views of the head 2510 of the inserter 2500 showing various stages of deploying a superior fastener 2130. As the first driver 2571 is moved distally, by applying a force to the first driver 2571 with a suitable tool such as a mallet (not shown), the superior fastener 2130 is also driven distally by the driver from the carriage and into the implant assembly 2100. This can be seen in FIGS. 32A-C showing the superior fastener 2130 being urged from the carriage 2600, into the implant assembly 2100, and then eventually achieving full deployment, as shown in FIG. 32C.

This deployment process may be done in sequence, by sequentially driving one of the first, second, and/or third drivers 2571, 2572, 2573 individually. Alternatively, this deployment process may be performed simultaneously by driving each of the first, second, and/or third drivers 2571, 2572, 2573 simultaneously, to simultaneously urge a first superior fastener, a second superior fastener, and an inferior fastener to move distally until they are fully deployed, as can be seen in FIG. 33A.

With the superior fasteners 2130 and the inferior fastener 2140 fully advanced, the head 2510 of the inserter 2500 may be detached from the implant assembly 2100. In some embodiments, the head 2510 may be able to be pulled anteriorly free of the implant assembly 2100. Due to the engagement of the superior fasteners 2130 and the inferior fastener 2140 with the superior and inferior vertebrae, respectively, the implant assembly 2100 may remain lodged between the vertebrae. The anterior force on the head 2510 may cause the implant retentions arms 2531, 2532 of the head 2510 to spread, allowing the inwardly-extending tabs 2540 to pull free of the windows 2250 of the bone plate 2120 so that the head 2510 can be detached from the implant assembly 2100. The disposition of the implant assembly 2100 will be shown and described in connection with FIGS. 33A-B, as follows.

Figure 33B:
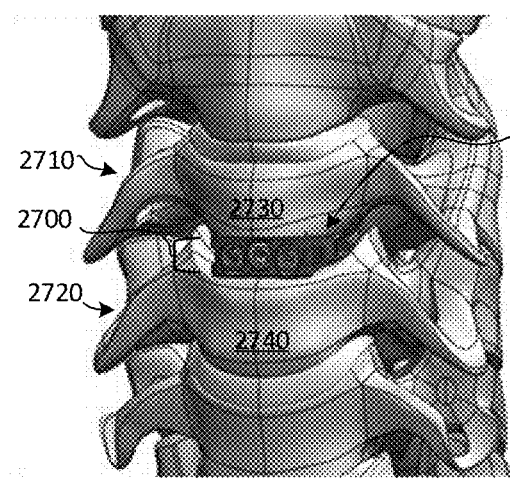
FIGS. 33B-C depict the assembly of FIGS. 14A-C implanted within an intervertebral space.
Figure 33C:
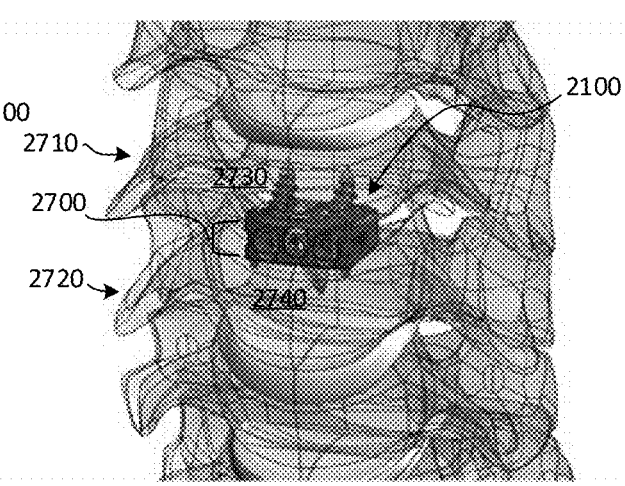
Figure 35A:
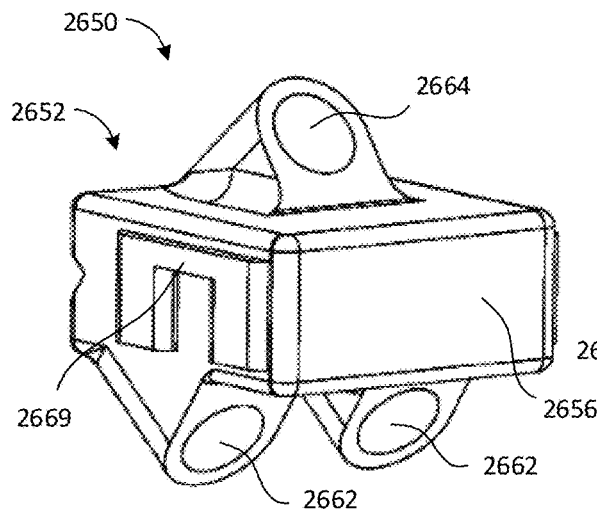
FIGS. 35A-D illustrate various views of a drill guide, according to one embodiment of the present disclosure.
Figure 35B:
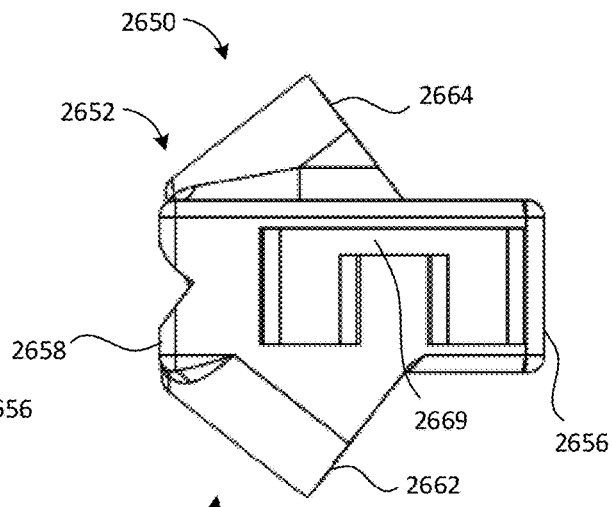
Figure 35C:
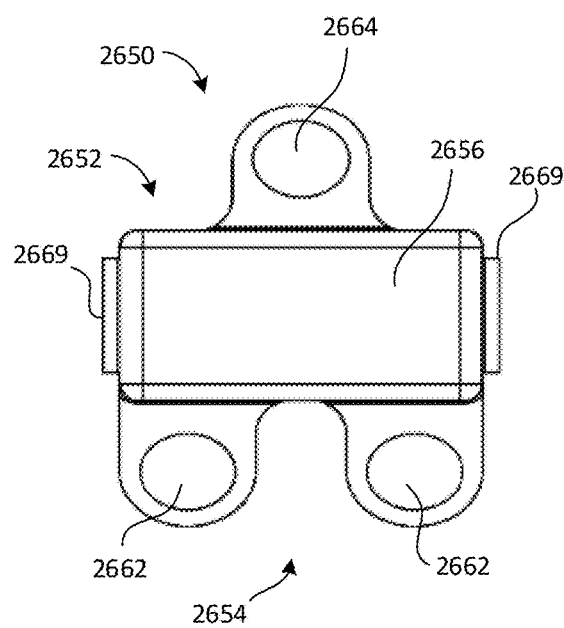
Figure 35D:
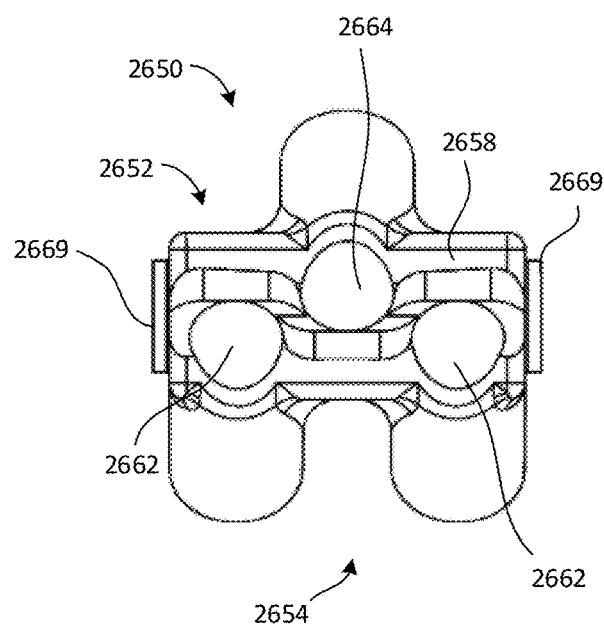

FIGS. 33A-B depict the implant assembly 2100 of FIGS. 14A-C implanted within an intervertebral space 2700 in its fully assembled state, with the superior fasteners 2130 and the inferior fastener 2140 deployed to retain the assembly 2100 within the intervertebral space 2700 between a superior vertebra 2710 and an inferior vertebra 2720. As shown in FIG. 33B, the superior fasteners 2130 extend into a superior vertebral body 2730 of the superior vertebra 2710, and the inferior fastener 2140 extends into an inferior vertebral body 2740 of the inferior vertebra 2720.

Notably, the interbody spacer 2110 and the bone plate 2120 may cooperate to stabilize the joint between the superior vertebra 2710 and the inferior vertebra 2720. Specifically, the interbody spacer 2110 may help restrict compression of the intervertebral space 2700, and the bone plate 2120 may help ensure that the intervertebral space 2700 does not widen excessively and may help retain the interbody spacer 2110 in place between the superior vertebral body 2730 and the inferior vertebral body 2740. As mentioned previously, bone graft or other substances may be inserted into the interior cavities 2212 of the interbody spacer 2110 to encourage the growth of a column of bone through the interior cavities 2212, connecting the superior vertebral body 2730 to the inferior vertebral body 2740. The interbody spacer 2110 and the bone plate 2120 may keep the joint immobilized to permit growth of such a column. As mentioned previously, the interbody spacer 2110 and the bone plate 2120 may, in some embodiments, be used independently of each other. In such cases, the interbody spacer 2110 and/or the bone plate 2120 (with the superior fasteners 2130 and/or the inferior fastener 2140) may provide sufficient fixation, independently, to permit formation of bone to fuse the two adjacent vertebral bodies together.

As mentioned previously, various forms of fixation may be used to secure the implant assembly 2100 to a vertebral body. For example, FIGS. 34A-C show superior bone screws 2131 and an inferior bone screw 2141 that may be used in conjunction with the implant assembly 2100 in place of the superior spike fasteners 2130 and inferior spike fastener 2140, as previously discussed. However, it will be noted that any number of superior and/or inferior bone screws 2131, 2141 may be used with any number of superior and/or inferior spike fasteners 2130, 2140 in any arrangement, number, or configuration with the implants disclosed herein.

FIGS. 35A-D illustrate various views of a drill guide 2650, according to one embodiment of the present disclosure, which may facilitate fixation of the superior and/or inferior bone screws 2131, 2141 within a superior and/or inferior vertebra. The drill guide 2650 may have a superior end 2652, an inferior end 2654, a proximal end 2656, and a distal end 2658. The superior end 2652 may include an inferior drill guide aperture 2664 and the inferior end 2654 may include superior drill guide apertures 2662. The drill guide apertures 2662, 2664 may each define drill guide angled ramps 2651 therein configured to guide a trajectory of a tool 2670 and/or a bone screw, as will be discussed below in more detail with reference to FIGS. 37A-38B. The sides of the drill guide 2650 may also include retaining features 2669 that may be configured to couple the drill guide 2650 to the head 2510 of the inserter 2500 in a similar fashion to the carriage 2600, as previously discussed.

Figure 36A:
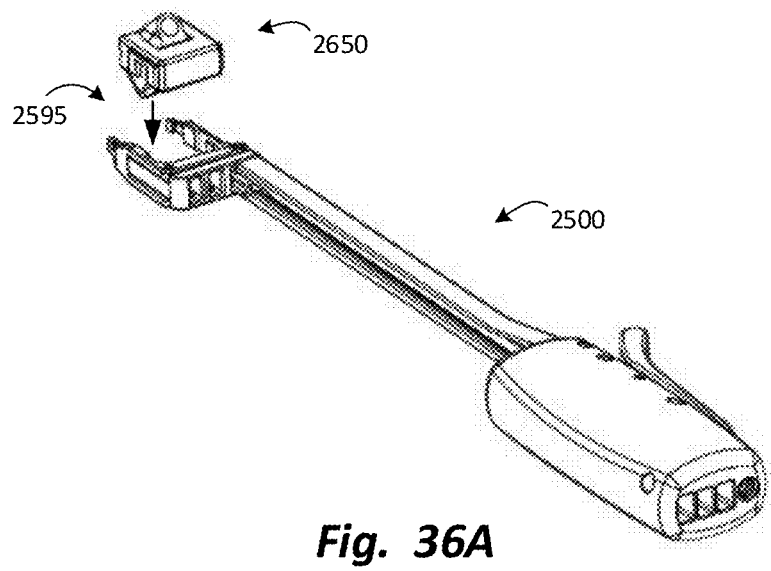
FIG. 36A is a perspective view of the inserter of FIG. 27 with the drill guide of FIGS. 35A-D.
Figure 36B:
FIG. 36B is a perspective view of the inserter of FIG. 36A coupled to the drill guide of FIGS. 35A-D.

For example, FIGS. 36A-B illustrate perspective views of the inserter 2500 of FIG. 27 with the drill guide 2650 placed above the carriage housing space 2595. The second implant retention arm 2532 may be opened by actuating the quick release lever 2590 in a first direction. The drill guide 2650 may then be moved inferiorly into the carriage housing space 2595 of the inserter 2500. The second implant retention arm 2532 may then be closed by actuating the quick release lever 2590 in a second direction in order to couple the drill guide 2650 to the head 2510 of the inserter 2500, as can be seen in FIG. 36B.

Figure 36C:
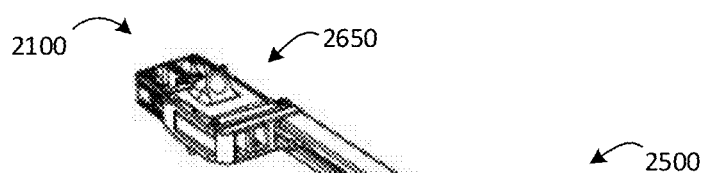
FIG. 36C is a perspective view of the inserter of FIG. 36B coupled to the drill guide of FIGS. 35A-D and further coupled to the assembly of FIGS. 34A-C.

Once the drill guide 2650 is coupled to the head 2510 of the inserter 2500, a suitable implant assembly 2100 may then be coupled to the distal end of the head 2510 of the inserter 2500. For example, FIG. 36C shows a perspective view of the inserter 2500 coupled to a drill guide 2650 and to an implant assembly 2100. To achieve this configuration, the implant assembly 2100 may be placed distal to the inserter 2500 and to the drill guide 2650. The second implant retention arm 2532 may then be opened by actuating the quick release lever 2590 in a first direction. The implant assembly 2100 may then be moved proximally to abut the proximal end of the implant assembly 2100 with the distal end of the drill guide 2650, such that the implant assembly 2100 is also intermediate the first and second implant retention arms 2531, 2532. The second implant retention arm 2532 may then be closed by actuating the quick release lever 2590 in a second direction in order to engage opposing sides of the implant assembly 2100 with the first and second implant retention arms 2531, 2532 in order to couple the implant assembly 2100 to the head 2510 of the inserter 2500, as shown in FIG. 36C).

Once the drill guide 2650 and the suitable implant assembly 2100 are coupled to the head 2510 of the inserter 2500, the inserter head 2510 may then be inserted into the patient and the implant assembly 2100 may be placed within a vertebral space of the patient in preparation for securing the implant assembly 2100 within the vertebral space of the patient with one or more bone screws 2131, 2141.

Figure 37A:
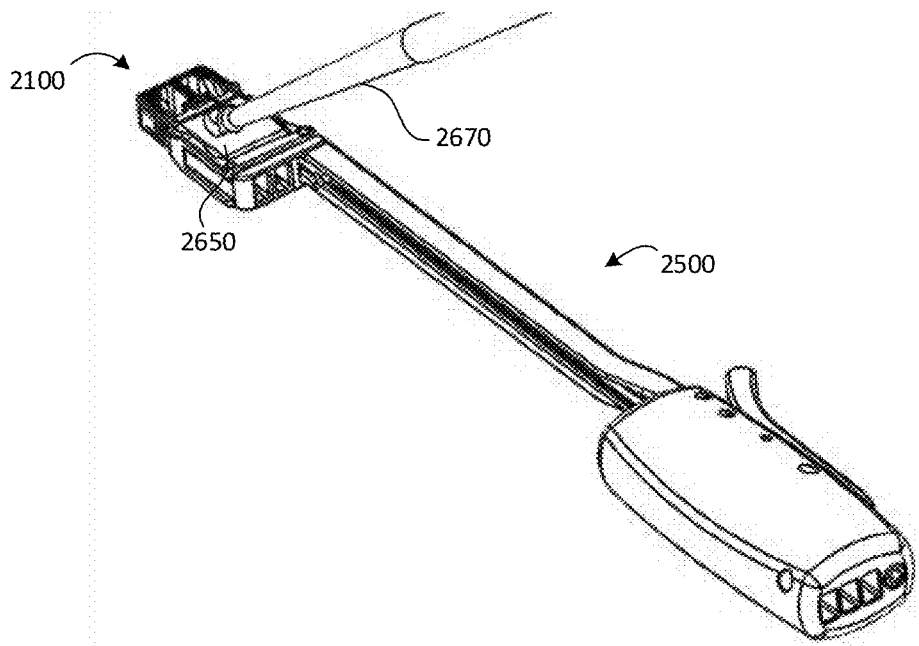
FIG. 37A is a perspective view of the inserter of FIG. 36C with a drill tool inserted through an aperture of the drill guide.
Figure 37B:
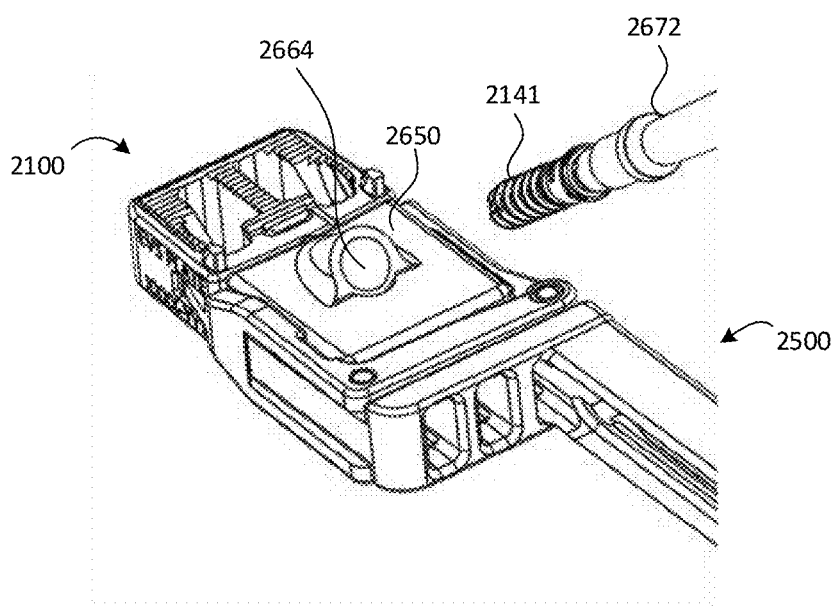
FIG. 37B is a perspective view of the distal end of the inserter of FIG. 36C with a bone screw and driver tool for insertion into the aperture of the drill guide.
Figure 38A:
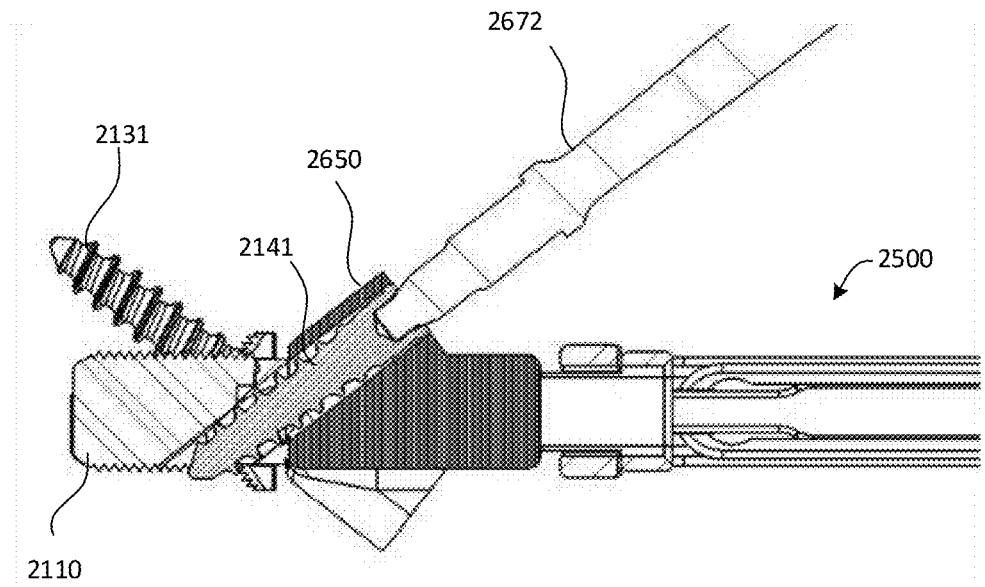
FIG. 38A-B are section views, along the sagittal plane, of the assembly of FIGS. 34A-C coupled to the drill guide of FIGS. 35A-D.
Figure 38B:
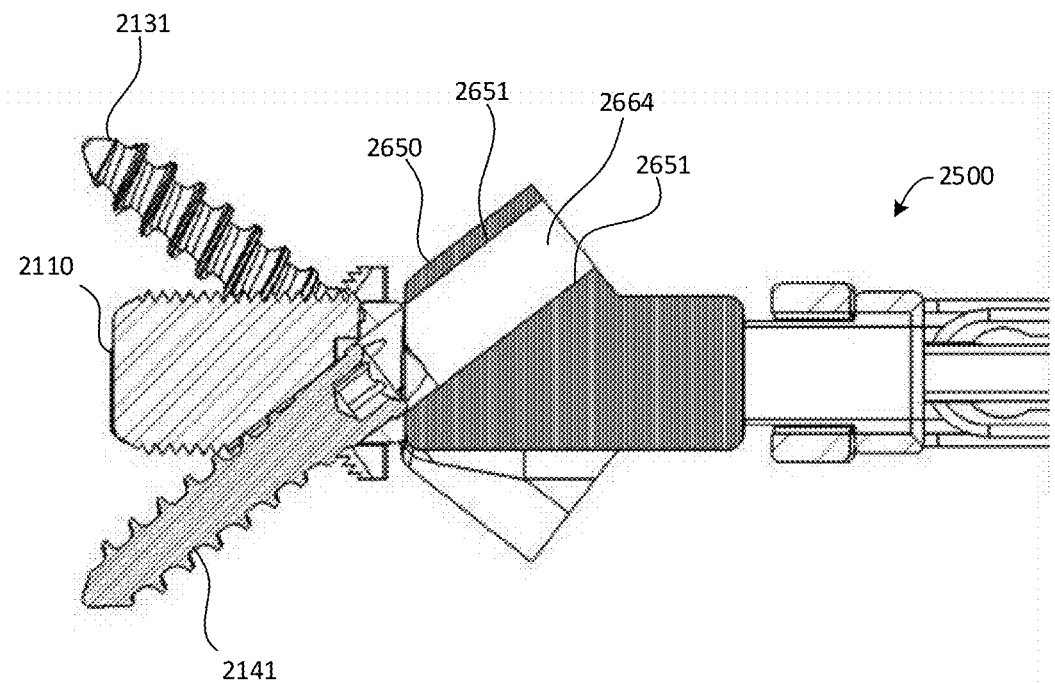

For example, FIGS. 37A-B show how a suitable tool 2670, such as a drill, a drill bit, an awl, etc., may be used to drill a hole in an inferior vertebral body. This may be accomplished by inserting the tool 2670 through the inferior drill guide aperture 2664 of the drill guide 2650 (see FIG. 37A) to guide the trajectory of the tool 2670 during formation of the hole in the bone. Once a suitable hole has been formed in the inferior vertebral body by the tool 2670, the tool 2670 may be removed and a bone screw 2141, coupled to a bone screw driver 2672, may be inserted through the inferior drill guide aperture 2664 of the drill guide 2650 to guide the trajectory of the bone screw 2141 and bone screw driver 2672 while affixing the bone screw 2141 to the inferior vertebral body. FIGS. 38A-B illustrate section views, taken along the sagittal plane, of the assembly shown in FIG. 37B at various stage of inserting the bone screw 2141.

Figure 39A:
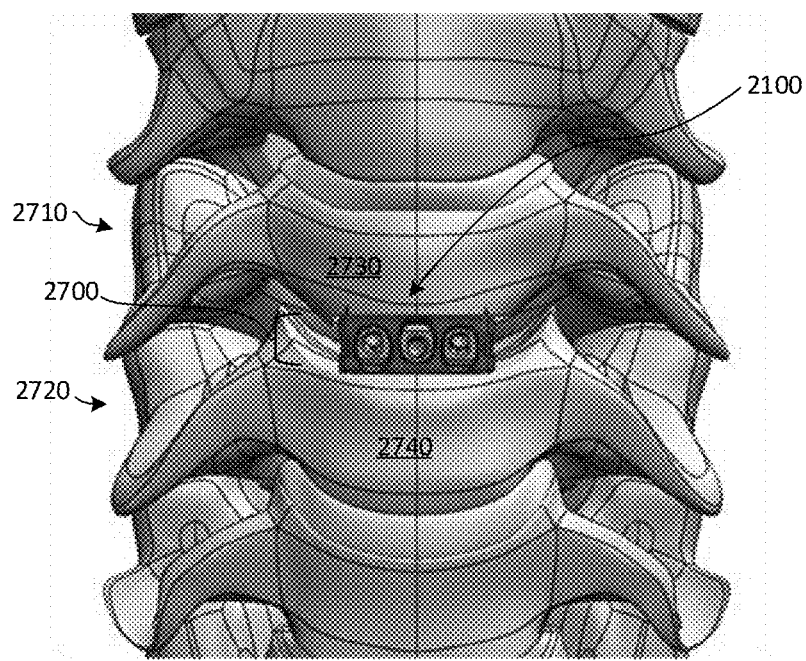
FIGS. 39A-B depict the assembly of FIGS. 34A-C implanted within an intervertebral space.
Figure 39B:
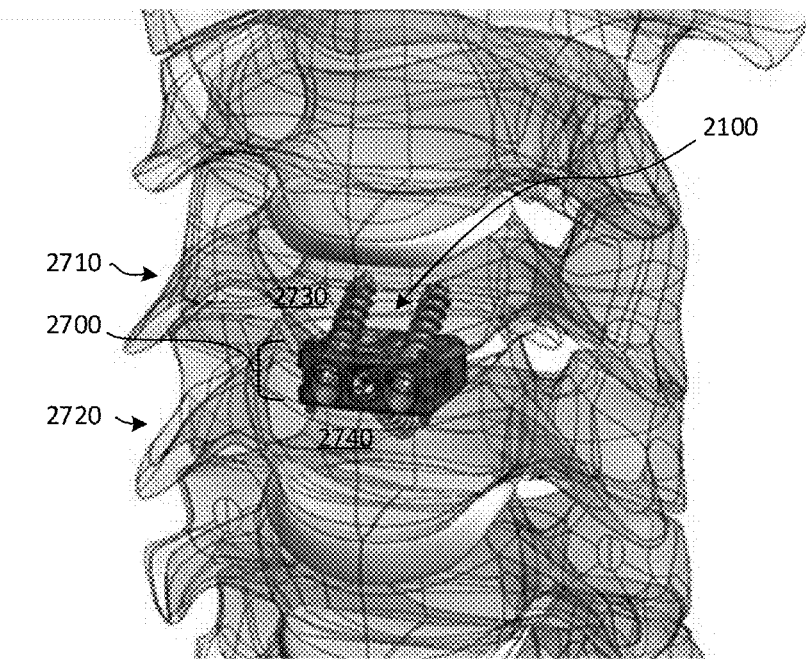

FIGS. 39A-B depict the implant assembly 2100 of FIGS. 34A-C implanted within an intervertebral space 2700 in its fully assembled state, with the superior bone screws 2131 and the inferior bone screw 2141 deployed to retain the assembly 2100 within the intervertebral space 2700 between a superior vertebra 2710 and an inferior vertebra 2720. As shown in FIG. 39B, the superior bone screws 2131 extend into a superior vertebral body 2730 of the superior vertebra 2710, and the inferior bone screw 2141 extends into an inferior vertebral body 2740 of the inferior vertebra 2720.

Each of the implants and tools described herein may be provided in one or more packages (not shown), in any configuration or number of implants, implant parts, tools, and/or instrumentation. The packaging may provide a safe and sterile environment that is suitable for use with medical devices and/or medical instrumentation. For example, in a particular embodiment a package may be provided which contains at least a carriage 2600, a first superior fastener 2130, and an inferior fastener 2140. The first superior fastener 2130 may be located in a first superior channel 2612 of the carriage 2600, and the inferior fastener 2140 may be located in an inferior channel 2614 of the carriage. In another particular embodiment, a package may be provided which contains at least a carriage 2600, a first superior fastener 2130, a second superior fastener 2130, and an inferior fastener 2140. The first and second superior fasteners 2130 may be located in a first superior channel 2612 and a second superior channel 2612, respectively, of the carriage 2600, and the inferior fastener 2140 may be located in an inferior channel 2614 of the carriage.

Figure 40:
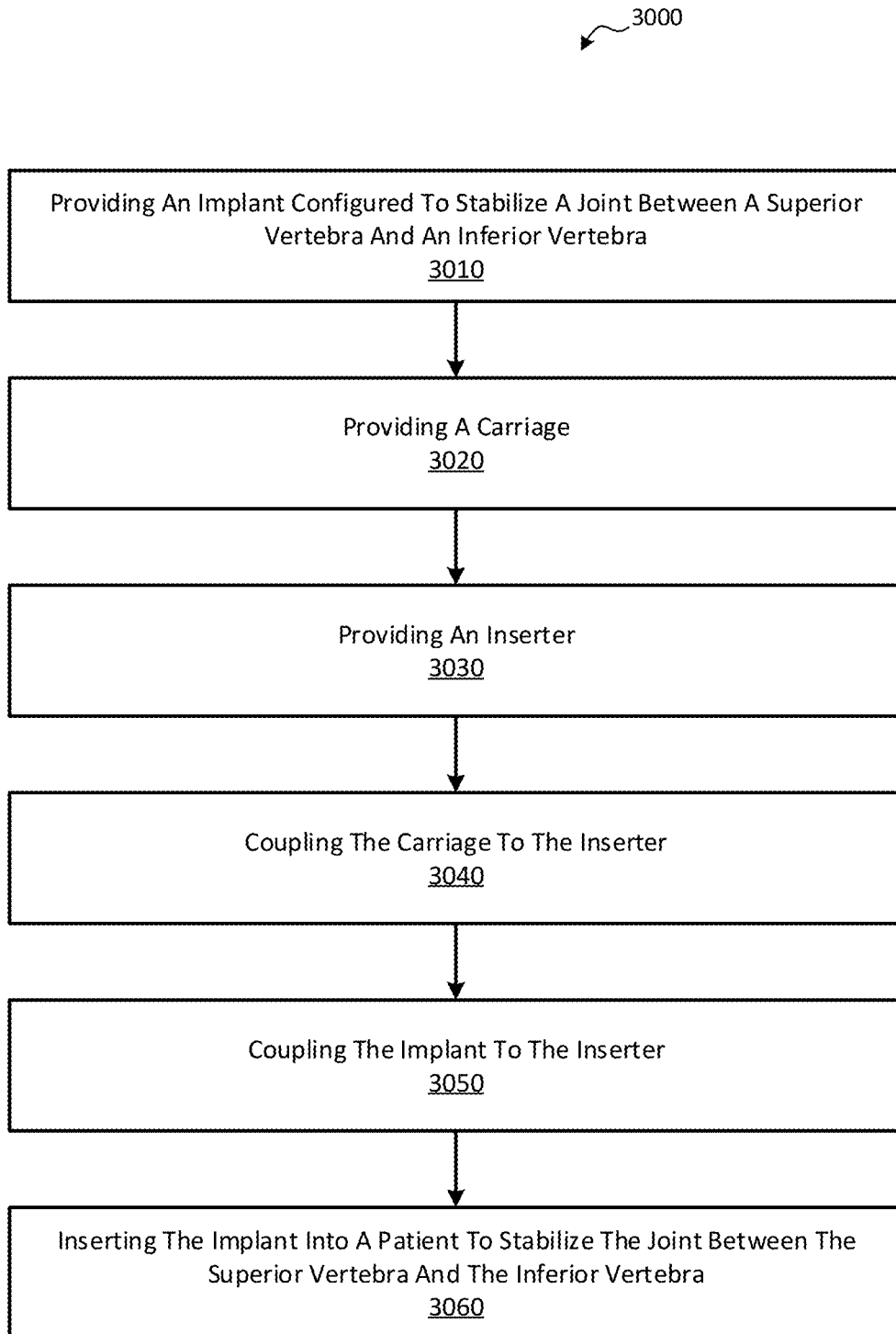
FIG. 40 illustrates a flowchart diagram of a method of inserting an implant, according to one embodiment of the present disclosure.
Figure 41:
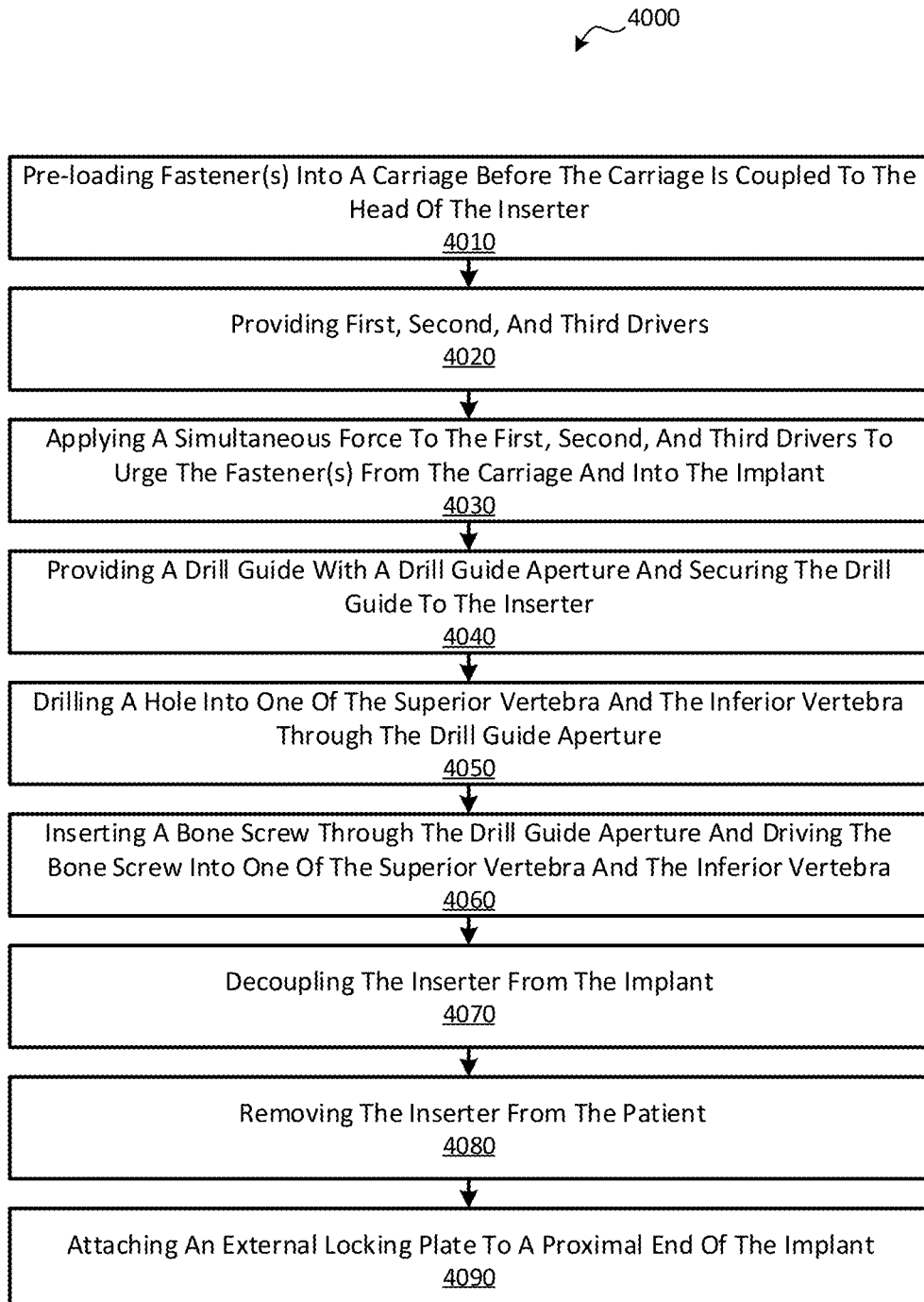
FIG. 41 illustrates a flowchart diagram of a method of inserting an implant, according to another embodiment of the present disclosure.

FIG. 40 illustrates a flowchart diagram for a method 3000 of inserting an implant into a patient to stabilize a joint between a superior vertebra and an inferior vertebra, according to one embodiment of the present disclosure. The method 3000 will be described in connection with the implant assembly 2100 and instrumentation of FIGS. 14A-39B. However, those of skill in the art will recognize that alternative implants, assemblies, systems, and instrumentation may be used in the performance of the method 3000, and the implant assembly 2100 and instrumentation of FIGS. 14A-39B may also be utilized in connection with alternative methods.

The method 3000 may start with a step 3010 in which an implant assembly 2100, configured to stabilize a joint between a superior vertebra and an inferior vertebra, may be provided. The implant assembly 2100 may be any implant, or portion of an implant, that is disclosed herein. The implant may include at least one fastener and the at least one fastener may be of any type that is disclosed herein.

In a step 3020, a carriage may be provided. The carriage may be, for example, the carriage 2600 shown in FIGS. 24A-D. In one embodiment, the at least one fastener may be pre-loaded in the carriage 2600, as previously described herein. However, in other embodiments the at least one fastener may be provided separate from the carriage 2600.

In a step 3030, an inserter may be provided. In one embodiment, the inserter may be the inserter 2500 shown in FIGS. 27-29B. The inserter 2500 may include a proximal end 2504, a distal end 2502, a shank 2520 intermediate the proximal end 2504 and the distal end 2502, a handle 2610 at the proximal end 2504 of the inserter 2500 and a head 2510 at the distal end 2502 of the inserter 2500. The head may include a first implant retention arm 2531 and a second implant retention arm 2532. The first and second implant retention arms 2531, 2532 may be configured to engage opposing sides of the implant assembly 2100 to removably couple the implant assembly 2100 to the head of the inserter 2500. The inserter 2500 may also include a carriage housing space 2595 located intermediate the first and second implant retention arms 2531, 2532 and distal to the shank 2520 of the inserter 2500.

In a step 3040, the carriage 2600 may be coupled to the inserter 2500 by placing the carriage 2600 within the carriage housing space 2595, as previously described herein. Once the carriage 2600 has been coupled to the inserter 2500, the method 3000 may proceed to a step 3050.

In the step 3050, the implant assembly 2100 may be further coupled to the inserter 2500 by placing the implant assembly 2100 between the first and second implant retention arms 2531, 2532 and engaging opposing sides of the implant assembly 2100 with the first and second implant retention arms 2531, 2532 of the inserter 2500, as previously described herein.

Once the implant assembly 2100 has been coupled to the inserter 2500, the method 3000 may proceed to a step 3060 in which the implant assembly 2100 may be inserted into the patient to stabilize a joint between a superior vertebra and an inferior vertebra of the patient, and the method 3000 may end.

Various steps of any method disclosed herein may be reordered, omitted, and/or replaced with different steps within the scope of the present disclosure. Those of skill in the art, with the aid of the present disclosure, will recognize that many variations may be made to any other method disclosed herein, depending on the particular surgical procedure to be carried out, as well as the configuration of the system used in the performance of that surgical procedure. Moreover, any methods disclosed herein may comprise one or more steps or actions for performing the described method. These method steps and/or actions may be interchanged with one another. In other words, unless a specific order of steps or actions is required for proper operation of the embodiment, the order and/or use of specific steps and/or actions may be modified.

FIG. 40 illustrates a flowchart diagram for a method 4000 of inserting an implant into a patient to stabilize a joint between a superior vertebra and an inferior vertebra, according to another embodiment of the present disclosure. The method 4000 will be described in connection with the implant assembly 2100 and instrumentation of FIGS. 14A-39B. However, those of skill in the art will recognize that alternative implants, assemblies, systems, and instrumentation may be used in the performance of the method 4000, and the implant assembly 2100 and instrumentation of FIGS. 14A-39B may also be utilized in connection with alternative methods. Moreover, any of the method steps of the method 4000 may be added to the method steps of method 3000 in any order or combination, and any of the method steps in the method 3000 may also be added to the method steps of method 4000, in any order or combination.

The method 4000 may start with a step 4010 in which at least one fastener may be pre-loaded into a carriage 2600 before the carriage 2600 is coupled to the head 2510 of an inserter 2500. The carriage 2600 may be configured to receive and carry the at least one fastener and the carriage 2600 may include at least one angled ramp 2616, 2618 configured to guide a trajectory of the at least one fastener, as the at least one fastener is urged from the carriage 2600 and into an implant assembly 2100.

Once the carriage is pre-loaded with the at least one fastener, and the carriage is coupled to the head 2510 of the inserter 2500, the method 4000 may proceed to a step 4020 in which first, second, and third drivers 2571, 2572, 2573 may be provided. Each of the first, second, and third drivers 2571, 2572, 2573 may have proximal ends 2574, 2575, 2576, respectively, and distal ends 2577, 2578, and 2579, respectively. The inserter may also include first, second, and third driver retention features 2561, 2562, 2563, 2551, 2552, 2553 which may be configured to engage the first, second, and third drivers 2571, 2572, 2573, respectively, between their distal ends 2577, 2578, 2579 and their proximal ends 2574, 2575, 2576, in order to guide the motion of each of the first, second, and third drivers 2571, 2572, 2573. Each of the proximal ends 2574, 2575, 2576 may also be exposed to permit the proximal ends 2574, 2575, 2576 to directly receive an impact. In one embodiment, impact(s) to the drivers 2571, 2572, 2573 may urge the drivers 2571, 2572, 2573 toward superior channels 2612 and/or an inferior channel 2614 of the carriage 2600, to urge superior fasteners 2130 within the superior channels toward superior fastener apertures 2240 of the implant assembly 2100, and also urge an inferior fastener 2140 toward an inferior fastener aperture 2242 of the implant assembly 2100.

In a step 4030, a simultaneous impact force may be applied to each of the first, second, and third drivers 2571, 2572, 2573 to urge the fasteners from the carriage 2600 and into the implant assembly 2100.

In a step 4040, a removably securable drill guide 2650 may be secured to the inserter 2500 in place of the carriage 2600. The drill guide 2650 may include at least one drill guide aperture 2662, 2664 sized and configured to receive at least one of a drill bit, an awl, a bone screw, and a bone screw driver. The at least one drill guide aperture 2662, 2664 may define at least one drill guide angled ramp 2651 configured to guide a trajectory of the at least one of the drill bit, the awl, the bone screw, and the bone screw driver, as the at least one of the drill bit, the awl, the bone screw, and the bone screw driver passes through the drill guide 2650 and into the implant assembly 2100.

In a step 4050, a hole may be drilled into one of a superior vertebra and an inferior vertebra through the at least one drill guide aperture 2662, 2664 of the drill guide 2650, utilizing a suitable tool 2670 that is guided by the drill guide angled ramp 2651 of the at least one drill guide aperture 2662, 2664.

In a step 4060, a bone screw may be inserted through the at least one drill guide aperture 2662, 2664 of the drill guide 2650. The bone screw may then be driven into the hole that was formed in one of the superior vertebra and the inferior vertebra by a suitable bone screw driver 2672 inserted through the at least one drill guide aperture 2662, 2664 of the drill guide 2650 in order to stabilize the joint between the superior vertebra and the inferior vertebra.

In a step 4070, the inserter 2500 may be decoupled from the implant assembly 2100, after the implant assembly 2100 has been inserted into the patient and secured within an intervertebral space of the patient, and the decoupled inserter 2500 may then be removed from the patient in a step 4080.

In a step 4090, a locking plate 2160 may then be attached to a proximal end of the implant assembly 2100. The locking plate 2160 may be configured to prevent the at least one fastener from backing out of the implant assembly 2100 after the implant assembly 2100 has been inserted into the patient and secured within the intervertebral space, and the method 4000 may end.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The Figures may show simplified or partial views, and the dimensions of elements in the Figures may be exaggerated or otherwise not in proportion for clarity. In addition, the singular forms "a," "an," and "the" include plural referents unless the context clearly dictates otherwise. Thus, for example, reference to a terminal includes reference to one or more terminals. In addition, where reference is made to a list of elements (e.g., elements a, b, c), such reference is intended to include any one of the listed elements by itself, any combination of less than all of the listed elements, and/or a combination of all of the listed elements.

The term "substantially" means that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

As used herein, the term "proximal", "top", "up" or "upwardly" refers to a location on the device that is closest to the clinician using the device and farthest from the patient in connection with whom the device is used when the device is used in its normal operation. Conversely, the term "distal", "bottom", "down" or "downwardly" refers to a location on the device that is farthest from the clinician using the device and closest to the patient in connection with whom the device is used when the device is used in its normal operation.

As used herein, the term "in" or "inwardly" refers to a location with respect to the device that, during normal use, is toward the inside of the device. Conversely, as used herein, the term "out" or "outwardly" refers to a location with respect to the device that, during normal use, is toward the outside of the device.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A system for stabilizing a joint between a superior vertebra and an inferior vertebra, the system comprising:
    an implant comprising:
        an anterior end;
        a posterior end;
        a superior fastener aperture formed in the anterior end; and
        an inferior fastener aperture formed in the anterior end;
        a superior bone-facing surface extending between the anterior end and the posterior end; and
        an inferior bone-facing surface extending between the anterior end and the posterior end;
    a superior fastener sized to be received in the superior fastener aperture and in a first interior space of the implant, and anchored in the superior vertebra; and
    an inferior fastener sized to be received in the inferior fastener aperture and in a second interior space of the implant, and anchored in the inferior vertebra;
    wherein the superior fastener and/or the inferior fastener comprises a spike comprising:
        a proximal end;
        a distal end; and
        a shank extending longitudinally between the proximal end and the distal end, the shank comprising:
            a convex side extending along a proximal-distal length of the shank; and
            a concave side extending along the proximal-distal length;
    wherein the proximal end defines a shoulder that is enlarged relative to the shank, the shoulder comprising a non-circular cross-sectional shape configured to lodge within one of the first interior space and the second interior space as the spike is anchored in one of the superior vertebra and the inferior vertebra; wherein the proximal end is shaped to define a threaded hole extending through at least part of the shoulder; and an inserter comprising: a head configured to removably engage the implant; a superior channel configured to retain the superior fastener; and an inferior channel configured to retain the inferior fastener.

2. The system of claim 1, wherein the convex side is smooth.

3. The system of claim 2, wherein the concave side comprises a plurality of bone-engagement fins arranged along a majority of the proximal-distal length of the shank, the plurality of bone-engagement fins extending away from a longitudinal center of the shank, wherein each of the plurality of bone-engagement fins occupies more than half, but less than all, of a perimeter of an associated cross-section of the shank taken perpendicular to the smooth surface of the shank.

4. The system of claim 2, wherein the concave side comprises a plurality of bone-engagement members that extend away from a longitudinal center of the shank toward the proximal end such that the bone engagement members set themselves in the superior vertebra or the inferior vertebra in a barb-like manner in response to force tending to urge the spike to pull out of the superior vertebra or the inferior vertebra.

5. The system of claim 2, wherein the shoulder extends from the concave side without interrupting the smooth shape of the convex side.

6. The system of claim 1, wherein the implant comprises:
a plate member comprising:
an anterior end plate at the anterior end, the anterior end plate comprising an anterior surface and a posterior surface;
the superior fastener aperture; and
the inferior fastener aperture; and
an interbody spacer comprising:
the posterior end;
a spacer anterior end configured to engage the posterior surface of the anterior end plate;
the superior bone-facing surface; and
the inferior bone-facing surface.

7. The system of claim 6, wherein:
the interbody spacer comprises:
a left lateral side comprising a left recess; and
a right lateral side comprising a right recess;
the plate member comprises:
a left posterior extension comprising a left engagement feature; and
a right posterior extension comprising a right engagement feature; and
the left engagement feature and the right engagement feature are receivable in the left recess and the right recess, respectively, to couple the interbody spacer to the plate member.

8. The system of claim 1, further comprising an inserter comprising:
a head configured to removably engage the implant;
a superior channel configured to receive the superior fastener and maintain the superior fastener in alignment with the superior fastener aperture; and
an inferior channel configured to receive the inferior fastener and maintain the inferior fastener in alignment with the inferior fastener aperture.

9. The system of claim 8, wherein the inserter further comprises:
a shank; and
a carriage, removably positioned between the shank and the head, in which the superior channel and the inferior channel are formed.

10. A system for stabilizing a joint between a superior vertebra and an inferior vertebra, the system comprising:
an implant comprising:
a plate member comprising:
an anterior end plate comprising an anterior surface and a posterior surface;
at least one superior fastener aperture formed in the anterior end plate; and
at least one inferior fastener aperture formed in the anterior end plate; and
an interbody spacer comprising:
a posterior end;
an anterior end configured to engage the posterior surface of the anterior end plate;
a superior bone-facing surface extending between the anterior end and the posterior end of the interbody spacer; and
an inferior bone-facing surface extending between the anterior end and the posterior end of the interbody spacer;
a superior fastener sized to be received in the superior fastener aperture and in a first interior space of the interbody spacer, and anchored in the superior vertebra; and
an inferior fastener sized to be received in the inferior fastener aperture and in a second interior space of the interbody spacer, and anchored in the inferior vertebra;
an inserter comprising:
a head configured to removably engage the implant;
a superior channel configured to receive the superior fastener and maintain the superior fastener in alignment with the superior fastener aperture; and
an inferior channel configured to receive the inferior fastener and maintain the inferior fastener in alignment with the inferior fastener aperture;
wherein the superior fastener and/or the inferior fastener comprises a spike comprising:
a proximal end;
a distal end; and
a shank extending longitudinally along a curved path between the proximal end and the distal end.

11. The system of claim 10, wherein the inserter further comprises:
a shank; and
a carriage, removably positioned between the shank and the head, in which the superior channel and the inferior channel are formed.

12. The system of claim 10, wherein the inserter further comprises:
a proximal end; and
a driver extending between the proximal end and the superior channel and/or the inferior channel, such that impact on the driver can be transmitted through the inserter to drive the superior fastener into the superior vertebra and/or drive the inferior fastener into the inferior vertebra.

13. The system of claim 10, wherein:
the superior fastener comprises a superiorly-angled ramp configured to direct the superior fastener superiorly as it enters the superior fastener aperture; and
the inferior fastener comprises an inferiorly-angled ramp configured to direct the inferior fastener inferiorly as it enters the inferior fastener aperture.

14. The system of claim 10, wherein:
the shank comprises:
a convex side extending along a proximal-distal length of the shank; and
a concave side extending along the proximal-distal length;
the proximal end defines a shoulder that is enlarged relative to the shank, the shoulder comprising a non-circular cross-sectional shape configured to lodge within one of the first interior space and the second interior space as the spike is anchored in one of the superior vertebra and the inferior vertebra;

the convex side is smooth;
the shoulder extends from the concave side without interrupting the smooth shape of the convex side; and
the proximal end of the spike comprises a hole with female threads.

15. The system of claim 10, wherein: the superior channel is shaped to permit rotation of the superior fastener about a first axis transverse to the superior fastener as the superior fastener passes from the superior channel into the superior fastener aperture; and the inferior channel is shaped to permit rotation of the inferior fastener about a second axis transverse to the inferior fastener as the inferior fastener passes from the inferior channel into the inferior fastener aperture.

16. A system for stabilizing a joint between a superior vertebra and an inferior vertebra, the system comprising:
an implant comprising:
an anterior end;
a posterior end;
a superior fastener aperture formed in the anterior end; and
an inferior fastener aperture formed in the anterior end;
a superior bone-facing surface extending between the anterior end and the posterior end; and
an inferior bone-facing surface extending between the anterior end and the posterior end;
a superior fastener sized to be received in the superior fastener aperture and in a first interior space of the implant, and anchored in the superior vertebra; and
an inferior fastener sized to be received in the inferior fastener aperture and in a second interior space of the implant, and anchored in the inferior vertebra;
wherein the superior fastener and/or the inferior fastener comprises a spike comprising:
a proximal end;
a distal end; and
a shank extending longitudinally between the proximal end and the distal end, the shank comprising:
a convex side extending along a proximal-distal length of the shank; and
a concave side extending along the proximal-distal length, the concave side having a concave surface;
wherein the proximal end defines a shoulder that is enlarged relative to the shank; wherein the shoulder is configured to lodge within one of the first interior space and the second interior space as the spike is anchored in one of the superior vertebra and the inferior vertebra;
wherein the concave side comprises a plurality of bone-engagement members, extending from the concave surface, that extend away from a longitudinal center of the shank toward the proximal end such that the bone engagement members set themselves in the superior vertebra or the inferior vertebra in a barb-like manner in response to force tending to urge the spike to pull out of the superior vertebra or the inferior vertebra;
wherein the shoulder extends for a first distance along the concave surface and a second distance, greater than the first distance, along the convex surface.

17. The system of claim 16, wherein:
the convex side is smooth; and
the shoulder extends from the concave side without interrupting the smooth shape of the convex side.

18. The system of claim 16, wherein:
the bone-engagement members are arranged along a majority of the proximal-distal length of the shank;
the bone-engagement members extend away from a longitudinal center of the shank; and
each of the bone-engagement members occupies more than half, but less than all, of a perimeter of an associated cross-section of the shank taken perpendicular to the convex side.

19. The system of claim 16, wherein the proximal end of the spike comprises a hole with female threads.

20. The system of claim 16, further comprising an inserter comprising:
a head configured to removably engage the implant;
a superior channel configured to receive the superior fastener and maintain the superior fastener in alignment with the superior fastener aperture; and
an inferior channel configured to receive the inferior fastener and maintain the inferior fastener in alignment with the inferior fastener aperture.

21. A system for stabilizing a joint between a superior vertebra and an inferior vertebra, the system comprising: an implant comprising: an anterior end; a posterior end; a superior fastener aperture formed in the anterior end; and an inferior fastener aperture formed in the anterior end; a superior bone-facing surface extending between the anterior end and the posterior end; and an inferior bone-facing surface extending between the anterior end and the posterior end; a driver comprising a driver distal end; and a superior fastener sized to be received in the superior fastener aperture and in a first interior space of the implant, and anchored in the superior vertebra; and an inferior fastener sized to be received in the inferior fastener aperture and in a second interior space of the implant, and anchored in the inferior vertebra; wherein the superior fastener and/or the inferior fastener comprises a spike comprising: a proximal end; a distal end; and a shank extending longitudinally between the proximal end and the distal end, the shank comprising: a convex side extending along a proximal-distal length of the shank, the convex side having a smooth, continuous shape from the proximal end to the distal end; and a concave side extending along the proximal-distal length; wherein the proximal end defines a shoulder that is enlarged relative to the shank, the shoulder comprising a non-circular cross-sectional shape configured to lodge within one of the first interior space and the second interior space as the spike is anchored in one of the superior vertebra and the inferior vertebra; wherein the shoulder is configured to receive impact from the driver distal end to drive the spike into one of the superior vertebra and the inferior vertebra.

* * * * *